(12) United States Patent
Elliman et al.

(10) Patent No.: US 11,918,687 B2
(45) Date of Patent: Mar. 5, 2024

(54) SDC-2 EXOSOME COMPOSITIONS AND METHODS OF ISOLATION AND USE

(71) Applicant: ORBSEN THERAPEUTICS LIMITED, Galway (IE)

(72) Inventors: Stephen J. Elliman, Galway (IE); Jack Kavanaugh, Los Angeles, CA (US); Larry Couture, Claremont, CA (US)

(73) Assignee: ORBSEN THERAPEUTICS LIMITED, Galway (IE)

(*) Notice: Subject to any disclaimer, the term of this patent is extended or adjusted under 35 U.S.C. 154(b) by 532 days.

(21) Appl. No.: 16/070,202

(22) PCT Filed: Jan. 13, 2017

(86) PCT No.: PCT/IB2017/000091
§ 371 (c)(1),
(2) Date: Jul. 13, 2018

(87) PCT Pub. No.: WO2017/122095
PCT Pub. Date: Jul. 20, 2017

(65) Prior Publication Data
US 2019/0015331 A1    Jan. 17, 2019

Related U.S. Application Data

(60) Provisional application No. 62/384,651, filed on Sep. 7, 2016, provisional application No. 62/337,752, filed on May 17, 2016, provisional application No. 62/279,534, filed on Jan. 15, 2016.

(51) Int. Cl.
| | | |
|---|---|---|
| A61K 9/127 | (2006.01) |
| A61K 35/00 | (2006.01) |
| A61K 35/12 | (2015.01) |
| A61K 38/17 | (2006.01) |
| A61P 3/00 | (2006.01) |
| A61P 29/00 | (2006.01) |

(52) U.S. Cl.
CPC ............ *A61K 9/1271* (2013.01); *A61K 35/00* (2013.01); *A61K 35/12* (2013.01); *A61K 38/1709* (2013.01); *A61K 38/177* (2013.01); *A61P 3/00* (2018.01); *A61P 29/00* (2018.01)

(58) Field of Classification Search
CPC ...... A61K 9/1271; A61K 35/00; A61K 35/12; A61K 38/1709; A61K 38/177; A61P 3/00; A61P 29/00
See application file for complete search history.

(56) References Cited

U.S. PATENT DOCUMENTS

| | | |
|---|---|---|
| 5,486,359 A | 1/1996 | Caplan, I et al. |
| 5,726,058 A | 3/1998 | Jalkanen et al. |
| 6,355,239 B1 | 3/2002 | Bruder et al. |
| 6,531,295 B1 | 3/2003 | Saunders et al. |
| 10,920,197 B2 | 2/2021 | Elliman |
| 2003/0100492 A1 | 5/2003 | Yayon |
| 2003/0225018 A1 | 12/2003 | Ekker et al. |
| 2004/0258670 A1 | 12/2004 | Laughlin et al. |
| 2005/0059147 A1 | 3/2005 | Seshi |
| 2005/0226864 A1 | 10/2005 | Hinton et al. |
| 2006/0078993 A1 | 4/2006 | Phan et al. |
| 2007/0264239 A1 | 11/2007 | Huard et al. |
| 2008/0241246 A1 | 10/2008 | Sakthivel et al. |
| 2010/0172885 A1 | 7/2010 | Pittenger et al. |
| 2010/0196329 A1 | 8/2010 | Ra et al. |
| 2010/0247577 A1 | 9/2010 | Foussat et al. |
| 2012/0122789 A1 | 5/2012 | Virag et al. |
| 2012/0207725 A1 | 8/2012 | Cho et al. |
| 2014/0356398 A1 | 12/2014 | Riddell et al. |
| 2015/0030615 A1 | 1/2015 | Derr et al. |
| 2015/0037292 A1 | 2/2015 | Ellman |
| 2016/0058832 A1 | 3/2016 | Ellman |
| 2016/0215265 A1 | 7/2016 | Elliman |
| 2016/0271211 A1 | 9/2016 | Elliman |
| 2019/0262421 A1 | 8/2019 | Elliman et al. |
| 2020/0158725 A1 | 5/2020 | Singh et al. |

FOREIGN PATENT DOCUMENTS

| | | |
|---|---|---|
| CN | 1678734 A | 10/2005 |
| EP | 1795588 A1 | 6/2007 |
| EP | 2545928 A1 | 1/2013 |
| EP | 3271396 A1 | 1/2018 |
| EP | 3416964 A4 | 9/2019 |
| JP | 2013508353 A | 3/2013 |
| JP | 2016516797 A | 6/2016 |
| JP | 2017532965 A | 11/2017 |
| KR | 20080075959 A | 8/2008 |
| KR | 20100106744 A | 10/2010 |

(Continued)

OTHER PUBLICATIONS

Haney, M. J., Klyachko, N. L., Zhao, Y., Gupta, R., Plotnikova, E. G., He, Z., . . . & Batrakova, E. V. (2015). Exosomes as drug delivery vehicles for Parkinson's disease therapy. Journal of Controlled Release, 207, 18-30. (Year: 2015).*

Ionescu, L., Byrne, R. N., van Haaften, T., . . . & Thébaud, B. (2012). Stem cell conditioned medium improves acute lung injury in mice: in vivo evidence for stem cell paracrine action. American Journal of Physiology-Lung Cellular and Molecular Physiology 303(11), L967-L977. (Year: 2012).*

Rani, S., Ryan, A. E., Griffin, M. D., & Ritter, T. (2015). Mesenchymal stem cell-derived extracellular vesicles: toward cell-free therapeutic applications. Molecular Therapy, 23(5), 812-823. (Year: 2015).*

Mitchell, J. P., Court, J., Mason, M. D., Tabi, Z., & Clayton, A. (2008). Increased exosome production from tumour cell cultures using the Integra CELLine Culture System. Journal of Immunological Methods, 335(1-2), 98-105. (Year: 2008).*

(Continued)

*Primary Examiner* — Allison M Fox
*Assistant Examiner* — Jennifer S Spence
(74) *Attorney, Agent, or Firm* — Wilson Sonsini Goodrich & Rosati

(57) ABSTRACT

Disclosed herein are compositions comprising isolated exosomes, for instance exosomes wherein at least 20% of the exosomes comprise SDC2, methods of isolation, and methods of use.

7 Claims, 14 Drawing Sheets

(56) References Cited

FOREIGN PATENT DOCUMENTS

| KR | 20120013915 A | 2/2012 | |
|---|---|---|---|
| KR | 101309910 B1 | 9/2013 | |
| WO | WO-02087609 A1 | 11/2002 | |
| WO | WO-03046141 A2 | 6/2003 | |
| WO | WO-03062386 A2 | 7/2003 | |
| WO | WO-2004003179 A1 | 1/2004 | |
| WO | WO-2007122823 A1 | 11/2007 | |
| WO | WO-2008100083 A1 | 8/2008 | |
| WO | WO-2009012357 A2 | 1/2009 | |
| WO | WO-2009105624 A2 | 8/2009 | |
| WO | WO-2010065239 A1 | 6/2010 | |
| WO | WO-2011153458 A2 | 12/2011 | |
| WO | WO-2012111997 A2 | 8/2012 | |
| WO | WO-2012125471 A1 * | 9/2012 | ............ C12N 5/0663 |
| WO | WO-2013117761 A1 * | 8/2013 | ............ A61K 9/0019 |
| WO | WO-2013172793 A1 | 11/2013 | |
| WO | WO-2014125277 A1 * | 8/2014 | ......... A61K 31/7105 |
| WO | WO-2014168548 A2 | 10/2014 | |
| WO | WO-2014170411 A1 * | 10/2014 | .............. A61P 29/00 |
| WO | WO-2015038075 A1 | 3/2015 | |
| WO | WO-2015048844 A1 * | 4/2015 | ............. A61K 35/12 |
| WO | WO-2017122095 A1 | 7/2017 | |
| WO | WO-2017141116 A1 | 8/2017 | |
| WO | WO-2020035741 A2 | 2/2020 | |

OTHER PUBLICATIONS

Tauro, B. J., Greening, D. W., Mathias, R. A., Ji, H., Mathivanan, S., Scott, A. M., & Simpson, R. J. (2012). Comparison of ultracentrifugation, density gradient separation, and immunoaffinity capture methods for isolating human colon cancer cell line LIM1863-derived exosomes. Methods, 56(2), 293-304. (Year: 2012).*

Lamparski HG, Metha-Damani A, Yao JY, Patel S, Hsu DH, Ruegg C, Le Pecq JB. Production and characterization of clinical grade exosomes derived from dendritic cells. Journal of immunological methods. Dec. 15, 2002;270(2):211-26. (Year: 2002).*

Lai, R. C., Tan, S. S., Teh, B. J., Sze, S. K., Arslan, F., De Kleijn, D. P., . . . & Lim, S. K. (2012). Proteolytic potential of the MSC exosome proteome: implications for an exosome-mediated delivery of therapeutic proteasome. International Journal of Proteomics, 2012. (Year: 2012).*

Mathivanan S, Simpson RJ. ExoCarta: A compendium of exosomal proteins and RNA. Proteomics. Nov. 2009;9(21):4997-5000. (Year: 2009).*

Rani, S., Ryan, A. E., Griffin, M. D., & Ritter, T. (2015). Mesenchymal stem cell-derived extracellular vesicles: toward cell-free therapeutic applications. Molecular Therapy, 23(5), 812-823. (Year: 2015) (Year: 2015).*

Ionescu L, Byrne RN, van Haaften T, et al. Stem cell conditioned medium improves acute lung injury in mice: in vivo evidence for stem cell paracrine action. American Journal of Physiology-Lung Cellular and Molecular Physiology. Dec. 1, 2012;303(11):L967-77 . . . (Year: 2012).*

Vader P, Mol EA, Pasterkamp G, Schiffelers RM. Extracellular vesicles for drug delivery. Advanced drug delivery reviews. Nov. 15, 2016;106:148-56. Available online Feb. 27, 2016 (Year: 2016).*

D'Arcy, S. (2012). Isolation and characterisation of novel stromal cell populations from human bone marrow (Doctoral dissertation). (Year: 2012).*

Stender S, Murphy M, O'Brien T, Stengaard C, Ulrich-Vinther M, Soballe K, Barry F. Adeno-associated viral vector transduction of human mesenchymal stem cells. Eur Cell Mater. May 31, 2007;13(93-99):99. (Year: 2007).*

Hall BM, Henning AE, Bartlett JS. 973. Efficient Transduction of Bone Marrow-Derived Mesenchymal Stem Cells for Cancer Gene Therapy Using a Tropism-Modified Adeno-Associated Virus (AAV) Vector. Molecular Therapy. May 1, 2004;9(S1):S372. (Year: 2004).*

Australian Patent Application No. 2014255755 Office Action dated Sep. 7, 2018.

Canadian Patent Application No. 2863821 Examination Report dated Nov. 6, 2018.

European Patent Application No. 14718403.0 Examination Report dated Jan. 2, 2019.

European Patent Application No. 16714673.7 Office Action dated Sep. 12, 2018.

European Patent Application No. 18190005.1 European Search Report dated May 3, 2019.

International Patent Application No. PCT/IB2018/000687 International Search Report and Written Opinion dated Dec. 5, 2018.

International Patent Application No. PCT/IB2018/000939 International Search Report and Written Opinion dated Dec. 19, 2018.

Keifer et al.: "Inhibition of NF-êB Activity by Thalidomide through Suppression of IêB Kinase Activity", Journal of Biological Chemistry, American Society for Biochemistry and Molecular Biology, US, vol. 276, No. 25, Jun. 22, 2001, pp. 22382-22387.

PCT/IB2017/000091 International Preliminary Report on Patentability dated Jul. 26, 2018.

Sanz-Nogués et al.: Angiogenic assessment of ORBCEL TM, a novel stromal cell population for treating Critical Limb Ischaemia (CLI); Cytotherapy, vol. 19, S198 (2017).

Sattler et al.: "Inhibition of T-Cell Proliferation by Murine Multipotent Mesenchymal Stromal Cells is Mediated by CD39 Expression and Adensoine Generation", Cell Transplantation, vol. 20, No. 8, Sep. 1, 2011, pp. 1221-1230.

U.S. Appl. No. 14/377,597 Final Office Action dated Jan. 14, 2019.
U.S. Appl. No. 15/089,435 Final Office Action dated Sep. 3, 2019.
U.S. Appl. No. 15/089,435 Non-Final Office Action dated Nov. 14, 2018.
U.S. Appl. No. 16/009,048 Restriction Requirement dated Jun. 28, 2019.

(Abstract C34.6) Abstracts of papers presented at Glyco XVI, XVI International Symposium on Glycoconjugates, Aug. 19-24, 2001, The Hague, The Netherlands, Glycoconjugate Journal, 18(1-2):1-202, 2001.

Alvarez-Viejo, Maria: CD271 as a marker to identify mesenchymal stem cells from diverse sources before culture. World Journal of Stem Cells, vol. 7, No. 2, Jan. 1, 2015, p. 470.

Australian Patent Application No. 2013217870 Examination Report dated Apr. 24, 2018.

Australian Patent Application No. 2013217870 Examination Report No. 1 dated Nov. 1, 2017.

Australian Patent Application No. 2014255755 Examination Report No. 1 dated Oct. 10, 2017.

Australian Patent Application No. 2014255755 Examination Report No. 2 dated Jun. 27, 2018.

Bermadez-Lugo et al., Exploration of the valproic acid binding site on histone deacetylase 8 using docking and molecular dynamic simulations. Journal of Molecular Modeling, 18(6):2301-2310, 2011.

Biancone et al., Therapeutic potential of mesenchymal stem cell-derived microvesicles. Nephrol Dial Transplant. 27(8):3037-3042, 2012.

British Society for Matrix Biology—Spring 2012 Meeting Report. International Journal of Experimental Pathology, 94:A1-A48, 2013.

Carlotti, Francoise, et al., Isolated human islets contain a distinct population of mesenchymal stem cells, Islets, p. 164-173 May/Jun. 2010.

Chinese Patent Application No. 201380019351.0 Third Office Action dated Jan. 12, 2017.

Christianson et al. Heparan sulfate proteoglycan as a cell-surface endocytosis receptor. Matrix Biology, 35:51-55, 2014.

Chung et al., Human Embryonic Stem Cell Lines Generated without Embryo Destruction. Cell Stem Cell, vol. 2, No. 2, 2008, pp. 113-117.

CN201480025184.5 Office Action dated Jul. 4, 2018.

Costabel et al., Pirfenidone in idiopathic pulmonary fibrosis: Expert panel discussion on the management of drug-related adverse events. Adv. Ther., 31:375-391, 2014.

Cuthbert et al., Single-platform quality control assay to quantify multipotential stromal cells in bone marrow aspirates prior to bulk manufacture or direct therapeutic use. Cytotherapy, 2012, vol. 14, No. 4, pp. 431-440.

(56) References Cited

OTHER PUBLICATIONS

Database: NCBI Reference Sequence: NP_002989.1 (2 pgs.) (Jan. 20, 2003).
Dieudonne et al. Targeted inhibition of T-cell factor activity promotes syndecan-2 expression and sensitization to doxorubicin in osteosarcoma cells and bone tumors in mice. J Bone Miner Res 27(10):2118-2129 (2012).
Dieudonne et al. High Wnt signaling represses the proapoptotic proteoglycan syndecan-2 in osteosarcoma cells. Cancer Res 70(13):5399-5408 (2010).
Duffy et al., Mesenchymal stem cell inhibition of T-helper 17 cell-differentiation is triggered by cell-cell contact and mediated by prostaglandin E2 via the EP4 receptor. European Journal of Immunol., 41:2840-2851, 2011.
European Patent Application No. 15158384.6 Extended European Search Report dated Jul. 8, 2015, 10 pages.
Eskildsen et al., MicroRNA-138 regulates osteogenic differentiation of human stromal (mesenchymal) stem cells in vivo. PNAS, 108(15):6139-6144, 2011.
Essner et al., Syndecan-2. International Journal of Biochemistry and Cell Biology. 38(2):152-156, 2006.
European Patent Application No. 14718403.0 Communication dated Apr. 6, 2017.
European Patent Application No. 14718403.0 Communication dated Mar. 6, 2018.
European Patent Application No. 15158384.6 Communication dated Apr. 7, 2017.
Gangoda et al., Cortactin enhances exosome secretion without altering cargo. Journal of Cell Biology, 214(2):129-131, 2016.
GB1202319.8 Search Report dated Jun. 11, 2012, 3 pages.
Gronthos et al. Molecular and cellular characterisation of highly purified stromal stem cells derived from human bone marrow. (2003) Journal of Cell Science, vol. 116:1827-1835.
Hohki et al., Blockade of interleukin-6 signaling suppresses experimental autoimmune uveoretinitis by the inhibition of inflammatory Th17 responses. Experimental Eye Research, 91:162-170, 2010.
Horwitz et al., Clarification of the nomenclature for MSC: The international society for cellular therapy position statement. Cytotherapy, 7:393-395, 2005.
Hsu et al. Neural stem cells, neural progenitors, and neurotrophic factors. Cell Transplant 16(2):133-150 (2007).
Huang et al., Prognostic significance of altered expression of SDC2 and CYR61 in esophageal squamous cell carcinoma. Oncology Reports, 21:1123-1129, 2009.
Human/Mouse Integrin [alpha]11 Antibody. Jun. 30, 2015 (Jun. 30, 2015), 1 page, Retrieved from the Internet: URL:http://www.rndsystems.com/pdf/MAB4235.pdf.
Indian Patent Application No. 1777/KOLNP/2014 Office Action dated May 31, 2018.
Japanese Patent Application No. 2016-508166 Office Action dated Jun. 12, 2018.
Japanese Patent Application No. 2016-508166 Office Action dated Sep. 25, 2017.
Jones, E., et al., Large-Scale Extraction and Characterization of CD271+ Multipotential Stromal Cells From Bone in Health and Osteoarthritis, Arthritis & Rhuematism, vol. 62, No. 7, Jul. 2010, pp. 1944-1954.
Kaltz et al. Novel markers of mesenchymal stem cells defined by genome-wide gene expression analysis of stromal cells from different sources. Experimental Cell Research, Academic Press, US, vol. 316, No. 16, (Oct. 1, 2010), pp. 2609-2617.
Khan et al., CD4+ T Cell-derived Novel Peptide Thp5 Induces Interleukin-4 Production in CD4+ T Cells to Direct T Helper 2 Cell Differentiation. J Biol Chem, 287, 2830-2835, 2011.
Kozanoglu, Ilknur, et al., Human bone marrow mesenchymal cells express NG2: possible increase in discriminative ability of flow cytometry during mesenchymal stromal cell identification. Cytotherapy (2009) vol. 11, No. 5, pp. 527-533.
KR1317507 Abstract from STN CAPlus database (1 pg) (2015).
Lambaerts et al., The signalling mechanisms of syndecan heparen sulphate proteoglycans Current Opinion Cell Biol., 21(5):662-669 (2009).
Lim et al., Cell surface heparan sulfate proteoglycans control adhesion and invasion of breast carcinoma cells Molecular Cancer, 14:15, 18 pages, 2015.
Lim et al., Syndecan-2 regulation of morphology in breast carcinoma cells is dependent on RhoGTPases. Biochimica et Biophysica Acta, 1840:2482-2490, 2014.
Llinas, L, et al., Expression profiles of novel cell surface molecules on B-cell subsets and plasma cells as analyzed flow cytometry, Immunology Letters, vol. 134, No. 2, Jan. 30, 2011, pp. 113-121.
Lotufo et al., Expression of cell-surface heparan sulfate proteoglycans in human cyclosporin-induced gingival overgrowth. J. Periodont Res., 42:553-558, 2007.
Ludlow et al., Large scale production of extracellular vesicles in a hollow fiber bioreactor system. Poster. www.FiberCellSystems.com, 1 page, 2016.
Lyons et al. Determination of lymphocyte division by flow cytometry. Journal of Immunological Methods, 171:131-137, 1994.
Manon-Jensen et al., Proteoglycans in health and disease: the multiple roles of syndecan shedding FEBS Journal, 277(19):3876-3889, 2010.
Matesanz-Isabel et al., New B-cell CD molecules. Immunology Letters, 2011, vol. 134, No. 2, pp. 104-112.
Mendez-Ferrer et al., Mesenchymal and haematopoietic stem cells form a unique bone marrow niche Nature, 466:829-836 (2010).
Mendez-Ferrer et al., Mesenchymal and haematopoietic stem cells form a unique bone marrow niche Nature, 466:829-836 (2010) Supplementary Information, 21 pages.
Mukhopadhyay, et al., Syndecan-2 and Decorin: Proteoglycans With a Difference—Implications in Keloid Pathogenesis, Journal of Trauma Injury Infection and Critical Care, 68(4):999-1008, 2010.
Mytilinalou et al., Research Communication: Syndecan-2 is a key regulator of transforming growth factor beta 2/Smad2-mediated adhesion in fibrosarcoma cells. IUBMB Life, 65(2):134-143 (2013).
Nauta et al., Chapter 2, Humoral and Cellular Immunity, in: Statistics in Clinical Trials, Berlin: Springer-Verlag, p. 13-17, 2011.
Nierhoff et al. New cell surface markers for murine fetal hepatic stem cells identified through high density complementary DNA microarrays. Hepatology 46(2):535-547 (2007).
Nish et al., T cell-intrinsic role of IL-6 signaling in primary and memory responses. Elife, 3:e01949, 21 page (2014).
Paris et al., Opposing Roles of Syndecan-1 and Syndecan-2 in Polyethyleneimine-mediated Gene Delivery. J Biol Chem, 283:7697-7704, 2008.
Parish, Fluorescent dyes for lymphocyte migration and proliferation studies. Immunology and Cell Biology, 77:499-508, 1999.
Park et al., Syndecan-2 mediates adhesion and proliferation of colon carcinoma cells. The Journal of Biological Chemistry, 277(33):29730-29736, 2002.
PCT Patent Application No. PCT/EP2016/056065 International Search Report and Written Opinion dated May 20, 2016.
PCT Patent Application No. PCT/US2016/023178 International Search Report and Written Opinion dated Jun. 13, 2016.
PCT/EP2013/052692 International Preliminary Report on Patentability under Chapter II completed Mar. 13, 2014.
PCT/EP2013/052692 International Search Report completed Jun. 10, 2013.
PCT/EP2013/052692 Written Opinion Report completed Jun. 10, 2013.
PCT/EP2014/057830 International Preliminary Report on Patentability dated Oct. 20, 2015.
PCT/EP2014/057830 International Search Report and Written Opinion dated Jul. 17, 2014.
PCT/US2016/023178 International Preliminary Report on Patentability dated Sep. 26, 2017.
PCT/US2017/000091 International Search Report and Written Opinion dated May 12, 2017.
Pennock, Natahan D. et al. T cell response: naive to memory and everything in between. Adv. Physiol. Educ. 37:273-283 (2013).

(56) References Cited

OTHER PUBLICATIONS

Rovira-Clave, Xavier et al. Syndecan-2 can promote clearance of T-cell receptor/CD3 from the cell surface. Immunology, 137(3):214-225 (Nov. 2012):E-Pub: Oct. 2, 2012.
Rozemuller, H., et al., Prospective isolation of mesenchymal stem cells from multiple mammalian species using cross-reacting anti-human monoclonal antibodies. Stem Cells and Development, vol. 19, No. 12, Dec. 1, 2010, pp. 1911-1921.
Ruiz et al., Syndecan-2 is a novel target of insulin-like growth factor binding protein-3 and is over-expressed in fibrosis. Plos One, 7(8):1-4, 2012.
Russian Patent Application No. 2014136711 Office Action dated Jun. 1, 2017.
Russian Patent Application No. 2014136711 Official Action dated Feb. 23, 2017.
Russian Patent Application No. 2015148769 Office Action dated Mar. 19, 2018.
Shi et al., Syndecan-2 exerts antifibrotic effects by promoting caveolin-1-mediated transforming growth factor-β receptor I internalization and inhibiting transforming growth factor-β1 signaling. Am J Respir Crit Care Med, 188:831-841, 2013.
Si et al. CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Silva et al. The Profile of Gene Expression of Human Marrow Mesenchymal Stem Cells (2003) Stem Cells: vol. 21: 661-669.
Sinha et al., Cortactin promotes exosome secretion by controlling branched actin dynamics. The Journal of Cell Biology, 214(2):197-213, 2016.
Stepp et al., Syndecan-1 and its expanding list of contacts. Advances in Wound Care, 4(4):235-249, 2015.
Tang et al., Calcitriol suppresses antiretinal autoimmunity through inhibitory effects on the Th17 effector response. The Journal of Immunology, 182:4624-4632, 2009.
Technical Data Sheet, Purified Mouse Anti-human CD271, Jun. 6, 2013, p. 1-2.
Teixe et al., Corrigendum to Syndecan-2 and -4 expressed on activated primary human CD4+lymphocytes can regulate T cell activation. Molecular Immunology, 51:368, 2012.
Teixe et al., Syndecan-2 and -4 expressed on activated primary human CD4+ lymphocytes can regulate T cell activation. Molecular Immunology, 45:2905-2919, 2008.
Theocharis et al., Insights into the key roles of proteoglycans in breast cancer biology and translational medicine. Biochimica et Biophysica Acta, 1855:276-300, 2015.
Turashev et al. Condition, destruction and reconstruction of the pericellular carbohydrate membrane of the luminal vascular surface in atherogenesis, Cardiological bulletin 2(2):64-68 (2007) (English Abstract).
UNIPROT:P34741, XP002726498, 3 pages, printed Jun. 26, 2014, http://ibis.internal.epo.org/exam/dbfetch.jsp?id=UNIPROT•P3474I.
U.S. Appl. No. 14/377,597 Office Action dated Apr. 7, 2016.
U.S. Appl. No. 14/377,597 Office Action dated Aug. 15, 2018.
U.S. Appl. No. 14/377,597 Office Action dated Jan. 30, 2017.
U.S. Appl. No. 14/377,597 Office Action dated May 12, 2017.
U.S. Appl. No. 14/377,597 Office Action dated Nov. 6, 2015.
U.S. Appl. No. 14/377,597 Office Action dated Sep. 9, 2016.
U.S. Appl. No. 14/785,001 Final Office Action dated Jun. 27, 2018.
U.S. Appl. No. 14/785,001 Office Action dated Dec. 15, 2017.
U.S. Appl. No. 14/785,001 Office Action dated Feb. 15, 2017.
U.S. Appl. No. 14/785,001 Office Action dated Jun. 20, 2016.
U.S. Appl. No. 15/074,681 First Action Interview Pilot Program Pre-Interview Communication dated Dec. 9, 2016.
U.S. Appl. No. 15/074,681 Office Action dated Apr. 27, 2017.
U.S. Appl. No. 15/074,681 Office Action dated Nov. 2, 2017.
U.S. Appl. No. 15/074,681 Restriction Requirement dated Aug. 22, 2016.
U.S. Appl. No. 15/089,435 Office Action dated Oct. 4, 2017.
Whitford et al., Continuous production of exosomes: Utilizing the technical advantages of hollow-fiber bioreactor technology. Genetic Engineering & Biotechnology News, 35(16):2 pages, 2015.
Wieczorek et al., Gene expression profile of mouse bone marrow stromal cells determined by cDNA microarray analysis.Cell Tissue Res. 311(2):227-237 (2003).
Yan, Xin-Long, et al., Migration of Dorsal Aorta Mesenchymal Stem Cells Induced by Mouse Embryonic Circulation, Dynamics 240: 65-74 (2011).
Brand: Crohn's disease: Th1, Th17 or both? The change of a paradigm: new immunological and genetic insights implicate Th17 cells in the pathogenesis of Crohn's disease. Gut. 58:1152-1167 (2009).
Colombel et al.: Adalimumab Safety in Global Clinical Trials of Patients with Crohn's Disease. Inflammatory Bowel Disease. 15:1308-1319 (2009).
Desreumax et al.: Safety and efficacy of antigen-specific regulatory T-cell therapy for patients with refractory Crohn's disease. Abstract. Gastroenterology. 143 (2012).
Green: Understanding NSAIDs: From Aspirin to COX-2. Clinical Cornerstone. 3:50-59 (2001).
Hagymasi et al.: Stem cell treatment in the treatment of gastrointestinal diseases. Orvosi Hetilap. 149(31):1449-1455 (2008).
Jafarzadeh et al.: Serum levels of interleukin (IL)-13, IL-17 and IL-18 in patients with ischemic heart disease. Anatolian Journal of Cardiology/Anadolu Kardiyoloji Derigisi. 9(2):75-83 (2009).
Kelsen et al.: FoxP3+CD4+CD25+ T cells with regulatory properties can be cultured from colonic mucosa of patients with Crohn's disease. Clinical and Experimental Immunology. 141:549-557 (2005).
Li et al.: Human Papillomavirus Infection Correlates with Inflammatory Stat3 Signaling Activity and IL-17 Level in Patients with Colorectal Cancer. PLoS One. 10(2):e0188391 16 pages (2015).
Shibui et al.: Th17 cell-derived IL-17 is dispensable for B cell antibody production. Cytokine. 59:108-114 (2012).
U.S. Appl. No. 16/009,048 Office Action dated Dec. 13, 2019.
U.S. Appl. No. 16/155,732 Office Action dated Sep. 30, 2021.
Williams et al.: The role of aspirin in cardiovascular diseases—forgotten benefits?. Expert Opinion in Pharmacotherapeutics. 5:109-115 (2004).
NCBI. GenPept, UniProtKB/Swiss-Prot, Accession No. P34741 (2022).
U.S. Appl. No. 16/155,732 Office Action dated Apr. 5, 2022.
Frantz et al. The extracellular matrix at a glance. Cell Science at a Glance 123, (2010), 4195-4200.
Hayes et al.: Mesenchymal stem cells—a promising therapy for Acute Respiratory Distress Syndrome. F1000 Med Rep. 4:2:1-7 (2012).
Korean Application No. 10-2015-7032129 Notice of Preliminary Rejection dated Oct. 14, 2021.
Nombela-Arrieta et al.: The elusive nature and function of mesenchymal stem cells. Nature Rev Mol Cell Bio. 12:126-131 (2011).
Prante et al.: The Formation of Extracellular Matrix During Chondrogenic Differentiation of Mesenchymal Stem Cells Correlates with Increased Levels of Xylosyltransferase I. Stem Cells. 24:2252-2261 (2006).
U.S. Appl. No. 14/377,597 Final Office Action dated Oct. 1, 2020.
U.S. Appl. No. 14/377,597 Office Action dated Feb. 20, 2020.
U.S. Appl. No. 14/377,597 Office Action dated Jun. 30, 2021.
U.S. Appl. No. 14/377,597 Office Action dated Oct. 7, 2019.
U.S. Appl. No. 15/089,435 Office Action dated Jun. 10, 2020.
U.S. Appl. No. 16/009,048 Final Office Action dated Jul. 24, 2020.
U.S. Appl. No. 16/562,206 Final Office Action dated Nov. 27, 2020.
U.S. Appl. No. 16/562,206 Office Action dated Dec. 12, 2019.
U.S. Appl. No. 16/562,206 Office Action dated May 11, 2020.
Xian et al.: Syndecans as receptors and organizers of the extracellular matrix. Cell Tissue Res. 339:31-46 (2010).

* cited by examiner

One way anova p<0.0001

One way anova p<0.0001

One way anova p<0.01

One way anova p<0.01

SDC-2 EXOSOME COMPOSITIONS AND METHODS OF ISOLATION AND USE

CROSS-REFERENCE

The present application is the U.S. National Phase entry of International Application No. PCT/IB2017/000091, filed Jan. 13, 2017, which claims priority to U.S. Provisional Application Ser. No. 62/279,534, filed Jan. 15, 2016, the contents of which are hereby incorporated by reference in their entirety, U.S. Provisional Application Ser. No. 62/337, 752, filed May 17, 2016, the contents of which are hereby incorporated by reference in their entirety, and U.S. Provisional Application Ser. No. 62/384,651, filed Sep. 7, 2016, the contents of which are hereby incorporated by reference in their entirety.

BACKGROUND OF THE INVENTION

Mesenchymal stem cells, (e.g., mesenchymal stromal stem cells and stromal cells) have been shown to have therapeutic value in treating a variety of diseases. These cells have been found to associate with arterioles, sinusoidal endothelium and high endothelial venules in vivo, where they can control endothelial cell activation and the trafficking of immune cells from the vasculature into target tissues. In addition mesenchymal stem cells have been shown to have immunosuppressive and anti-inflammatory properties such as avoiding allogeneic rejection and of inhibition immune cells, such as natural killer cells, neutrophils, dendritic cells, monocyte/macrophages and lymphocytes. Furthermore, mesenchymal stem cells have been found to produce immunosuppressing cytokines such as hepatocyte growth factor (HGF), IL-10, TGFβ1, cyclooxygenase 1 and 2, Syndecan-2 and PGE-2. The immunosuppressive activity of mesenchymal stem cells has been found to be increased in the presence of inflammatory stimuli, specifically interferon-gamma. These properties make mesenchymal stem cells and derivatives thereof (e.g., mesenchymal stromal stem cells, stromal cells, and exosomes produced by mesenchymal stem cells) particularly intriguing in their potential to treat disease.

SUMMARY OF THE INVENTION

Disclosed herein are exosome compositions, methods of isolation, and methods of use. In some exemplary embodiments the exosome compositions are MSC-derived exosome compositions. In some embodiments, there is provided a composition comprising exosomes, for example, in vitro exosomes or isolated exosomes, wherein at least 20% of the exosomes comprise SDC2. In some aspects, the SDC2 is an exosome surface constituent. In some aspects, the SDC2 is an exosome interior constituent. In some aspects, the composition comprises a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition does not comprise a living cell. In some aspects, the composition is non-tumorigenic. In some aspects, the composition is stable for over 48 hours without cryopreservation. In some aspects, the composition comprises SDC2+ mesenchymal stem cells. In some aspects, the composition comprises SDC2+ mesenchymal stromal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition comprises CD25+CD4+Foxp3+ regulatory T cells and SDC2+ mesenchymal stem cells. In some aspects, the composition comprises CD25+CD4+Foxp3+ regulatory T cells and SDC2+ mesenchymal stromal stem cells. In some aspects, the composition is frozen. In some aspects, the composition is lyophilized. In some aspects, the composition comprises an excipient. In some aspects, the excipient comprises at least one of sucrose, trehalose, polyethylene glycol, a polysaccharide, a carrier protein, and an inert protein. In some aspects, the excipient comprises at least one of dextran, hydroxyl ethyl starch (HETA), PEG-4000 and gelatin. In some aspects, the excipient comprises at least one of PLGA and Eudragit RS 100 Nanoparticles. In some aspects, the composition comprises a therapeutically effective amount of exosomes. In some aspects, the composition comprises at least $10^6$ exosomes. In some aspects, the composition comprises at least $10^7$ exosomes. In some aspects, the composition comprises at least $10^8$ exosomes. In some aspects, the composition comprises at least 1 μg of exosomes. In some aspects, the composition comprises at least 10 μg of exosomes. In some aspects, the composition comprises at least 20 μg of exosomes. In some aspects, the composition comprises at least 50 μg of exosomes. In some aspects, the composition comprises at least 100 μg of exosomes. In some aspects, the composition comprises at least 150 μg of exosomes. In some aspects, the composition comprises at least 200 μg of exosomes. In some aspects, the composition comprises at least 250 μg of exosomes. In some aspects, the composition comprises at least 500 μg of exosomes. In some aspects, the composition comprises at least 750 μg of exosomes. In some aspects, the composition comprises at least 1 mg of exosomes. In some aspects, the composition comprises at least 2 mg of exosomes. In some aspects, the composition comprises at least 3 mg of exosomes. In some aspects, the composition comprises at least 4 mg of exosomes. In some aspects, the composition comprises at least 5 mg of exosomes. In some aspects, the composition comprises at least 6 mg of exosomes. In some aspects, the composition comprises at least 7 mg of exosomes. In some aspects, the composition comprises at least 100 mg of exosomes. In some aspects, the composition comprises at least 200 mg of exosomes. In some aspects, the composition comprises at least 300 mg of exosomes. In some aspects, the composition comprises at least 400 mg of exosomes. In some aspects, the composition comprises at least 500 mg of exosomes. In some aspects, the composition comprises at least 600 mg of exosomes. In some aspects, the composition comprises at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the immunosuppressive drug comprises an anti-TNF antibody. In some aspects, the immunosuppressive drug comprises a TNF inhibitor. In some aspects, the immunosuppressive drug comprises an NSAID. In some aspects, the immunosuppressive drug comprises a steroid. In some aspects, the exosomes are purified. In some aspects, the exosomes are isolated. In some aspects, the exosomes are in vitro. In some aspects, the exosomes are paracrine-signaling exosomes. In some aspects, the exosomes are capable of crossing the blood brain barrier.

In some embodiments, there are provided methods of treating at least one symptom of diabetes in a subject comprising delivering a composition comprising purified SDC2+ exosomes to the subject. In some aspects, the diabetes is selected from type 1 diabetes and type 2 diabetes. In some aspects, the exosomes are paracrine signaling exosomes. In some aspects, delivering comprises injecting the composition comprising purified SDC2+ exosomes. In some aspects, the injecting is selected from at least one of intravenous injecting, lymph node injecting, subcutaneous injecting, intra-peritoneal injecting, and intramuscular injecting. In some aspects, the injecting is intravenous injecting. In some aspects, at least one of said purified SDC2+ exosomes contains an antigen, and wherein said antigen is not exposed to a recipient's humoral immune system. In some aspects, at least 20% of the exosomes comprise SDC2. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition comprises SDC2+ mesenchymal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition is frozen. In some aspects, the composition is lyophilized. In some aspects, the method comprises delivering a therapeutically effective amount of exosomes. In some aspects, the method comprises delivering at least $10^6$ exosomes. In some aspects, the method comprises delivering at least $10^7$ exosomes. In some aspects, the method comprises delivering at least $10^8$ exosomes. In some aspects, the method comprises delivering at least 1 µg of exosomes. In some aspects, the method comprises delivering at least 10 µg of exosomes. In some aspects, the method comprises delivering at least 20 µg of exosomes. In some aspects, the method comprises delivering at least 50 µg of exosomes. In some aspects, the method comprises delivering at least 100 µg of exosomes. In some aspects, the method comprises delivering at least 150 µg of exosomes. In some aspects, the method comprises delivering at least 200 µg of exosomes. In some aspects, the method comprises delivering at least 250 µg of exosomes. In some aspects, the method comprises delivering at least 500 µg of exosomes. In some aspects, the method comprises delivering at least 750 µg of exosomes. In some aspects, the method comprises delivering at least 1 mg of exosomes. In some aspects, the method comprises delivering at least 2 mg of exosomes. In some aspects, the method comprises delivering at least 3 mg of exosomes. In some aspects, the method comprises delivering at least 4 mg of exosomes. In some aspects, the method comprises delivering at least 5 mg of exosomes. In some aspects, the method comprises delivering at least 6 mg of exosomes. In some aspects, the method comprises delivering at least 7 mg of exosomes. In some aspects, the method comprises delivering at least 100 mg of exosomes. In some aspects, the method comprises delivering at least 200 mg of exosomes. In some aspects, the method comprises delivering at least 300 mg of exosomes. In some aspects, the method comprises delivering at least 400 mg of exosomes. In some aspects, the method comprises delivering at least 500 mg of exosomes. In some aspects, the method comprises delivering at least 600 mg of exosomes. In some aspects, the method comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the method reduces need for insulin in the subject. In some aspects, the method increases insulin sensitivity in the subject. In some aspects, the method reduces inflammation in the subject.

In some embodiments, there are provided compositions comprising purified SDC2+ exosomes for use in treating at least one symptom of diabetes in a subject. In some aspects, the diabetes is selected from type 1 diabetes and type 2 diabetes. In some aspects, the exosomes are paracrine signaling exosomes. In some aspects, delivering comprises injecting the composition comprising purified SDC2+ exosomes. In some aspects, the injecting is selected from at least one of intravenous injecting, lymph node injecting, subcutaneous injecting, intra-peritoneal injecting, and intramuscular injecting. In some aspects, the injecting is intravenous injecting. In some aspects, at least one of said purified SDC2+ exosomes contains an antigen, and wherein said antigen is not exposed to a recipient's humoral immune system. In some aspects, at least 20% of the exosomes comprise SDC2. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition comprises SDC2+ mesenchymal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition is frozen. In some aspects, the composition is lyophilized. In some aspects, the treatment comprises delivering a therapeutically effective amount of exosomes. In some aspects, the treatment comprises delivering at least 10^6 exosomes. In some aspects, the treatment comprises delivering at least 10^7 exosomes. In some aspects, the treatment comprises delivering at least 10^8 exosomes. In some aspects, the treatment comprises delivering at least 1 µg of exosomes. In some aspects, the treatment comprises delivering at least 10 µg of exosomes. In some aspects, the treatment comprises delivering at least 20 µg of exosomes. In some aspects, the treatment comprises delivering at least 50 µg of exosomes. In some aspects, the treatment comprises delivering at least 100 µg of exosomes. In some aspects, the treatment comprises delivering at least 150 µg of exosomes. In some aspects, the treatment comprises delivering at least 200 µg of exosomes. In some aspects, the treatment comprises delivering at least 250 µg of exosomes. In some aspects, the treatment comprises delivering at least 500 µg of exosomes. In some aspects, the treatment comprises delivering at least 750 µg of exosomes. In some aspects, the treatment comprises delivering at least 1 mg of exosomes. In some aspects, the treatment comprises delivering at least 2 mg of exosomes. In some aspects, the treatment comprises delivering at least 3 mg of exosomes. In some aspects, the treatment comprises delivering at least 4 mg of exosomes. In some aspects, the treatment comprises delivering at least 5 mg of exosomes. In some aspects, the treatment comprises delivering at least 6 mg of exosomes. In some aspects, the treatment comprises delivering at least 7 mg of exosomes. In some aspects, the treatment comprises delivering at least 100 mg of exosomes. In some aspects, the treatment comprises delivering at least 200 mg of exosomes. In some aspects, the treatment comprises delivering at least 300 mg of exosomes. In some aspects, the treatment comprises delivering at least 400 mg of exosomes. In some aspects, the treatment comprises delivering at least 500 mg of exosomes. In some aspects, the treatment comprises delivering at least 600 mg of exosomes. In some aspects, the treatment comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the treatment reduces need for insulin in the subject. In some aspects, the treatment increases insulin sensitivity in the subject. In some aspects, the method reduces inflammation in the subject.

In some embodiments, there are provided compositions comprising purified SDC2+ exosomes for use in preparation of a medicament for treating at least one symptom of diabetes in a subject. In some aspects, the diabetes is selected from type 1 diabetes and type 2 diabetes. In some aspects, the exosomes are paracrine signaling exosomes. In some aspects, delivering comprises injecting the composition comprising purified SDC2+ exosomes. In some aspects, the injecting is selected from at least one of intravenous injecting, lymph node injecting, subcutaneous injecting, intra-peritoneal injecting, and intramuscular injecting. In some aspects, the injecting is intravenous injecting. In some aspects, at least one of said purified SDC2+ exosomes contains an antigen, and wherein said antigen is not exposed to a recipient's humoral immune system. In some aspects, at least 20% of the exosomes comprise SDC2. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition comprises SDC2+ mesenchymal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition is frozen. In some aspects, the composition is lyophilized. In some aspects, the treatment comprises delivering a therapeutically effective amount of exosomes. In some aspects, the treatment comprises delivering at least 10^6 exosomes. In some aspects, the treatment comprises delivering at least 10^7 exosomes. In some aspects, the treatment comprises delivering at least 10^8 exosomes. In some aspects, the treatment comprises delivering at least 1 µg of exosomes. In some aspects, the treatment comprises delivering at least 10 µg of exosomes. In some aspects, the treatment comprises delivering at least 20 µg of exosomes. In some aspects, the treatment comprises delivering at least 50 µg of exosomes. In some aspects, the treatment comprises delivering at least 100 µg of exosomes. In some aspects, the treatment comprises delivering at least 150 µg of exosomes. In some aspects, the treatment comprises delivering at least 200 µg of exosomes. In some aspects, the treatment comprises delivering at least 250 µg of exosomes. In some aspects, the treatment comprises delivering at least 500 µg of exosomes. In some aspects, the treatment comprises delivering at least 750 µg of exosomes. In some aspects, the treatment comprises delivering at least 1 mg of exosomes. In some aspects, the treatment comprises delivering at least 2 mg of exosomes. In some aspects, the treatment comprises delivering at least 3 mg of exosomes. In some aspects, the treatment comprises delivering at least 4 mg of exosomes. In some aspects, the treatment comprises delivering at least 5 mg of exosomes. In some aspects, the treatment comprises delivering at least 6 mg of exosomes. In some aspects, the treatment comprises delivering at least 7 mg of exosomes. In some aspects, the treatment comprises delivering at least 100 mg of exosomes. In some aspects, the treatment comprises delivering at least 200 mg of exosomes. In some aspects, the treatment comprises delivering at least 300 mg of exosomes. In some aspects, the treatment comprises delivering at least 400 mg of exosomes. In some aspects, the treatment comprises delivering at least 500 mg of exosomes. In some aspects, the treatment comprises delivering at least 600 mg of exosomes. In some aspects, the treatment comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the treatment reduces need for insulin in the subject. In some aspects, the treatment increases insulin sensitivity in the subject. In some aspects, the method reduces inflammation in the subject.

In some embodiments, there are provided, methods of modulating an inflammation response in a mammal comprising delivering a composition comprising purified SDC2+ exosomes to a site of the inflammation response. In some aspects, the exosomes are paracrine-signaling exosomes. In some aspects, said delivering comprises injecting said composition comprising purified SDC2+ exosomes. In some aspects, said delivering comprises topically applying said composition comprising purified SDC2+ exosomes. In some aspects, said composition comprises a hydrogel or collagen gel. In some aspects, said delivering comprises intraocularly administering said composition comprising purified SDC2+ exosomes. In some aspects, said delivering comprises ophthalmic application of said composition comprising purified SDC2+ exosomes. In some aspects, said delivering comprises intravenous delivery of said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises intra-peritoneal delivery of said composition comprising purified SDC2+ exosomes. In some aspects, said delivering comprises intrathecal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, delivering comprises direct cardiac administration. In some aspects, the exosomes cross the blood brain barrier. In some aspects, at least one of said purified SDC2+ exosomes contains an antigen, and wherein said antigen is not exposed to a recipient's humoral immune system. In some aspects, at least 20% of the exosomes comprises SDC2. In some aspects, the composition comprises a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition does not comprise a living cell. In some aspects, the composition comprises SDC2+ mesenchymal stem cells. In some aspects, the composition comprises SDC2+ mesenchymal stromal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition comprises CD25+CD4+Foxp3+ regulatory T cells and SDC2+ mesenchymal stem cells. In some aspects, the composition comprises CD25+CD4+Foxp3+ regulatory T cells and SDC2+ mesenchymal stromal stem cells. In some aspects, the composition is frozen. In some aspects, the composition is lyophilized. In some aspects, the method comprises delivering at least $10^6$ exosomes. In some aspects, the method comprises delivering a therapeutically effective amount of exosomes. In some aspects, the method comprises delivering at least $10^6$ exosomes. In some aspects, the method comprises delivering at least $10^7$ exosomes. In some aspects, the method comprises delivering at least $10^8$ exosomes. In some aspects, the method comprises delivering at least 1 µg of exosomes. In some aspects, the method comprises delivering at least 10 µg of exosomes. In some aspects, the method comprises delivering at least 20 µg of exosomes. In some aspects, the method comprises delivering at least 50 µg of exosomes. In some aspects, the method comprises delivering at least 100 µg of exosomes. In some aspects, the method comprises delivering at least 150 µg of exosomes. In some aspects, the method comprises delivering at least 200 µg of exosomes. In some aspects, the method comprises delivering at least 250 µg of exosomes. In some aspects, the method comprises delivering at least 500 µg of exosomes. In some aspects, the method comprises delivering at least 750 µg of exosomes. In some aspects, the method comprises delivering at least 1 mg of exosomes. In some aspects, the method comprises delivering at least 2 mg of exosomes. In some aspects, the method comprises delivering at least 3 mg of exosomes. In some aspects, the method comprises delivering at least 4 mg of exosomes. In some aspects, the method comprises delivering at least 5 mg of exosomes. In some aspects, the method comprises delivering at least 6 mg of exosomes. In some aspects, the method comprises delivering at least 7 mg of exosomes. In some aspects, the method comprises delivering at least 100 mg of exosomes. In some aspects, the method comprises delivering at least 200 mg of exosomes. In some aspects, the method comprises delivering at least 300 mg of exosomes. In some aspects, the method comprises delivering at least 400 mg of exosomes. In some aspects, the method comprises delivering at least 500 mg of exosomes. In some aspects, the method comprises delivering at least 600 mg of exosomes. In some aspects, the method comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the immunosuppressive drug comprises an anti-TNF antibody. In some aspects, the immunosuppressive drug comprises a TNF inhibitor. In some aspects, the immunosuppressive drug comprises an NSAID. In some aspects, the immunosuppressive drug comprises a steroid. In some aspects, the inflammation response comprises an immune response. In some aspects, the immune response comprises an autoimmune response. In some aspects, the immune response comprises at least one of type 1 diabetes, type 2 diabetes, sepsis, Crohn's disease, inflammatory bowel syndrome, rheumatoid arthritis, and graft-host disease. In some aspects, the inflammation response comprises at least one of Alzheimer's disease, Parkinson's disease, multiple sclerosis, ALS, and a motor neuron disorder. In some aspects, the inflammation response comprises at least one of a dermal wound, a bone fracture, a concussion wound, and a burn. In some aspects, the inflammation response comprises a diabetic complication. In some aspects, the diabetic complication comprises at least one of atherosclerosis, nephropathy, cardiomyopathy, neuropathy, a kidney disorder, kidney failure, a diabetic ulcer, and a leg ulcer. In some aspects, the inflammation response comprises at least one of ARDS, sepsis, or septic shock. In some aspects, the inflammation response comprises at least one of osteoarthritis and a bone fracture. In some aspects, the inflammation response comprises an inflammatory liver disease. In some aspects, the inflammation response comprises a heart disorder. In some aspects, the heart disorder comprises at least one of Myocarditis, Postmyocardial infarction syndrome, Postpericardiotomy syndrome, and Sub acute bacterial endocarditis. In some aspects, the inflammation response comprises a kidney disorder. In some aspects, the kidney disorder comprises at least one of Anti-Glomerular Basement Membrane nephritis, Interstitial cystitis, and Lupus nephritis. In some aspects, the inflammation response comprises a liver disorder. In some aspects, the liver disorder comprises at least one of autoimmune hepatitis, Primary biliary cirrhosis, and Primary sclerosing cholangitis. In some aspects, the inflammation response comprises a lung disorder. In some aspects, the inflammation response comprises at least one of ARDS, Antisynthetase syndrome, asthma, chronic obstructive pulmonary disease, cystic fibrosis, atelectasis, bronchitis, emphysema, pneumonia, and pulmonary edema. In some aspects, the inflammation response comprises a skin disorder. In some aspects, the skin disorder comprises at least one of Alopecia Areata, Autoimmune Angioedema, autoimmune progesterone dermatitis, autoimmune urticaria, Bullous pemphigoid, Cicatricial pemphigoid, Dermatitis herpetiformis, Discoid lupus erythematosus, *Epidermolysis bullosa acquisita, Erythema nodosum, Gestational pemphigoid, Hidradenitis suppurativa, Lichen planus, Lichen sclerosus,* Linear IgA disease, *Morphea, Pemphigus vulgaris, Pityriasis lichenoides* et *varioliformis acuta,* Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. In some aspects, the inflammation response comprises a pancreas disorder. In some aspects, the pancreas disorder comprises at least one of, autoimmune pancreatitis and Diabetes mellitus type 1. In some aspects, the inflammation response comprises a thyroid disorder. In some aspects, the thyroid disorder comprises at least one of autoimmune thyroiditis, Ord's thyroiditis and Graves' disease. In some aspects, the inflammation response comprises an exocrine disorder. In some aspects, the exocrine disorder comprises at least one of a Reproductive Organ disorder, autoimmune oophoritis, Endometriosis, and autoimmune orchitis. In some aspects, the inflammation response comprises a salivary gland disorder. In some aspects, the inflammation response comprises Sjogren's syndrome. In some aspects, the inflammation response comprises a digestive system disorder. In some aspects, the digestive system disorder comprises at least one of autoimmune enteropathy, Celiac disease, Crohn's disease, Microscopic colitis, and Ulcerative colitis. In some aspects, the inflammation response comprises a blood disorder. In some aspects, the blood disorder comprises at least one of Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. In some aspects, the inflammation response comprises a connective tissue, multiorgan or systemic disorder. In some aspects, the disorder comprises at least one of Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, and Undifferentiated connective tissue disease. In some aspects, the inflammation response comprises a muscle disorder. In some aspects, the inflammation response comprises cachexia. In some aspects, the inflammation response comprises sarcophenia. In some aspects, the inflammation response comprises at least one of Dermatomyositis, Fibromyalgia, Inclusion body myositis, Myositis, Myasthenia gravis, Neuromyotonia, Paraneoplastic cerebellar degeneration, and Polymyositis. In some aspects, the inflammation response comprises a nervous system disorder. In some aspects, the nervous system disorder comprises at least one of Acute disseminated encephalomyelitis, Acute motor axonal neuropathy, Anti-N-Methyl-D-Aspartate Receptor Encephalitis, Balo concentric sclerosis, Bickerstaffs encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, and Transverse myelitis. In some aspects, the inflammation response comprises an eye disorder. In some aspects, the eye disorder comprises at least one of autoimmune retinopathy, autoimmune uveitis, Cogan syndrome, Graves's ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. In some aspects, the inflammation response comprises an ear disorder. In some aspects, the ear disorder comprises at least one of autoimmune inner ear disease and Meniere's disease. In some aspects, the inflammation response comprises a vascular system disorder. In some aspects, the vascular system disorder comprises at least one of Anti-neutrophil cytoplasmic antibody-associated vasculitis, Behcet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, *Polyarteritis nodosa*, Polymyalgia rheumatica, Urticarial vasculitis, and Vasculitis. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

In some embodiments, there are provided, compositions comprising purified SDC2+ exosomes for use in modulating an inflammation response in a mammal comprising delivering the composition to a site of the inflammation response. In some aspects, the exosomes are paracrine-signaling exosomes. In some aspects, said delivering comprises injecting said composition comprising purified SDC2+ exosomes. In some aspects, said delivering comprises topically applying said composition comprising purified SDC2+ exosomes. In some aspects, said composition comprises a hydrogel or collagen gel. In some aspects, said delivering comprises intraocularly administering said composition comprising purified SDC2+ exosomes. In some aspects, said delivering comprises ophthalmic application of said composition comprising purified SDC2+ exosomes. In some aspects, said delivering comprises intravenous delivery of said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises intra-peritoneal delivery of said composition comprising purified SDC2+ exosomes. In some aspects, said delivering comprises intrathecal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, delivering comprises direct cardiac administration. In some aspects, the exosomes cross the blood brain barrier. In some aspects, at least one of said purified SDC2+ exosomes contains an antigen, and wherein said antigen is not exposed to a recipient's humoral immune system. In some aspects, at least 20% of the exosomes comprises SDC2. In some aspects, the composition comprises a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition does not comprise a living cell. In some aspects, the composition comprises SDC2+ mesenchymal stem cells. In some aspects, the composition comprises SDC2+ mesenchymal stromal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+CD4+Foxp3+ regulatory T cells. In some aspects, the composition comprises CD25+CD4+Foxp3+ regulatory T cells and SDC2+ mesenchymal stem cells. In some aspects, the composition comprises CD25+CD4+Foxp3+ regulatory T cells and SDC2+ mesenchymal stromal stem cells. In some aspects, the composition is frozen. In some aspects, the composition is lyophilized. In some aspects, the modulating comprises delivering at least $10^6$ exosomes. In some aspects, the modulating comprises delivering a therapeutically effective amount of exosomes. In some aspects, the modulating comprises delivering at least $10^6$ exosomes. In some aspects, the modulating comprises delivering at least $10^7$ exosomes. In some aspects, the modulating comprises delivering at least $10^8$ exosomes. In some aspects, the modulating comprises delivering at least 1 μg of exosomes. In some aspects, the modulating comprises delivering at least 10 μg of exosomes. In some aspects, the modulating comprises delivering at least 20 μg of exosomes. In some aspects, the modulating comprises delivering at least 50 μg of exosomes. In some aspects, the modulating comprises delivering at least 100 μg of exosomes. In some aspects, the modulating comprises delivering at least 150 μg of exosomes. In some aspects, the modulating comprises delivering at least 200 μg of exosomes. In some aspects, the modulating comprises delivering at least 250 μg of exosomes. In some aspects, the modulating comprises delivering at least 500 μg of exosomes. In some aspects, the modulating comprises delivering at least 750 μg of exosomes. In some aspects, the modulating comprises delivering at least 1 mg of exosomes. In some aspects, the modulating comprises delivering at least 2 mg of exosomes. In some aspects, the modulating comprises delivering at least 3 mg of exosomes. In some aspects, the modulating comprises delivering at least 4 mg of exosomes. In some aspects, the modulating comprises delivering at least 5 mg of exosomes. In some aspects, the modulating comprises delivering at least 6 mg of exosomes. In some aspects, the modulating comprises delivering at least 7 mg of exosomes. In some aspects, the modulating comprises delivering at least 100 mg of exosomes. In some aspects, the modulating comprises delivering at least 200 mg of exosomes. In some aspects, the modulating comprises delivering at least 300 mg of exosomes. In some aspects, the modulating comprises delivering at least 400 mg of exosomes. In some aspects, the modulating comprises delivering at least 500 mg of exosomes. In some aspects, the modulating comprises delivering at least 600 mg of exosomes. In some aspects, the modulating comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the immunosuppressive drug comprises an anti-TNF antibody. In some aspects, the immunosuppressive drug comprises a TNF inhibitor. In some aspects, the immunosuppressive drug comprises an NSAID. In some aspects, the immunosuppressive drug comprises a steroid. In some aspects, the inflammation response comprises an immune response. In some aspects, the immune response comprises an autoimmune response. In some aspects, the immune response comprises at least one of type 1 diabetes, type 2 diabetes, sepsis, Crohn's disease, inflammatory bowel syndrome, rheumatoid arthritis, and graft-host disease. In some aspects, the inflammation response comprises at least one of Alzheimer's disease, Parkinson's disease, multiple sclerosis, ALS, and a motor neuron disorder. In some aspects, the inflammation response comprises at least one of a dermal wound, a bone fracture, a concussion wound, and a burn. In some aspects, the inflammation response comprises a diabetic complication. In some aspects, the diabetic complication comprises at least one of atherosclerosis, nephropathy, cardiomyopathy, neuropathy, a kidney disorder, kidney failure, a diabetic ulcer, and a leg ulcer. In some aspects, the inflammation response comprises at least one of ARDS, sepsis, or septic shock. In some aspects, the inflammation response comprises at least one of osteoarthritis and a bone fracture. In some aspects, the inflammation response comprises an inflammatory liver disease. In some aspects, the inflammation response comprises a heart disorder. In some aspects, the heart disorder comprises at least one of Myocarditis, Postmyocardial infarction syndrome, Postpericardiotomy syndrome, and Sub acute bacterial endocarditis. In some aspects, the inflammation response comprises a kidney disorder. In some aspects, the kidney disorder comprises at least one of Anti-Glomerular Basement Membrane nephritis, Interstitial cystitis, and Lupus nephritis. In some aspects, the inflammation response comprises a liver disorder. In some aspects, the liver disorder comprises at least one of autoimmune hepatitis, Primary biliary cirrhosis, and Primary sclerosing cholangitis. In some aspects, the inflammation response comprises a lung disorder. In some aspects, the inflammation response comprises at least one of ARDS, Antisynthetase syndrome, asthma, chronic obstructive pulmonary disease, cystic fibrosis, atelectasis, bronchitis, emphysema, pneumonia, and pulmonary edema. In some aspects, the inflammation response comprises a skin disorder. In some aspects, the skin disorder comprises at least one of Alopecia Areata, Autoimmune Angioedema, autoimmune progesterone dermatitis, autoimmune urticaria, Bullous pemphigoid, Cicatricial pemphigoid, Dermatitis herpetiformis, Discoid lupus erythematosus, *Epidermolysis bullosa acquisita, Erythema nodosum, Gestational pemphigoid, Hidradenitis suppurativa, Lichen planus, Lichen sclerosus*, Linear IgA disease, *Morphea, Pemphigus vulgaris, Pityriasis lichenoides* et *varioliformis acuta*, Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. In some aspects, the inflammation response comprises a pancreas disorder. In some aspects, the pancreas disorder comprises at least one of, autoimmune pancreatitis and Diabetes mellitus type 1. In some aspects, the inflammation response comprises a thyroid disorder. In some aspects, the thyroid disorder comprises at least one of autoimmune thyroiditis, Ord's thyroiditis and Graves' disease. In some aspects, the inflammation response comprises an exocrine disorder. In some aspects, the exocrine disorder comprises at least one of a Reproductive Organ disorder, autoimmune oophoritis, Endometriosis, and autoimmune orchitis. In some aspects, the inflammation response comprises a salivary gland disorder. In some aspects, the inflammation response comprises Sjogren's syndrome. In some aspects, the inflammation response comprises a digestive system disorder. In some aspects, the digestive system disorder comprises at least one of autoimmune enteropathy, Celiac disease, Crohn's disease, Microscopic colitis, and Ulcerative colitis. In some aspects, the inflammation response comprises a blood disorder. In some aspects, the blood disorder comprises at least one of Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. In some aspects, the inflammation response comprises a connective tissue, multi-organ or systemic disorder. In some aspects, the disorder comprises at least one of Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, and Undifferentiated connective tissue disease. In some aspects, the inflammation response comprises a muscle disorder. In some aspects, the inflammation response comprises cachexia. In some aspects, the inflammation response comprises sarcophenia. In some aspects, the inflammation response comprises at least one of Dermatomyositis, Fibromyalgia, Inclusion body myositis, Myositis, Myasthenia gravis, Neuromyotonia, Paraneoplastic cerebellar degeneration, and Polymyositis. In some aspects, the inflammation response comprises a nervous system disorder. In some aspects, the nervous system disorder comprises at least one of Acute disseminated encephalomyelitis, Acute motor axonal neuropathy, Anti-N-Methyl-D-Aspartate Receptor Encephalitis, Balo concentric sclerosis, Bickerstaffs encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, and Transverse myelitis. In some aspects, the inflammation response comprises an eye disorder. In some aspects, the eye disorder comprises at least one of autoimmune retinopathy, autoimmune uveitis, Cogan syndrome, Graves's ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. In some aspects, the inflammation response comprises an ear disorder. In some aspects, the ear disorder comprises at least one of autoimmune inner ear disease and Meniere's disease. In some aspects, the inflammation response comprises a vascular system disorder. In some aspects, the vascular system disorder comprises at least one of Anti-neutrophil cytoplasmic antibody-associated vasculitis, Behcet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, *Polyarteritis nodosa*, Polymyalgia rheumatica, Urticarial vasculitis, and Vasculitis. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

In some embodiments, there are provided, compositions comprising purified SDC2+ exosomes for use in preparation of a medicament for modulating an inflammation response in a mammal comprising delivering the composition to a site of the inflammation response. In some aspects, the exosomes are paracrine-signaling exosomes. In some aspects, said delivering comprises injecting said composition comprising purified SDC2+ exosomes. In some aspects, said delivering comprises topically applying said composition comprising purified SDC2+ exosomes. In some aspects, said composition comprises a hydrogel or collagen gel. In some aspects, said delivering comprises intraocularly administering said composition comprising purified SDC2+ exosomes. In some aspects, said delivering comprises ophthalmic application of said composition comprising purified SDC2+ exosomes. In some aspects, said delivering comprises intravenous delivery of said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises intra-peritoneal delivery of said composition comprising purified SDC2+ exosomes. In some aspects, said delivering comprises intrathecal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, delivering comprises direct cardiac administration. In some aspects, the exosomes cross the blood brain barrier. In some aspects, at least one of said purified SDC2+ exosomes contains an antigen, and wherein said antigen is not exposed to a recipient's humoral immune system. In some aspects, at least 20% of the exosomes comprises SDC2. In some aspects, the composition comprises a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45–. In some aspects, the composition does not comprise a living cell. In some aspects, the composition comprises SDC2+ mesenchymal stem cells. In some aspects, the composition comprises SDC2+ mesenchymal stromal stem cells. In some aspects, the composition comprises CD25+ regulatory T cells. In some aspects, the composition comprises CD4+ regulatory T cells. In some aspects, the composition comprises Foxp3+ regulatory T cells. In some aspects, the composition comprises CD25+ CD4+Foxp3+ regulatory T cells. In some aspects, the composition comprises CD25+CD4+Foxp3+ regulatory T cells and SDC2+ mesenchymal stem cells. In some aspects, the composition comprises CD25+CD4+Foxp3+ regulatory T cells and SDC2+ mesenchymal stromal stem cells. In some aspects, the composition is frozen. In some aspects, the composition is lyophilized. In some aspects, the modulating comprises delivering at least 10^6 exosomes. In some aspects, the modulating comprises delivering a therapeutically effective amount of exosomes. In some aspects, the modulating comprises delivering at least 10^6 exosomes. In some aspects, the modulating comprises delivering at least 10^7 exosomes. In some aspects, the modulating comprises delivering at least 10^8 exosomes. In some aspects, the modulating comprises delivering at least 1 µg of exosomes. In some aspects, the modulating comprises delivering at least 10 µg of exosomes. In some aspects, the modulating comprises delivering at least 20 µg of exosomes. In some aspects, the modulating comprises delivering at least 50 µg of exosomes. In some aspects, the modulating comprises delivering at least 100 µg of exosomes. In some aspects, the modulating comprises delivering at least 150 µg of exosomes. In some aspects, the modulating comprises delivering at least 200 µg of exosomes. In some aspects, the modulating comprises delivering at least 250 µg of exosomes. In some aspects, the modulating comprises delivering at least 500 g of exosomes. In some aspects, the modulating comprises delivering at least 750 µg of exosomes. In some aspects, the modulating comprises delivering at least 1 mg of exosomes. In some aspects, the modulating comprises delivering at least 2 mg of exosomes. In some aspects, the modulating comprises delivering at least 3 mg of exosomes. In some aspects, the modulating comprises delivering at least 4 mg of exosomes. In some aspects, the modulating comprises delivering at least 5 mg of exosomes. In some aspects, the modulating comprises delivering at least 6 mg of exosomes. In some aspects, the modulating comprises delivering at least 7 mg of exosomes. In some aspects, the modulating comprises delivering at least 100 mg of exosomes. In some aspects, the modulating comprises delivering at least 200 mg of exosomes. In some aspects, the modulating comprises delivering at least 300 mg of exosomes. In some aspects, the modulating comprises delivering at least 400 mg of exosomes. In some aspects, the modulating comprises delivering at least 500 mg of exosomes. In some aspects, the modulating comprises delivering at least 600 mg of exosomes. In some aspects, the modulating comprises delivering at least 700 mg of exosomes. In some aspects, the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the immunosuppressive drug comprises an anti-TNF antibody. In some aspects, the immunosuppressive drug comprises a TNF inhibitor. In some aspects, the immunosuppressive drug comprises an NSAID. In some aspects, the immunosuppressive drug comprises a steroid. In some aspects, the inflammation response comprises an immune response. In some aspects, the immune response comprises an autoimmune response. In some aspects, the immune response comprises at least one of type 1 diabetes, type 2 diabetes, sepsis, Crohn's disease, inflammatory bowel syndrome, rheumatoid arthritis, and graft-host disease. In some aspects, the inflammation response comprises at least one of Alzheimer's disease, Parkinson's disease, multiple sclerosis, ALS, and a motor neuron disorder. In some aspects, the inflammation response comprises at least one of a dermal wound, a bone fracture, a concussion wound, and a burn. In some aspects, the inflammation response comprises a diabetic complication. In some aspects, the diabetic complication comprises at least one of atherosclerosis, nephropathy, cardiomyopathy, neuropathy, a kidney disorder, kidney failure, a diabetic ulcer, and a leg ulcer. In some aspects, the inflammation response comprises at least one of ARDS, sepsis, or septic shock. In some aspects, the inflammation response comprises at least one of osteoarthritis and a bone fracture. In some aspects, the inflammation response comprises an inflammatory liver disease. In some aspects, the inflammation response comprises a heart disorder. In some aspects, the heart disorder comprises at least one of Myocarditis, Postmyocardial infarction syndrome, Postpericardiotomy syndrome, and Sub acute bacterial endocarditis. In some aspects, the inflammation response comprises a kidney disorder. In some aspects, the kidney disorder comprises at least one of Anti-Glomerular Basement Membrane nephritis, Interstitial cystitis, and Lupus nephritis. In some aspects, the inflammation response comprises a liver disorder. In some aspects, the liver disorder comprises at least one of autoimmune hepatitis, Primary biliary cirrhosis, and Primary sclerosing cholangitis. In some aspects, the inflammation response comprises a lung disorder. In some aspects, the inflammation response comprises at least one of ARDS, Antisynthetase syndrome, asthma, chronic obstructive pulmonary disease, cystic fibrosis, atelectasis, bronchitis, emphysema, pneumonia, and pulmonary edema. In some aspects, the inflammation response comprises a skin disorder. In some aspects, the skin disorder comprises at least one of Alopecia Areata, Autoimmune Angioedema, autoimmune progesterone dermatitis, autoimmune urticaria, Bullous pemphigoid, Cicatricial pemphigoid, Dermatitis herpetiformis, Discoid lupus erythematosus, *Epidermolysis bullosa acquisita*, *Erythema nodosum*, *Gestational pemphigoid*, *Hidradenitis suppurativa*, *Lichen planus*, *Lichen sclerosus*, Linear IgA disease, *Morphea, Pemphigus vulgaris, Pityriasis lichenoides* et *varioliformis acuta*, Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. In some aspects, the inflammation response comprises a pancreas disorder. In some aspects, the pancreas disorder comprises at least one of, autoimmune pancreatitis and Diabetes mellitus type 1. In some aspects, the inflammation response comprises a thyroid disorder. In some aspects, the thyroid disorder comprises at least one of autoimmune thyroiditis, Ord's thyroiditis and Graves' disease. In some aspects, the inflammation response comprises an exocrine disorder. In some aspects, the exocrine disorder comprises at least one of a Reproductive Organ disorder, autoimmune oophoritis, Endometriosis, and autoimmune orchitis. In some aspects, the inflammation response comprises a salivary gland disorder. In some aspects, the inflammation response comprises Sjogren's syndrome. In some aspects, the inflammation response comprises a digestive system disorder. In some aspects, the digestive system disorder comprises at least one of autoimmune enteropathy, Celiac disease, Crohn's disease, Microscopic colitis, and Ulcerative colitis. In some aspects, the inflammation response comprises a blood disorder. In some aspects, the blood disorder comprises at least one of Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. In some aspects, the inflammation response comprises a connective tissue, multi-organ or systemic disorder. In some aspects, the disorder comprises at least one of Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, and Undifferentiated connective tissue disease. In some aspects, the inflammation response comprises a muscle disorder. In some aspects, the inflammation response comprises cachexia. In some aspects, the inflammation response comprises sarcophenia. In some aspects, the inflammation response comprises at least one of Dermatomyositis, Fibromyalgia, Inclusion body myositis, Myositis, Myasthenia gravis, Neuromyotonia, Paraneoplastic cerebellar degeneration, and Polymyositis. In some aspects, the inflammation response comprises a nervous system disorder. In some aspects, the nervous system disorder comprises at least one of Acute disseminated encephalomyelitis, Acute motor axonal neuropathy, Anti-N-Methyl-D-Aspartate Receptor Encephalitis, Balo concentric sclerosis, Bickerstaffs encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, and Transverse myelitis. In some aspects, the inflammation response comprises an eye disorder. In some aspects, the eye disorder comprises at least one of autoimmune retinopathy, autoimmune uveitis, Cogan syndrome, Graves's ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. In some aspects, the inflammation response comprises an ear disorder. In some aspects, the ear disorder comprises at least one of autoimmune inner ear disease and Meniere's disease. In some aspects, the inflammation response comprises a vascular system disorder. In some aspects, the vascular system disorder comprises at least one of Anti-neutrophil cytoplasmic antibody-associated vasculitis, Behcet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, *Polyarteritis nodosa*, Polymyalgia rheumatica, Urticarial vasculitis, and Vasculitis. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are methods of obtaining an immuno-modulatory composition comprising exosomes, comprising obtaining exosomes having SDC2 at a frequency of at least 20%. In some aspects, the exosomes are paracrine signaling exosomes. In some aspects, the SDC2 is an exosome surface constituent. In some aspects, the SDC2 is an exosome interior constituent. In some aspects, the exosomes having SDC2 at a frequency of at least 20% are derived from at least one SDC2+ stromal cell. In some aspects, the method comprises transforming the at least one SDC2+ stromal cell to overexpress SDC2/S2/CD362/fibroglycan. In some aspects, the method comprises irradiating the at least one SDC2+ stromal cell. In some aspects, the method comprises irradiating using gamma-irradiation. In some aspects, the method comprises subjecting the at least one SDC2+ stromal cell to inflammatory stimulation. In some aspects, the inflammatory stimulation comprises at least one of TNF-alpha, Interferon-gamma, Interferon-beta, Interleukin-1b, TLR agonists, Poly I:C, and LPS. In some aspects, the method comprises subjecting the at least one SDC2+ stromal cell to growth arrest. In some aspects, the growth arrest comprises at least one or gamma-irradiation, mitomycin-c, TGFb stimulation, and growing cells to confluence. In some aspects, the method comprises providing a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition does not comprise a living cell. In some aspects, the composition is non-tumorigenic. In some aspects, the composition is stable for over 48 hours without cryopreservation. In some aspects, the composition comprises SDC2+ mesenchymal stem cells. In some aspects, the composition comprises SDC2+ mesenchymal stromal stem cells. In some aspects, the composition is frozen. In some aspects, the composition is lyophilized. In some aspects, a therapeutically active amount of exosomes are obtained. In some aspects, at least $10^6$ exosomes are obtained. In some aspects, at least $10^7$ exosomes are obtained. In some aspects, at least $10^8$ exosomes are obtained. In some aspects, at least 1 µg of exosomes are obtained. In some aspects, at least 10 µg of exosomes are obtained. In some aspects, at least 20 µg of exosomes are obtained. In some aspects, at least 50 µg of exosomes are obtained. In some aspects, at least 100 µg of exosomes are obtained. In some aspects, at least 150 µg of exosomes are obtained. In some aspects, at least 200 µg of exosomes are obtained. In some aspects, at least 250 µg of exosomes are obtained. In some aspects, at least 500 µg of exosomes are obtained. In some aspects, at least 750 µg of exosomes are obtained. In some aspects, at least 1 mg of exosomes are obtained. In some aspects, at least 2 mg of exosomes are obtained. In some aspects, at least 3 mg of exosomes are obtained. In some aspects, at least 4 mg of exosomes are obtained. In some aspects, at least 5 mg of exosomes are obtained. In some aspects, at least 6 mg of exosomes are obtained. In some aspects, at least 7 mg of exosomes are obtained. In some aspects, at least 100 mg of exosomes are obtained. In some aspects, at least 200 mg of exosomes are obtained. In some aspects, at least 300 mg of exosomes are obtained. In some aspects, at least 400 mg of exosomes are obtained. In some aspects, at least 500 mg of exosomes are obtained. In some aspects, at least 600 mg of exosomes are obtained. In some aspects, at least 700 mg of exosomes are obtained. In some aspects, the exosomes are purified. In some aspects, the exosomes are isolated. In some aspects, the SDC2+ stromal cells are cultured in a hollow-fiber bioreactor. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprise microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are methods of isolating an immuno-modulatory composition comprising the steps of obtaining a composition comprising exosomes; contacting the composition to an anti-SDC2 antibody; and retaining exosomes bound to the anti-SDC2 antibody. In some aspects, the exosomes are paracrine signaling exosomes. In some aspects, the composition comprising exosomes is obtained from a cell culture comprising mesenchymal stem cells. In some aspects, the cell culture comprising mesenchymal stem cells comprises SDC2+ cells. In some aspects, the cell culture comprising mesenchymal stem cells comprises CD45− cells. In some aspects, the cell culture comprising mesenchymal stem cells comprises SDC2+ mesenchymal stem cells. In some aspects, the cell culture comprising mesenchymal stem cells is enriched for SDC2+ cells. In some aspects, the cell culture comprising mesenchymal stem cells is enriched for SDC2+ mesenchymal stem cells. In some aspects, retaining exosomes bound to the anti-SDC2 antibody comprises storage at room-temperature. In some aspects, retaining exosomes bound to the anti-SDC2 antibody comprises storage without cryogenic preservation. In some aspects, retaining exosomes bound to the anti-SDC2 antibody comprises freezing the exosomes.

Also provided herein are methods of isolating an immuno-modulatory composition comprising the steps of obtaining a cell population enriched for SDC2+ cells; recovering a supernatant from said cell population; and obtaining an exosome fraction from the supernatant. In some aspects, the exosomes are paracrine signaling exosomes. In some aspects, the SDC2+ cells comprise mesenchymal stem cells. In some aspects, the SDC2+ cells comprise mesenchymal stromal stem cells. In some aspects, the SDC2+ cells comprise CD45− cells. In some aspects, obtaining an exosome fraction comprises centrifuging the supernatant. In some aspects, the centrifugation comprises centrifuging the cells at about 100,000 g for at least 1 hr. In some aspects, the centrifugation comprises ultrafiltration. In some aspects, the centrifugation comprises size-exclusion liquid chromatography. In some aspects, obtaining an exosome fraction comprises ultrafiltration. In some aspects, obtaining an exosome fraction comprises size-exclusion liquid chromatography. In some aspects, obtaining an exosome fraction comprises contacting the supernatant to an anti-SDC2 antibody. In some aspects, the method comprises storing the exosome fraction at room-temperature. In some aspects, the method comprises storing the exosome fraction without cryogenic preservation. In some aspects, the method comprises adding an immunosuppressive drug to the immunomodulatory composition. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. In some aspects, the cell population enriched for SDC2+ cells is perturbed to elicit exosome production. In some aspects, the method comprises transforming the cell population enriched for SDC2+ cells to overexpress SDC2/S2/CD362/fibroglycan. In some aspects, the method comprises irradiating cell population enriched for SDC2+ cells. In some aspects, the method comprises irradiating using gamma-irradiation. In some aspects, the method comprises subjecting the cell population enriched for SDC2+ cells to inflammatory stimulation. In some aspects, the inflammatory stimulation comprises at least one of TNF-alpha, Interferon-gamma, Interferon-beta, Interleukin-1b, TLR agonists, Poly I:C, and LPS. In some aspects, the method comprises subjecting the cell population enriched for SDC2+ cells to growth arrest. In some aspects, the growth arrest comprises at least one or gamma-irradiation, mitomycin-c, TGFb stimulation, and growing cells to confluence. In some aspects, the cell population is cultured in a hollow-fiber bioreactor. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprise microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are methods of delivering an immuno-modulatory signal to an intracellular space of a mammal, comprising the steps of obtaining a population of exosomes from a SDC2+ mesenchymal stem cell; and administering the population of exosomes to the mammal; wherein the population of exosomes contains the immuno-modulatory signal; and wherein contents of the exosomes are delivered to an intracellular space of the mammal without eliciting a humoral immune response to the contents of the exosome in the mammal. In some aspects, the exosomes are paracrine signaling exosomes. In some aspects, the population of exosomes is drawn into an intracellular space of a mammal by phagocytosis. In some aspects, the population of exosomes is drawn into an intracellular space of a mammal by endocytosis. In some aspects, the population of exosomes is drawn into an intracellular space of a mammal by fusion. In some aspects, the administering comprises injecting the population into the mammal. In some aspects, the administering comprises topically applying said composition comprising purified SDC2+ exosomes. In some aspects, the administering comprises a hydrogel or collagen gel. In some aspects, the administering comprises intraocularly applying said composition comprising purified SDC2+ exosomes. In some aspects, the administering comprises ophthalmic application of said composition comprising purified SDC2+ exosomes. In some aspects, the administering comprises injecting said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises peritoneal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, the method comprises administering an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. In some aspects, the population of exosomes comprises an exosome containing at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the exosome protein constituent is not detected by the host humoral immune system. In some aspects, obtaining the population of exosomes comprises freezing the population of exosomes. In some aspects, obtaining the population of exosomes comprises storing the population of exosomes at room-temperature. In some aspects, obtaining the population of exosomes comprises storing the population of exosomes without cryogenic preservation. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs(miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are populations of exosomes for use in delivering an immuno-modulatory signal to an intracellular space of a mammal, comprising the steps of obtaining a population of exosomes from a SDC2+ mesenchymal stem cell; and administering the population of exosomes to the mammal; wherein the population of exosomes contains the immuno-modulatory signal; and wherein contents of the exosomes are delivered to an intracellular space of the mammal without eliciting a humoral immune response to the contents of the exosome in the mammal. In some aspects, the exosomes are paracrine signaling exosomes. In some aspects, the population of exosomes is drawn into an intracellular space of a mammal by phagocytosis. In some aspects, the population of exosomes is drawn into an intracellular space of a mammal by endocytosis. In some aspects, the population of exosomes is drawn into an intracellular space of a mammal by fusion. In some aspects, the administering comprises injecting the population into the mammal. In some aspects, the administering comprises topically applying said composition comprising purified SDC2+ exosomes. In some aspects, the administering comprises a hydrogel or collagen gel. In some aspects, the administering comprises intraocularly applying said composition comprising purified SDC2+ exosomes. In some aspects, the administering comprises ophthalmic application of said composition comprising purified SDC2+ exosomes. In some aspects, the administering comprises injecting said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises peritoneal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, the use comprises administering an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. In some aspects, the population of exosomes comprises an exosome containing at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the exosome protein constituent is not detected by the host humoral immune system. In some aspects, obtaining the population of exosomes comprises freezing the population of exosomes. In some aspects, obtaining the population of exosomes comprises storing the population of exosomes at room-temperature. In some aspects, obtaining the population of exosomes comprises storing the population of exosomes without cryogenic preservation. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs(miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are populations of exosomes for use in preparation of a medicament for delivering an immuno-modulatory signal to an intracellular space of a mammal, comprising the steps of obtaining a population of exosomes from a SDC2+ mesenchymal stem cell; and administering the population of exosomes to the mammal; wherein the population of exosomes contains the immuno-modulatory signal; and wherein contents of the exosomes are delivered to an intracellular space of the mammal without eliciting a humoral immune response to the contents of the exosome in the mammal. In some aspects, the exosomes are paracrine signaling exosomes. In some aspects, the population of exosomes is drawn into an intracellular space of a mammal by phagocytosis. In some aspects, the population of exosomes is drawn into an intracellular space of a mammal by endocytosis. In some aspects, the population of exosomes is drawn into an intracellular space of a mammal by fusion. In some aspects, the administering comprises injecting the population into the mammal. In some aspects, the administering comprises topically applying said composition comprising purified SDC2+ exosomes. In some aspects, the administering comprises a hydrogel or collagen gel. In some aspects, the administering comprises intraocularly applying said composition comprising purified SDC2+ exosomes. In some aspects, the administering comprises ophthalmic application of said composition comprising purified SDC2+ exosomes. In some aspects, the administering comprises injecting said composition comprising purified SDC2+ exosomes. In some aspects, said injecting comprises injecting directly into lymph nodes of a patient. In some aspects, said delivering comprises subcutaneous delivery of said composition comprising purified SDC2+ exosomes. In some aspects, said delivering comprises peritoneal delivery of said composition comprising purified SDC2+ exosomes. In some aspects, said delivering comprises inhalation. In some aspects, inhalation comprises use of an inhalation device. In some aspects, the inhalation device is a nebulizer. In some aspects, the use comprises administering an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. In some aspects, the population of exosomes comprises an exosome containing at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the exosome protein constituent is not detected by the host humoral immune system. In some aspects, obtaining the population of exosomes comprises freezing the population of exosomes. In some aspects, obtaining the population of exosomes comprises storing the population of exosomes at room-temperature. In some aspects, obtaining the population of exosomes comprises storing the population of exosomes without cryogenic preservation. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs(miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are compositions comprising cultured stem cells and exosomes, wherein the exosomes were generated during culturing of the stem cells, collected, concentrated, and added back to the cultured stem cell composition. In some aspects, the exosomes are paracrine signaling exosomes. In some aspects, the cultured stem cell composition is subjected to at least 20 cumulative populations to a mammal in need of wound healing. In some aspects, the cultured stem cell composition is perturbed to elicit exosome production. In some aspects, the cultured stem cell composition is transformed to overexpress SDC2/S2/CD362/fibroglycan. In some aspects, the cultured stem cell composition is irradiated. In some aspects, the cultured stem cell composition is irradiated using gamma irradiation. In some aspects, the cultured stem cell composition is subject to inflammatory stimulation. In some aspects, the inflammatory stimulation comprises at least one of TNF-alpha, Interferon-gamma, Interferon-beta, Interleukin-1b, TLR agonists, Poly I:C, and LPS. In some aspects, the cultured stem cell composition is subject to growth arrest. In some aspects, the growth arrest comprises at least one or gamma-irradiation, mitomycin-c, TGFb stimulation, and growing cells to confluence. In some aspects, the cultured stem cell composition comprises mesenchymal stem cells. In some aspects, the cultured stem cell composition comprises mesenchymal stromal stem cells. In some aspects, the cultured stem cell composition comprises at least 20% SDC2+ mesenchymal stem cells. In some aspects, the cultured stem cell composition comprises at least 20% SDC2+ mesenchymal stromal stem cells. In some aspects, the cultured stem cell composition comprises at least 20% SDC2+ stem cells. In some aspects, the cultured stem cell composition comprises at least 30% SDC2+ stem cells. In some aspects, the cultured stem cell composition comprises at least 40% SDC2+ stem cells. In some aspects, the cultured stem cell composition comprises at least 50% SDC2+ stem cells. In some aspects, the cultured stem cell composition comprises at least 60% SDC2+ stem cells. In some aspects, the cultured stem cell composition comprises at least 70% SDC2+ stem cells. In some aspects, the cultured stem cell composition comprises at least 80% SDC2+ stem cells. In some aspects, the cultured stem cell composition comprises at least 90% SDC2+ stem cells. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, exosomes comprise IL12, suppressor of cytokine signaling (SOCS), p53, PTEN, CD52, tsc1, Foxp3, Soluble Immune Response Suppressor (SIRS), TGFB, CD39, CD39L3, CD73, and maspin. In some aspects, the cultured stem cell composition comprises an immunosuppressive drug. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. In some aspects, the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. In some aspects, the immunosuppressive drug comprises an anti-TNF antibody. In some aspects, the immunosuppressive drug comprises a TNF inhibitor. In some aspects, the immunosuppressive drug comprises an NSAID. In some aspects, the immunosuppressive drug comprises a steroid. In some aspects, the exosomes are purified. In some aspects, the exosomes are isolated. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprises microRNAs(miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

Also provided herein are methods of obtaining an immuno-modulatory composition comprising exosomes, comprising obtaining exosomes from a population of stromal cells that SDC2 are at least 20% SDC2+. In some aspects, the exosomes are paracrine signaling exosomes. In some aspects, the exosomes are SDC2−. In some aspects, the exosomes comprise SDC2 as an exosome surface constituent. In some aspects, the exosomes comprise SDC2 as an exosome interior constituent. In some aspects, the exosomes are derived from a stromal cell induced to express SDC2. In some aspects, the method comprises transforming the stromal cell to overexpress SDC2/S2/CD362/fibroglycan. In some aspects, the method comprises irradiating the SDC2+ stromal cell. In some aspects, the method comprises irradiating using gamma-irradiation. In some aspects, the method comprises subjecting the SDC2+ stromal cell to inflammatory stimulation. In some aspects, the inflammatory stimulation comprises at least one of TNF-alpha, Interferon-gamma, Interferon-beta, Interleukin-1b, TLR agonists, Poly I:C, and LPS. In some aspects, the method comprises subjecting the SDC2+ stromal cell to growth arrest. In some aspects, the growth arrest comprises at least one or gamma-irradiation, mitomycin-c, TGFb stimulation, and growing cells to confluence. In some aspects, the method comprises providing a physiologically acceptable buffer. In some aspects, at least 30% of the exosomes comprise SDC2. In some aspects, at least 40% of the exosomes comprise SDC2. In some aspects, at least 50% of the exosomes comprise SDC2. In some aspects, at least 60% of the exosomes comprise SDC2. In some aspects, at least 70% of the exosomes comprise SDC2. In some aspects, at least 80% of the exosomes comprise SDC2. In some aspects, at least 90% of the exosomes comprise SDC2. In some aspects, at least 95% of the exosomes comprise SDC2. In some aspects, at least 99% of the exosomes comprise SDC2. In some aspects, the exosomes are CD45−. In some aspects, the composition does not comprise a living cell. In some aspects, the composition is non-tumorigenic. In some aspects, the composition is stable for over 48 hours without cryopreservation. In some aspects, the composition comprises SDC2+ mesenchymal stem cells. In some aspects, the composition is frozen. In some aspects, the composition is lyophilized. In some aspects, a therapeutically active amount of exosomes are obtained. In some aspects, at least $10^6$ exosomes are obtained. In some aspects, at least $10^7$ exosomes are obtained. In some aspects, at least $10^8$ exosomes are obtained. In some aspects, at least 1 µg of exosomes are obtained. In some aspects, at least 10 µg of exosomes are obtained. In some aspects, at least 20 µg of exosomes are obtained. In some aspects, at least 50 µg of exosomes are obtained. In some aspects, at least 100 µg of exosomes are obtained. In some aspects, at least 150 µg of exosomes are obtained. In some aspects, at least 200 µg of exosomes are obtained. In some aspects, at least 250 µg of exosomes are obtained. In some aspects, at least 500 µg of exosomes are obtained. In some aspects, at least 750 µg of exosomes are obtained. In some aspects, at least 1 mg of exosomes are obtained. In some aspects, at least 2 mg of exosomes are obtained. In some aspects, at least 3 mg of exosomes are obtained. In some aspects, at least 4 mg of exosomes are obtained. In some aspects, at least 5 mg of exosomes are obtained. In some aspects, at least 6 mg of exosomes are obtained. In some aspects, at least 7 mg of exosomes are obtained. In some aspects, at least 100 mg of exosomes are obtained. In some aspects, at least 200 mg of exosomes are obtained. In some aspects, at least 300 mg of exosomes are obtained. In some aspects, at least 400 mg of exosomes are obtained. In some aspects, at least 500 mg of exosomes are obtained. In some aspects, at least 600 mg of exosomes are obtained. In some aspects, at least 700 mg of exosomes are obtained. In some aspects, the exosomes are purified. In some aspects, the exosomes are isolated. In some aspects, the stromal cells are cultured in a hollow-fiber bioreactor. In some aspects, the composition comprises CD39, CD39L3 and CD73. In some aspects, enzymes such as CD39 and CD73 convert extracellular ATP to adenosine, which in turn often accomplish at least one of reducing inflammation and reprogramming lymphocytes and myeloid cells to an anti-inflammatory phenotype. In some aspects, the composition comprise microRNAs (miRNAs). In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
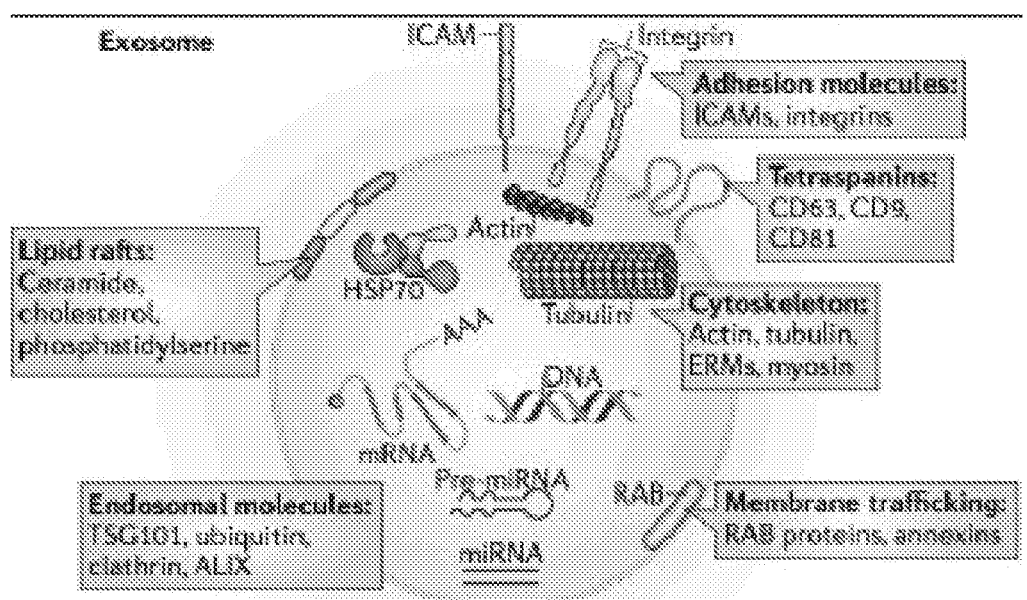
FIG. 1 shows a cartoon depiction of an exosome.

Mesenchymal stem cells or mesenchymal stromal cells have shown therapeutic value, for example, in their ability to migrate to the site of tissue injury and relative ease of in vitro expansion. It has been suggested, however, that the benefit of mesenchymal stem cells is not in differentiating and replacing dead and dying cells in the injured tissue. Instead, it is thought that the cells activate protective pathways and stimulate endogenous regeneration to heal the injury via paracrine signaling by exosomes or microvessicles secreted by the mesenchymal stem cells. For example, in an acute kidney injury model, mesenchymal stem cells have been found to accelerate recovery and induce improvement in chronic kidney disease. However, few of the systemically administered mesenchymal stem cells were found to permanently engraft at the site of injury. Instead it was thought that the mesenchymal stem cells were providing paracrine support to repair the tissue. This hypothesis is supported by experiments where media taken from cultured mesenchymal stem cells (i.e. conditioned media) showing a therapeutic benefit in this model. Therefore, mesenchymal stem cells exert therapeutic benefit, at least in part, through paracrine signaling.

Paracrine action of mesenchymal stem cells is also illustrated by their activity in modulating the immune system. Mesenchymal stem cells have been shown to inhibit T lymphocyte activity; alter cytokine production by dendritic cells, T cells and natural killer cells; and increase production of regulatory T cells, creating a more anti-inflammatory environment. It is thought that mesenchymal stem cells create an anti-inflammatory environment via paracrine signaling exosomes.

Exosomes have discovered to mediate cell-cell communication, including paracrine signaling. Exosomes derive from endosomal membrane cell compartments and are released from the cell after fusion of multivesicular bodies with the plasma membrane. Exosomes are generally homogenous in size, ranging from 30 to 120 nm and are released from the cell via p53 mediated exocytosis, which is dependent on cytoskeleton and independent of calcium influx. Exosomes signal target cells by specific receptor-ligand interactions and transfer receptors and bio-active proteins, lipids, mRNAs, and miRNAs.

Exosome or microvesicle compositions and methods of isolation and uses for modulation the inflammatory response are disclosed herein. In some cases these compositions mediate ofparacrine signaling or deliver paracrine signaling components. Exosomes or microvesicles isolated from stromal cells or mesenchymal stem cells (e.g., mesenchymal stromal stem cells) are shown herein to be efficacious in treating inflammatory and immune disease with advantages over mesenchymal stem cells and other therapeutics currently available. For example, exosome compositions disclosed herein are easy to manufacture. Isolation or purification of exosome compositions by methods disclosed herein, are easily performed and standardized for dose and biological activity based on the inflammatory or immune disease in need of treatment. Exosome or microvesicle compositions show decreased batch variability relative to mesenchymal stem cells and stromal cells involve fewer steps to create a therapeutic to be administered to a patient in need of treatment.

In addition, exosome compositions disclosed herein have the advantage of easy long term storage. Therapeutics derived from cultured cells, such as mesenchymal stem cells, mesenchymal stromal stem cells or stromal cells, must be carefully cryogenically stored using cryopreservatives such as DMSO or glycerol and frozen using specific methods including flash freezing and controlled rate freezing. In contrast, exosome compositions, such as those described herein, can be frozen and stored in a physiologically acceptable buffer or excipient that does not contain a cryopreservatives and maintain full or near full potency. In other words, exosome compositions can be frozen in ready to use vials, syringes, or other container that would be used for a therapeutic made from exosomes and would not need to be first purified from a cryopreservative that may be toxic or harmful to the individual needing treatment.

Exosomes, including exosome compositions described herein, also are advantageous due to their property of being non-viable. Tumors or cancer have been proposed to be a risk when administering stem cell therapies to an individual with an established cancer, as it is possible for the administered cells to form a tumor or cancer once administered. In contrast, exosome compositions are not able to self-replicate, therefore they are non-tumorigenic. That is to say, administration of exosome compositions to an individual needing treatment will not lead to increased risk of tumors or cancer in the individual. This has been proposed to be a risk when administering stem cell therapies to an individual with existing cancer, as it is possible for the administered cells to form a tumor or cancer once administered.

Further, exosome compositions as described herein also have the advantage of having lower immunogenicity than mesenchymal stem cells, mesenchymal stromal stem cells or stromal cells. Cells, including mesenchymal stem cells, mesenchymal stromal stem cells and stromal cells, express proteins on their surface which can interact with the immune system when administered to an individual being treated. In contrast, exosome compositions have fewer proteins bound to their membrane, thereby making them less immunogenic than the mesenchymal stem cells, mesenchymal stromal stem cells or stromal cells from which the exosome compositions are isolated or purified.

Additional uses for exosome compositions include compositions that include anti-inflammatory therapeutics formulated with the exosomes. This feature would allow a therapeutic to be delivered to an individual who needs treatment without eliciting an immune response, specifically a humoral immune response to the anti-inflammatory therapeutic. For example, an anti-TNF antibody, such as infliximab, could be formulated with the exosome compositions and when administered, the individual's immune system, specifically their humoral immune system would not be activated by the therapeutic that is made in this way. Alternately or on combination a native signaling component, such as a paracrine signaling component, is contained in some exosome compositions.

In some cases, mesenchymal stem cells, mesenchymal stromal stem cells, or stromal cells, have been found to lose potency when cultured over large numbers of passages or doublings. Exosome compositions, including, among others, exosome compositions with paracrine signaling activity, when added back to the mesenchymal stem cells or mesenchymal stromal stem cells with a large passage number, improve the ability of the mesenchymal stem cells to elicit therapeutic efficacy when administered to an individual, than the mesenchymal stem cells with a large passage number alone. This would, for example, allow a mesenchymal stem cell culture to be more greatly expanded without impacting its therapeutic efficacy when administered to an individual.

In addition, exosome compositions, such as those described herein, can also be combined with regulatory T cells, such as CD4+CD25+FOXP3+ regulatory T cells, to create therapeutics that treat inflammatory or immune diseases. The exosome compositions, in this case, would enhance the activity, potency and longevity of a regulatory T cell therapeutic.

Compositions

Provided herein are compositions, such as therapeutically active, compositions comprising exosomes, for example in vitro exosomes, such as SDC2+ exosomes. In some cases the exosomes comprise components that mediate, effect or inhibit paracrine signaling. In some cases, at least 20% of the exosomes in the composition are SDC2+ or comprise SDC2. In some cases at least 20%, 30%, 40%, 50%, 60%, 70%, 80%, 90%, 95%, 99%, or more of the exosomes comprise SDC2. SDC2, also known as syndecan-2, CD362, S2, and fibroglycan, in some instances is found on the surface of the exosome. In some instances, SDC2 is found at the interior of the exosome. The proportion of exosomes in the composition comprising SDC2 is determined by immunofluorescence, for example flow cytometry, electron microscopy, or other method known by one of skill in the art.

SDC2 refers to a gene encoding the syndecan-2 protein (also frequently referred to herein and elsewhere in the art as SDC2). Syndecan-2, or 'the SDC2 protein' or simply SDC2, is a transmembrane type I heparan sulfate proteoglycan. Additional synonyms for syndecan-2, aside from 'the SDC2 protein' or SDC2, include HSPG, CD362, HSPG1, and SYND2. Generally, as used herein SDC2 refers to the protein or a recognizable fragment thereof unless otherwise indicated, for example by reciting 'the SDC2 gene,' 'the SDC2 transcript,' 'an SDC2 antibody.' Additionally, SDC2 is identified by its polypeptide sequence in the sequence listing that accompanies this specification.

SDC2 has three domains: an extracellular domain at amino acids 19-144, a transmembrane domain at amino acids 145-169, and a cytoplasmic domain at amino acids 170-201. SDC2 has been implicated in the mediation of cell binding, cell signaling, and cytoskeletal organization. SDC2 has been demonstrated to be necessary for internalization of HIV-1 TAT protein.

While exosome compositions described herein, in some cases, are derived from cells, the exosome compositions do not necessarily comprise living cells. Cell-free exosome compositions, therefore, are non-tumorigenic, that is, they do not increase the susceptibility of a subject to developing a tumor or cancer, because they do not comprise cells capable of differentiating into tumor cells. In alternative compositions, the exosomes are supplemented with cells, such as mesenchymal stromal cells, that contribute to anti-inflammatory activity or paracrine signaling activity of the compositions.

Exosome compositions disclosed herein retain potency or activity, such as paracrine signaling activity, after being frozen or cryopreserved, often without the use of a cryoprotectant. Cryoprotectants include DMSO, glycerol, polyethylene glycol, propylene glycol, glycerine, polyvinylpyrolidone, sorbitol, dextran, trehalose, and commercial formulations such as CryoStor from Biolife solutions. The exosome compositions also retain potency after being frozen without using special freezing protocols. Special freezing protocols include flash freezing, programmable rate freezer, and freezing in an insulated container. A benefit of the durability of the exosome compositions is that they are more easily frozen and are frozen without cryoprotectants, resulting in compositions that are more durable, more easily and cheaply made, and less likely to suffer from batch variation resulting from loss of activity due to a defect in freezing protocol or composition. The exosome compositions are in some cases frozen in buffer or culture media. Buffers include physiologically acceptable buffers such as phosphate buffer, histidine buffer, citrate buffer, acetate buffer, Hypothermasol from Biolife Solutions and other buffers known by those of skill in the art. In some cases exosome compositions disclosed herein are lyophilized.

Exosome compositions disclosed herein are formulated in a physiologically acceptable buffer and in some cases supplemented by at least one excipient. Non-limiting examples of excipients include sucrose, trehalose, polyethylene glycol, a polysaccharide, a carrier protein, an inert protein, dextran, hydroxyl ethyl starch (HETA), PEG-4000, gelatin, PLGA, Eudragit RS 100 Nanoparticles, and combinations thereof. Such exosome compositions are stored at a temperature determined to be most stable (i.e., wherein the exosome composition retains highest potency, or retains potency for the longest period of time, or otherwise optimizes a desired trait). In some cases, addition of at least one excipient allows the composition to retain potency, such as paracrine signaling potency, when stored at a higher temperature than otherwise would be possible.

Some exosome compositions such as paracrine signaling exosome compositions disclosed herein, in some cases, comprise in vitro exosomes and SDC2+ mesenchymal stem cells, (e.g., mesenchymal stromal stem cells). The cells combined to in vitro exosomes are in some cases regulatory T cells, such as CD25+ regulatory T cells, CD4+ regulatory T cells, FoxP3+ regulatory T cells, CD25+CD4+FoxP3+ regulatory T cells, or combinations thereof. In some instances, exosome compositions comprise in vitro exosomes, SDC2+ mesenchymal stem cells (e.g., SDC2+ mesenchymal stromal stem cells), and regulatory T cells.

Compositions comprising a wide range of exosomes are disclosed herein. Some compositions comprise exosomes in a therapeutically effective amount, which would be known or readily determined by one of skill in the art. In some compositions, the amount of exosomes ranges from $10^6$-$10^8$ exosomes, for example $10^6$, $10^7$, $10^8$, or more exosomes in the composition. In some cases, a therapeutically effective amount of exosomes ranges from 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Exosome compositions, in some cases, are concentrated to be diluted by the individual prior to administration. In some cases, exosome compositions are diluted and ready to be administered by the individual. In some cases, exosome compositions are contained in single use vials or syringes. In some cases, multiple doses are present in a single container.

Some exosome compositions disclosed herein comprise additional proteins, such as proteins that contribute to therapeutic efficacy, or that mediate paracrine signaling to effect therapeutic efficacy. Proteins include but in some cases are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin. In some cases, exosomes comprise at least one of protein selected from the list consisting of UBA6, ESYT2, SSC5D, STMN1, STMN2, PRNP, VEGFA, ADD1, NBL1, MINOS1-NBL1, XIRP2, VPS37C, MARS, BST1, MAP1LC3B, MAP1LC3B2, RPSA, RPSAP58, BPNT1, ABI1, SEPT8, NUDT5, WBP2, SPTAN1, ATP1B1, DYNLT3, YIF1A, SEC61A2, SEC61A1, DOCK11, NDE1, NDEL1, UFD1L, SNX1, KIAA1217, CNIH4, CRYZL1, PRAMEF26, PRAMEF11, PRAMEF6, PRAMEF5, PRAMEF23, PRAMEF9, PRAMEF4, ANXA6, CD9, AMOT, PPP2R4, SELENBP1, PSMD4, PIP5K1A, PIPSL, MLLT4, GSK3A, RTN1, MPP1, DSCR3, SUMO2, SUMO3, SUMO4, PPP5C, AIMP2, TUBA4A, RPL23A, CASP3, FAM171A2, KIAA1324L, RAB34, C2orf74, DRG2, MBP, PTTG1IP, MBOAT7, CSNK1E, CSNK1D, EIF3L, EIF3D, UBE2I, CPNE1, APOC3, ARCN1, XRCC6, PSMD10, CROCC, NRD1, TSPAN2, MTOR, DYNLRB1, DYNLRB2, PEA15, POSTN, ARHGEF7, LPHN2, SEPT6, CD58, LGALS8, CD55, C1orf123, EPS15, MUC1, PSAP, GML, TXNRD1, HMGB1, HMGB1P1, RUVBL2, SLC29A1, EIF3S3, EIF3H, EIF3F, METRNL, CA12, PLTP, FNTA, SNRPN, SNRPB, HARS, AP1G1, CDIPT, CNN2, LARS, EIF2A, NAPG, CNN3, IDH2, ULK3, RPS6KA3, NPLOC4, CANX, EIF2B1, PIP4K2A, MYRF, TMEM165, EPN3, TARDBP, RAB5A, SNRPD3, SNX6, CS, LPAR1, AKR1C1, AKR1C2, AKR1C3, SACM1L, CARS, CHURC1-FNTB, FNTB, PCBP2, PCBP3, STAT2, NQO1, MAT2A, STRAP, IL6, SERPINB1, ABHD14A, ABHD14A-ACY1, ACY1, PTGES3, PGD, NPC2, HIST1H2BN, HIST1H2BL, HIST1H2BM, HIST1H2BH, HIST2H2BF, HIST1H2BC, HIST1H2BD, H2BFS, HIST1H2BK, HIST2H2BE, HIST1H2BB, HIST1H2BO, HIST1H2BJ, STK24, PLOD1, ELMO2, ZDHHC20, FAM98A, ANXA7, SLC2A5, PLSCR1, RASA1, DKFZp434N071, SLC9A1, MTAP, TMBIM1, SERINC3, AHSA1, QARS, ARL1, DNAJB1, NMT2, NMT1, FXR1, HNRNPC, RALYL, HNRNPCL1, TGFBR1, ME1, COPB2, TKT, RALB, DBF4B, LRCH3, PNPO, RBM4B, MST4, SERPING1, GALK1, PBXIP1, AQP1, SRSF3, FARSA, EML4, PPP1R7, STEAP2, GUCD1, PDIA6, SIRT2, QPCT, TSPAN9, RAN, EIF3C, EIF3CL, SEPT10, CAP2, NTM, HBS1L, RCN1, ATP6V1A, RNF14, SLC26A4, PTPRA, ATP6VOA1, MFSD8, TOM1L2, SGCE, CYTH3, TSPAN5, EXOC4, PPP6C, ALAD, PFKM, ISYNA1, PCYOX1, ATP6AP2, CAST, RPN1, INPP5K, SLC6A9, LPXN, AKT1, RRAS2, DECR1, SH3KBP1, NUBP2, PMM2, SCFD1, ACP2, PITPNB, GYS1, USP7, GPRC5B, RAB1A, EMB, EBF2, PCMT1, NAP1L1, SH3PXD2A, CCT4, GALK2, DLST, SH3GLB2, SCARB1, CCDC122, HSPE1, PPIL3, PTMA, TAX1BP1, EVA1A, FAM126A, TCEB2, IGLL5, DNPEP, DIAPH1, DISC1, TSNAX, DCUN1D1, PFN2, SRI, CNTLN, EEF1E1, EEF1E1-BLOC1S5, PTPN12, EIF4G1, TMEM248, TPST1, CPA4, MID1, CXCL8, RPL37A, KIAA0319L, IGF1R, TMEM98, PFN2, TNPO3, ATP6V1E1, RARRES2, ITGB6, APPL1, IFT57, TFPI, PSPH, QPRT, MEST, LTBP1, PRPSAP2, MTMR2, GPS1, CYCS, ITM2C, TYMP, APEH, OXSR1, PPM1B, TFG, ARVCF, STARD3NL, KIAA0195, MTPN, DGKA, MASP1, FARP1, FAM3C, DDX17, RPL24, UBA5, SEC14L2, SEC14L3, TIA1, TIAL1, BTN3A3, BTN3A2, BTN3A1, CD63, LEPROTL1, TENC1, ARMC9, EPHA5, EPHA3, TMEM106B, RPL35A, TMEM50B, ALB, EIF4G2, GNPDA1, GNPDA2, CAMK2D, CAMK2B, CAMK2A, GPM6A, ABCE1, CLDND1, MFSD10, RPL9, NECAP2, CTBP1, CTBP2, SPON2, SNF8, DCTD, RELL1, LMAN2, EIF4E, TTC37, IGJ, ALG13, RPS23, SRP72, CALCOCO2, PAIP1, RNASET2, SEPT11, SEC31A, MCC, CXCL6, CXCL5, HAPLN1, CD14, COL12A1, CLTB, ELOVL5, EIF3E, LYPLA1, PFDN1, TCEB1, SORBS3, ERLIN2, ERLIN1, ENY2, RPL30, PLAA, FABP4, TBCA, MAT2B, SKP1, COPS6, SQSTM1, AP3D1, BLMH, RAI14, MAP4K4, FES, FER, SEC24C, ABI2, RPL14, CD44, SEPT7, PTPRM, GLB1, SLC43A3, EIF4A2, PABPC1, PABPC4, PAPSS2, ATP2C1, TNS1, TNS3, THBS4, HEPH, PSEN1, XPO7, PLAU, ITGA2, STX3, PPP3CA, RPS24, PLOD2, MARK2, MARK1, MARK3, GPX8, BZW2, GDI2, CSNK2A1, CSNK2A3, DKK3, CDK14, CDK4, CDK3, CDK1, CDK16, CDK12, CDK15, CDK9, CDK18, CDK13, SF3A3, ASB2, CAPN5, CYFIP2, KLC1, MYO6, IQGAP2, ADAM23, HYI, TRIO, MGLL, DCTN1, NIF3L1, PI4K2A, NACA, GPR84, MGRN1, PACS2, RBBP7, RBBP4, NLN, COL6A3, HNRNPH1, MDH2, PTPRD, PTPRS, MYO1B, PHLDB2, SRP9, ATP11A, PPIE, DIP2A, EPB41, DTNB, TNS1, RND3, PPP2R5D, MANBA, AP2M1, APP, AAK1, C1QTNF3-AMACR, C1QTNF3, TSN, KIDINS220, DPM1, GSTM2, PLSCR4, EPB41L2, PRKCDBP, MUC15, PDE8A, THY1, TCP11L1, RPL27A, CRYAB, AAMDC, TMEM126B, EEFID, SCYL1, PPP6R3, PRMT1, DCAF5, NUCB2, TSTA3, RPL8, HYOU1, RAB1B, NPEPPS, MDK, VKORC1, AASDHPPT, RNF141, TYK2, USP47, WLS, PSMC3, TSPAN4, STT3A, CD59, LRP8, RAE 1, MVB12A, IFITM2, IFITM3, IFITM1, MAPK3, PFDN4, IFT46, EFEMP2, NSFL1C, FRYL, ARRDC1, PITPNA, CCT2, ADA, PCDH7, KRT17, SMAD5, TMED2, MPI, ITFG1, METAP1, RPTOR, HN1, GALNT1, COPS7A, KPNA6, KPNA5, KPNA1, OTUB1, ATP6VOD1, PXN, MACF1, SLC3A2, PPP3CB, GLTP, FERMT3, FBLN2, SEMA3C, CALD1, DCTN2, UACA, TENM2, MTHFD1, CBS, EIF3A, HMBS, SEC23A, PPP2R1A, TSG101, AP3S1, TMX3, VPS26A, VPS37B, SUGT1, SLC8A1, STK4, LSAMP, CDC42BPA, B2M, ATL3, TBC1D9B, FARSB, CDK17, VDAC3, CYB561, MFGE8, FZD6, BCAR1, TNIK, RPS10, RPS10-NUDT3, ST13, ST13P4, ST13P5, RBM38, PIP4K2C, CAD, PRKAG1, TMBIM6, DDX39B, DDX39A, DDX39, hCG 2005638, C12orf75, OCC1, C12orf10, CSRP2, COPZ1, SCYL2, PLXNA1, IGFL2, PTPRB, CHMP1A, RPL18, SLC25A3, SLC38A1, VPS29, PPP1CC, KIAA1033, KRT18, CTDSP2, FMNL3, PDE6H, MYL6, HNRNPA1, MYH10, RASA3, SDK1, BRE, GOLIM4, RANGAP1, RTN4, IGF2BP2, EXOC5, ABHD14B, PRKD2, PRKD1, PRKD3, TM4SF1, RNF149, ARPC4, ARPC4-TTLL3, CMTM7, DTNA, DTNB, PAM, TRAPPC2P1, TRAPPC2, ATP6V1H, DPP3, RPL21, TJP1, HBA2, GOLT1B, BAG5, PSMA6, UBE2V1, UBE2V2, MPP5, GNG2, FBN3, ACYP1, PTGER2, VPS33B, LTBP2, SRP54, GMFB, FRMD6, FBLN5, GNPNAT1, SHMT2, SLC7A7, SULF2, LAMB1, COMP, SBF1, TTC7A, PDIA3, COBLL1, XPN-PEP1, DNMIL, GRK5, GRK6, GRK4, CDSN, MVB12B, ALDH1A3, HP, HPR, AMPD2, KCNMA1, FN1, IMPDH2, APMAP, CC2D1B, TBC1D8B, COL12A1, PTPRF, CALM2, CALM1, CALM3, HNRNPD, ATP10D, FST, COL14A1, VEGFA, CTSC, CTSF, MYCT1, CD40, RPS2, SCP2, CRIP2, C1R, REXO2, M6PR, LOC388849, IFT81, DHRS7, PPP2R5C, HECTD1, ETFA, WDR61, GMPR2, LDLR, RPS27L, RPS27, PSMA4, ANP32A, ANP32B, SPPL2A, PSME1, COMMD4, SPNS1, SLC9A3R2, RPS15A, CARHSP1, FUS, TAF15, HAGH, HNRNPUL2-BSCL2, HNRNPUL2, GSPT1, UBFD1, LRRC57, DDX19A, DDX19B, HAPLN3, HAPLN4, BOLA2B, BOLA2, STXBP5, GCA, CHIA, ABCB6, COL5A1, WDR44, PDIA3, ZPR1, YIPF4, AP1S1, AP1S2, MMS19, CTDSP1, TSPAN15, MANF, POFUT2, PLOD3, MITD1, STRADB, PRDX4, SRPRB, MAGI1, ATP11B, MFSD1, IAH1, EFR3A, BRCC3, TXNDC17, NSF, PCYT2, CRK, MLKL, TFAP4, TOM1L1, EIF5A, EIF5AL1, EIF5A2, SRR, RPS15A, CCDC43, BAIAP2, SLC12A4, RPS13, MATN2, PI4KA, KIAA0368, ECM29, PSMD9, KIF5A, KIF5C, GPR176, PARVA, ITGA7, FHL2, MYO18A, LEKR1, GAS6, OLA1, TGOLN2, SYT1, STRA6, PSD3, PPP2R5E, IARS, NT5C, COPZ2, TANC2, RPL17, SRSF1, RPL38, FBXL20, RPL19, ARHGDIA, AKT2, SNRPD1, VWA1, ACE, ERBB2, CDKN2A, CDKN2B, MYL12A, MYL12B, YES 1, RPL13, FNBP 1L, TMEM8A, CUL4B, MYO1D, KATNAL2, SMAD4, RPS15, RPL22, TBCB, PKN1, SEPT9, SYNGR2, PRKCSH, RAD23A, EIF1, EIFIB, ACTG1, MRI1, PIN1, STAT3, UBXN6, DAZAP1, PDCD5, CARM1, CDC37, GPX4, PSENEN, RAB27B, COPE, ARHGEF1, NUMBL, HNRNPM, AP2S1, EMP3, RCN3, GGCT, JOSD2, CLEC11A, RPS5, MYO9B, AXL, PLAUR, RPL18A, SPATA22, EPS15L1, CHMP2A, KDELR1, KDELR2, RPS16, DPP9, TBC1D17, PAFAH1B3, ACOT7, MYO1C, SNAP23, STXBP3, AP3B1, TNFRSF10A, PSMD11, PSMD12, PGRMC1, CLIC1, QSOX1, IPO5, RTCA, AGRN, PSMD14, KPNA3, STK25, KRIT1, SDCBP, SDCBP, DDX3X, DDX3Y, CYR61, KPNA4, PDXK, CLDN4, CLDN9, CLDN6, CLDN3, PPAP2A, PPAP2B, ISLR, TXNDC9, HSPB6, ADAM10, ITGBIBP1, PRMT5, SLC9A3R1, TNFRSF10B, NRP1, MRAS, PSMA7, SCAMP3, TAX1BP3, GIPC1, CASK, HGS, PPP1R12A, PPP1R12B, XPO1, PLXNB2, NPC1, SCAMP1, SCAMP2, ARPC1B, ARPC2, ARPC3, PGRMC2, PFDN6, LAMA5, LEPROT, RER1, SURF4, INPPL1, NCAM2, STX7, SLC16A3, SLC31A1, ABCC3, ABCC4, P4HA2, YKT6, ARPC5, FLRT2, PLXNB1, PHGDH, ADAM12, GPR39, DYNC1LI2, PSMD3, PAPSS1, B4GALT5, TGFB1I1, TXNL1, TPD52L2, FIBP, AKR7A2, EPB41L2, ATP8B1, ATP8B4, DENR, XPOT, TSPAN6, ASNA1, ACTN4, KDELR3, SGTA, NARS, LANCL1, CALU, EDIL3, AHCYL1, AHCYL2, SPAG9, MAPK8IP3, PIP5KIC, DFNA5, NRP2, ACSL4, SNX3, ADCY9, SYNCRIP, HNRNPR, GREM1, EXOC3, PLIN3, SLC16A7, UGDH, CTNND1, SNX2, USO1, TOM1, PRAF2, EIF5B, DNAJA2, CUTA, SRGAP2, SRGAP2C, PLXNA2, WDR1, FZD7, SLIT3, ROCK2, CPNE3, DNAJC13, USP12, SEMA7A, PDCD6, ATP6V1G1, ATP6V1G2-DDX39B, ATP6V1G2, VPS4B, SH3BGRL, FLNB, SEC22B, ERLIN1, GPC4, CLDN11, TIPRL, RP2, SLC22A3, EIF3J, CBR3, IDH1, ATRN, STAM2, ARL6IP5, DCTN3, FLOT1, CPD, GLRX3, STC2, CIAO1, DDAH1, STK10, GFPT2, SLIT2, SEC24D, FARP2, DKK1, ABCA8, ENDOD1, AP2A2, PRSS23, S1PR2, UBL3, VAMP5, RTN3, VAPB, MPZL1, PGLS, ATG7, LYPLA2, IPO7, PGM3, APOM, FMNL1, ABCA1, SEC24A, SFT2D2, ACSL3, STAMBP, AP2A1, TMEM50A, BAG2, BAG3, CLDN1, CLIC3, TSPAN13, TSPAN31, DDAH2, ITGBL1, RECK, LDHA, ALDH1A1, GLUD1, GLUD2, CYB5R3, GSR, SOD1, F13A1, PNP, HPRT1, GOT2, EGFR, PGK1, AK1, C1R, F10, PLAT, ASS1, C3, TIMP1, CST3, CSTA, NRAS, HRAS, KRAS, TGFB1, PENK, NPY, IGF2, IL1B, IGHG1, IGHG3, HLA-A, COL1A1, COL3A1, COL4A1, LMNA, APOE, SLC4A1, FN1, FN1, FN1, RBP4, ORM2, ORM1, TFRC, FTL, FTH1, MT1X, MTIG, MT2A, MTIM, MT1E, MT1H, MTIA, ANG, VTN, CAT, ALDOA, CSTB, ANXA1, APOB, SOD2, OAT, KRT1, GAPDH, ASL, CAPNS1, HSPB1, RPN2, GNAI2, ATP1A1, ARG1, ITGB3, S100A8, SERPINB2, SERPINE1, ISG15, ALPL, EIF2S1, ICAM1, RPLP1, RPLP2, RPLP0, RPLP0P6, FABP3, ITGB1, PRKCB, MYL1, MYL3, COL5A2, UROD, INSR, FYN, GSN, GSN, S100A9, S100A6, ENO1, PYGL, GPI, NPM1, TPM3, ITGAV, LPL, SERPINE2, SERPINE2, EPHX1, DBI, LDHB, GPX1, P4HB, CTSD, ANXA2, ANXA2P2, CAPN1, TUBB, DCN, PFN1, BPGM, APRT, EPRS, CTSB, HSP90AA1, LYN, THBS1, HSPA1A, COL1A2, ANXA6, RHOC, PFKM, HSP90AB1, ASNS, MMP2, SOD3, MME, INHBA, MGP, ITGA2B, COL4A2, MFI2, ITGA5, VIM, RPS17L, RPS17, GNAI3, ANXA5, FGF2, ENO2, GSTP1, SNRPC, CXCL1, LGALS1, RBP1, SPARC, GSTM1, GSTM4, TPM1, TPM1, CLTA, ANXA4, CNP, PDGFRB, C1S, UCHL1, LTA4H, ALDOC, HIST1H2AJ, HIST1H2AH, H2AFJ, HIST2H2AC, HIST2H2AA3, HIST1H2AD, HIST1H2AG, HIST1H2AC, HIST3H2A, HIST1H2AB, RAP2A, SRGN, TROVE2, RRAS, HLA-A, BCL2, TXN, CTSA, PRKARIA, ESD, HSPD1, CLU, HAPLN1, HSPA5, LAMC1, HSPA8, SLC2A1, SLC2A3, SLC2A14, UMPS, PYGB, RALA, SPTB, LAMP1, G6PD, DMD, IGF2R, ADH5, PRPS2, PCNA, COL11A1, COL6A1, COL6A2, COL6A3, PIP, ANXA3, ACTN1, SRC, PEPD, GP1BB, LAMP2, RNH1, BMP1, NCAM1, VCAN, VCAN, VCAN, ITGA4, EEF2, PDIA4, P4HA1, TPT1, F3, PLS3, PRKAR2A, MIF, CD99, HGF, FDPS, CPM, NID1, DARS, JUP, AKR1A1, PKM, PKM, PKM2, HSP90B1, IDE, DARS, JUP, AKR1B1, ANPEP, PVR, RAC2, MYOD1, B4GALT1, EZR, UCHL3, CD46, CD46, NME1, VEGFA, DSP, TIMP2, CBR1, HLA-A, PDGFRA, ATP2A2, FAH, HSPA6, RHOQ, GOT1, PRKCA, ITGA2, GJA1, PRKACB, PRKACA, KIN27, PRKACG, CAPN2, GAP43, HLA-G, CTPS1, ENG, PFKL, GM2A, LGALS3, IGFBP3, FLT1, TCP1, IGFBP2, ITGB5, ARF4, RPL7, VCL, PGAM1, SDC1, CDH2, GNAZ, VCAM1, NCL, GGT1, GGT3P, GGT2, SRM, CSNK2A2, ATP2B1, EIF2S2, RAB3A, RAB3B, RAB4A, RAB6A, RAB6B, NPR2, PSMB1, COL5A1, PTMS, GSTM3, ATP6V1B2, ATP6V1C1, CSRP1, FLNA, ACO1, IRP1, S1PR1, TNFAIP3, NT5E, TBXA2R, VDAC1, BGN, COMT, TGM2, OSBP, GART, PAICS, UBA1, NME1-NME2, NME2, NME1, ENPP1, HNRNPA2B1, IGFBP4, FBLN1, ITGA6, PPIB, WARS, RPS3, JAK1, PTPRG, AHCY, CFL1, ATP2B4, LAMA2, EEFIB2, IGFBP5, ACP1, TNC, MYL9, F2R, AZGP1, RPS12, FAS, DNAJB2, PSMA1, PSMA2, PSMA3, ITGA3, PTX3, MSN, DDX6, CTNNA2, S100A4, MGAT1, PTBP1, TARS, VARS, EEFIG, STOM, YWHAQ, MARK3, ATP6VOC, DPP4, RPL10, COL8A1, CD82, CALR, PSMB8, PSMA5, PSMB4, PSMB6, PSMB5, LOX, MAPK1, LAP3, TPP2, IMPA1, CTGF, EPHA2, EPHB2, SHC1, SHC2, CRABP2, MARCKS, GNA11, PRDX6, BLVRB, PRDX5, DDT, DDTL, PRDX3, RPL12, ECHS1, CMPK1, PEBP1, BDKRB2, HLA-A, HLA-A, HLA-B, HLA-C, HLA-C, ADSS, LRPAP1, ADSL, SLC7A1, LCN1, LCN1P1, CORO1A, GDI1, S100A7, SDC4, DNAJA1, ATIC, CASP14, YWHAB, YWHAB, SFN, STIP1, S100A11, PRDX2, CCKAR, GBP1, STX2, KIF5B, ABCC1, RNASE4, SDC2, CD68, HSPA4, GPC1, CTNNA1, CTNNB1, SERPINB6, NF2, RDX, SPR, PTGS2, THBS2, KRT9, FBN1, MYH9, BSG, BSG, TIMP3, GLRX, KRT2, PSMC2, SLC16A2, CHI3L1, GGT5, ARL2-SNX15, ARL2, ARL3, MAP2K2, MAP2K1, RPL4, PGM1, GNL1, SERPINF1, TGFBR2, HPCAL1, HPCA, TAGLN2, TALDO1, HSPA9, RPS19, RPL3, COL15A1, COL18A1, CAPG, IL6ST, CCT6A, NNMT, MDH1, EIF2S3, EIF2S3L, CD200, WNT5A, CSK, GARS, STAT1, ECE1, SLC1A3, SLC1A1, SLC1A4, PAFAH1B1, PTGIR, MCAM, RANBP1, NAMPT, NAMPTL, PSMC4, PPIC, VDAC2, USP5, MAPK9, MAPK10, CRKL, GSTM5, BDKRB1, RPL5, RPS9, MAP1B, NEDD4, UTRN, IQGAP1, RABIF, CAPZA2, CAPZB, EIF1AX, EIF1AY, RPL29, XDH, SLC6A8, LIMS1, GLIPR1, CXCL12, PREP, TFPI2, GCLM, CD151, PSMD8, GSS, CCT5, CSNKIA1, CSNKIA1L, CD97, MARCKSL1, DNASE1L1, ALDH9A1, RPL34, LMAN1, FASN, CCT3, TUFM, ALDH7A1, AARS, SARS, PSMB3, PSMB2, THBS3, ACADVL, TMED10, HINT1, RGS19, GSK3B, NT5C2, GMPS, GNAQ, GNG10, MMP14, SLC26A2, SERPINB8, SERPINB9, SERPINH1, PDLIM4, VASP, DNM2, BCAM, CCT8, ANXA11, RAB5C, RAB7A, RAB13, RAB27A, PLCD1, DUSP3, BCAP31, TPMT, CAV2, PLXNA3, VAMP7, ADCY7, AKR1D1, LUM, RAPIGDS1, SLC7A2, SMS, EFNB2, STC1, THOP1, CAPZA1, BLVRA, ARFIP1, ACLY, PGGT1B, COPB1, COPA, SLC5A3, SLC16A1, IST1, SUB1, RARS, CACNA2D1, YARS, USP14, HSPA2, BCAT1, ATP12A, ATP1B3, RAD23B, EPHB4, GAS1, ALDH18A1, NAPA, MFAP2, EIF5, SLC12A2, CSE1L, VCP, ADK, LAMB2, CDH11, CDH13, SEC13, HNRNPH2, EIF3B, FCGRT, BID, ITGA1, EIF6, ANTXR2, CD81, TPI1, ACTB, EIF4A1, RPS20, PRPS1, S100A10, CDC42, DSTN, RAB8A, SPCS3, RAB2A, RAB5B, RAB10, UBE2D3, UBE2D2, UBE2M, UBE2N, RAB14, ACTR3, ACTR2, ACTRIA, COPS2, RAP1B, RAP2B, RPS3A, RPL15, RPL27, RHOA, VBP1, STXBP1, UFM1, NUTF2, HNRNPK, YWHAG, RPS7, PPP1CA, PPP1CB, NCS1, PSMC1, PSMC5, RPS8, YWHAE, RPS14, RPS18, RPS29, RPS11, SNRPE, LSM3, TMSB4XP4, TMSB4X, ARF6, PSMC6, RPL7A, ETF1, CNBP, RPS4X, RPS4Y1, RPS4Y2, PPP2CB, ACTA2, ACTG2, RHOB, RPS6, HIST1H4A, RPL23, RAP1A, RPS25, RPS26P11, RPS26, RPS28, GNB1, GNB2, RPL10A, RPL11, PPIA, FKBP1A, RPS27A, UBB, UBC, UBA52, UBBP4, GRB2, RAC1, AP2B1, GNAS, GNAS, GNAS, GNAI1, YWHAZ, PPP2R2A, PPP2R2D, DYNLL1, DYNLT1, GNG5, RPS21, GNB2L1, ACTG1, TMSB10, PPP2CA, YBX1, CSNK2B-LY6G5B-1181, CSNK2B, TPM4, ACTC1, ACTA1, ACTG2, UBE2L3, EEF1A1, EEF1A1P5, TUBA1B, KLK9, TUBB4B, PAFAH1B2, HBB, SIRPA, SIRPB1, PIP4K2B, CSNK1G2, GSTO1, ADAM17, SRPX, BASP1, DCD, SMAD3, ARF1, ARF3, ARF5, RHOG, MXRA7, TNFAIP6, DAB2, HSPG2, EFNB1, ATP8B2, HDLBP, CDK6, CDK5, CLTC, FKBP3, HNRNPU, SPTBN1, SET, FABP5, CAP1, CAP1, SLC7A5, PFKP, OCRL, PLCB3, ROR2, TAGLN, DSG1, MAP2K1, TEK, FKBP4, NUCB1, RPL6, AKAP12, GNA12, CAV1, TNFAIP2, PLAUR, GBE1, NOTCH2, GLO1, ACVR1, YWHAH, PLP2, PRKCD, PTPN11, GFPT1, FMOD, PRDX1, C1QBP, CKAP4, ENPEP, COL16A1, SPAG1, BAX, LRP1, ARHGAP1, TGM3, DHX9, CRYZ, LGALS3BP, LOXL1, MFGE8, MFGE8, DSC1, SPOCK1, VAC14, AHNAK, SMAGP, GALNT2, AP1B1, BST2, ST3GAL1, SCRN1, KIAA0196, TWF1, ASPH, EFEMP1, FSTL1, STX4, DPYD, FAP, AIMP1, ILF3, PTPRJ, DLG1, MYO1E, PTP4A2, ABR, ARHGAP5, STRN3, STRN4, FLII, COASY, SPP2, PRKAA1, PPFIA1, PPFIA3, PPFIA2, PPFIA4, PAK2, PSMD2, DNAJC3, PAPPA, PTK7, SGCG, SLC14A1, EIF3I, PLD1, DYNC112, BTN1A1, ILK, SNTB2, SLC39A6, PDAP1, ADAM9, ROCK1, TCIRG1, PICALM, TUBB3, CAMK2G, CAMK2B, NAE1, CUL1, CUL2, CUL3, CUL4A, RAB31, RAB32, TPBG, FHL1, FHL3, ALCAM, PKP1, BMPR2, TUBB2A, TUBB2B, IDI1, PRKG1, CKAP5, COTL1, SCARB2, NID2, DAG1, DSG2, SCRIB, TTLL12, DPYSL3, DYNC1H1, CTTN, FLOT2, FLNC, FZD2, GNA13, GAMT, GALE, LRRC32, FAT1, DSC3, INPP5A, TRIP12, GANAB, RFTN1, MVP, LASP1, PTGR1, RAB39A, KPNB1, NAA25, VEPH1, CHMP4A, PSMD6, Sep-02, SNX17, RAB3GAP1, SLC39A14, KARS, EIF4H, POSTN, PCOLCE, PLCB4, PLEC, PPA1, STK38, PTPRK, RASA2, RAB35, LLGL1, PCBP1, RHEB, RSU1, TGFBI, TRIP10, TRIP6, MAPRE1, MYLK, SLC1A5, SMAD1, STXBP2, ZNF14, VAMP3, VAMP2, ATP6AP1, RAB11B, RAB11A, ZYX, ADRM1, CCDC6, UAP1, IGFBP7, LAMA4, EXT1, PSMD5, PKN2, DDB1, DPYSL2, SYPL1, SGCB, ECM1, DBN1, PTGIS, FSCN1, ATP2B3, CA9, MEP1A, DDR2, UGP2, TMEM132A, INF2, KIF26B, QRICH1, LEPRE1, DAK, SERPINB12, TUBB8, PREPL, TBC1D10B, ANO6, SVEP1, TMEM119, FNDC1, RFTN2, TP5313, PLEKHO1, ALF, STON1, CYBRD1, NAALADL2, HSP90AB4P, HSP90AB2P, HERC4, TMEM67, DPCD, VPS16, COLEC12, DNMBP, LDL-RAP1, OTUD7B, OTUD7A, WASF1, TPRG1L, SH3BGRL3, SLC39A1, UBR4, C9orf64, KPRP, XP32, TM9SF3, OGFRL1, SPO11, STRIP1, STRIP2, FAM171A1, BROX, FAM208B, PEAR1, ARHGEF2, RRAGB, RRAGA, RAB18, CD276, STEAP3, HGSNAT, MBLAC2, ARHGAP17, NXN, VASN, PTRHD 1, LAMTOR1, TWF2, RAB12, TENM4, PTRF, CC2D1A, FAHD2A, FAHD2B, CNNM4, FAM171B, TLDC1, RHBDF2, TRAF7, CSPG4, MOXD1, LRSAM1, HHIPL2, PI16, FAT4, PACS1, CD109, C1QTNF1, FAM65A, ANKRD13D, RASSF6, UBN2, LHFPL2, VPS13C, MOB3C, UBE2R2, TUBA1A, TUBA1C, TUBA3C, TUBA3E, TUBA8, CCDC80, BTN2A1, SND1, BZW1, EIF3M, CYFIP1, TAOK1, MOBIB, CHMP1B, ZC3HAV1, NEGR1, LIMS2, GOLGA7, PODN, SRGAP1, HUWE1, TMEM179B, AMIGO2, TMEM55B, TTC7B, PHLDB1, TXNDC5, SERINC5, VPS36, CAND1, TMEM200A, PPFIBP1, SBF2, SBF1, TICAM2, TMED7, TICAM2, XYLT1, STX12, AEBP1, PLD3, LIX1L, AHNAK2, CCDC50, SLITRK4, SLC44A2, SLC44A2, WDFY1, TEX2, FAM114A1, DCUN1D3, LRRC8A, SULF1, UBR1, UEVLD, CMIP, EXOC8, SLC6A16, ANKRD13A, UNC5B, SPG20, LRRC47, LYPD1, DOS, SLC35F6, C2orf18, ARHGAP18, ASCC3, EHBP1L1, PLCD3, SFRP1, MINK1, FAM26E, SLC15A4, ADAMTSL1, CCNYL1, ENAH, BMPER, DCBLD1, TDRD5, ATP11C, GOLM1, FAM63B, FAM63A, SERBP1, APOA1BP, CCNY, LRRN4CL, MAPKIIP1L, APPL2, GPRC5A, STXBP6, TSPAN14, SVIP, VANGL1, WDR48, NDNF, UBA3, TMEM167A, SPPL2B, HM13, CD99L2, PLEKHO2, NEK7, MICAL1, DTD1, IPO4, PPP4R1, UBASH3B, LRRC15, FRS2, RAB2B, PPP1R13L, CEMIP, PDCD6IP, UBTD2, FBLIM1, BRK1, SLC38A5, PHLDA1, SNX33, UBLCP1, APH1B, C1orf85, SLC44A1, PALLD, TTN, OVCA2, DDX1, PIEZO1, SLC7A6, GBF1, NCSTN, TM9SF4, NDRG1, HSPH1, GCN1L1, PXDN, SGCD, PVRL2, PVRL2, RABGGTA, HTRA1, ARPC1A, STAM, HAS2, GGH, NEO1, OSTF1, GLG1, UPF1, COPS5, RAB8B, RIT1, TNPO1, NINJ1, DVL3, USP9X, USP9Y, CUL5, LPP, PTP4A1, SCAMP4, IGSF8, ERGIC1, SYAP1, FERMT2, LRRC59, MRGPRF, AIDA, ARL8A, ARL8B, MOB3A, DOCK10, EFHD2, EFHD1, PPP1R14B, LIMK2, RHBDF1, CTHRC1, ISOC1, KCTD 12, SHISA4, CMBL, RSPRY1, L3HYPDH, CNRIP1, DYNLL2, CPNE2, S100A16, PERP, CHMP6, PGM2, SCARF2, PDLIM5, ERO1L, GMPPA, ITCH, KIRREL, LRIG1, LOXL4, DCHS1, MEGF 10, EXOC2, CNDP2, SNX27, IFT74, DOCK7, LRRC7, IPO9, DCBLD2, GPR124, FMNL2, TRNT1, TMEM237, GSDMA, SLC38A2, VPS35, PURB, PANX1, SNX18, NUDCD1, ERBB2IP, C16orf13, MYADM, FAM129B, PSMB7, PSMD1, PFDN5, PARK7, VAT1, S100A13, TTC1, DNAJC7, C12orf57, OSMR, CHP1, HSD17B10, NAP1L4, TM9SF2, CCT7, AGPAT1, PKP2, SH3GL1, GDF15, ARPC5L, PDCD1LG2, TMEM47, CORO1B, CPPED1, VPS25, MXRA8, SDF4, MIEN1, PELO, ERP44, LXN, ESYT1, MARVELD1, CCM2, COPS4, DCTN5, LRRC1, TUBB6, PDCD10, BDH2, NTMT1, TMED9, ACAT2, JAM3, RAB11FIP5, TBC1D10A, NAA15, SLC12A9, APIM1, ITPA, CADM1, FRMD8, ULBP3, ULBP2, FAM129A, ZDHHC5, TTYH3, TINAGL1, C20orf27, TOLLIP, ARL6, ITFG3, WNT5B, MESDC1, EHD4, C1orf21, TRIOBP, SLK, TAOK3, SLC12A5, SLC12A7, C11orf68, TXNIP, ACBD3, UNC45A, DNAJC5, CHMP4B, RNPEP, SMOC1, EPB41L1, GLIPR2, EHD1, CDCP1, CLMP, EPS8L2, ANTXR1, SH2D4A, DOCK5, ATP13A3, UBE2Z, FAM188A, MOB1A, GORASP2, C6orf211, LRRC40, SLC52A2, PPCS, UBTD1, SMURF2, GNB4, BCL2L12, CACYBP, RRAGC, RRAGD, PARVB, PROK2, GLOD4, ANKH, VAT1L, EPB41L5, EPB41L4B, CSNKIG1, CD248, S100A14, MYO10, NRXN3, VTA1, TNFRSF12A, IL1RAP, RIC8A, PLCB1, TIGAR, HINT3, NIT2, PVRL3, MYO5C, PDLIM7, SARIA, NANS, MXRA5, SLC17A5, OLFML3, OSTC, CDC42SE1, HEBP1, VPS45, PHPT1, SERINC1, ARHGAP35, PLSCR3, TMEM256-PLSCR3, LANCL2, STARD5, ATG3, ECHDC1, LIN7C, FAM49B, NUDT15, EXOC1, TMEM30A, EVA1B, TMEM51, COMMD8, RAB20, CMTM6, ARL15, ACTR10, IGF2BP1, HSPBP1, MYOF, EHD3, EHD2, CD274, FLRT3, LMCD1, MPP6, CHMP5, VAPA, SH3BP4, VPS18, DIP2B, TENM3, PTGFRN, PCDH10, RRBP1, ANKIB1, ANKFY1, ATXN10, NCDN, MRC2, CRNN, GNG12, TNFRSF10D, SPAST, GULP1, GRHPR, CTSZ, CKLF, CTNNAL1, PEF1, DNAJB4, STK39, ADD3, ABCF2, SLC23A2, TES, SUSD2, LAMTOR3, NPC1L1, CHORDC1, TMEM2, PFDN2, SLCO3A1, LNPEP, NAGK, ANXA10, DBNL, DCTN4, VPS28, LSM7, PACSIN3, TRHDE, ANGPTL2, ITGA11, CDV3, RAB21, RAB22A, PSME2, RAB23, MCTS1, ZDHHC8, SLC39A10, ASAP1, HEG1, ANKRD50, TBC1D24, CORO1C, PYCARD, NOTCH3, ICAM5, UBQLN1, SNX12, VPS4A, PCDHGC3, STUB 1, PACSIN2, STX8, PLA2G2D, PSMD13, PROCR, ABCG2, COPS3, TTF2, FZD1, SLC7A11, WASF3, SHOC2, PA2G4, CHMP2B, GNE, C14orf166, RUVBL1, NUDC, CFL2, ITM2B, SLC5A6, NCKAP1, EXOC6B, DIP2C, STK38L, EPB41L3, FAN1, LAMTOR2, TMA7, AP3M1, AP3M2, MEMO1, LSM2, SH3GLB1, CAB39, SBDS, PPIL1, UFC1, RTCB, FBXO7, RAP2C, TLN1, DAAM1, PLXND1, IRS2, LOXL2, RNF114, PPME1, PCDHGB7, PCDHGB6, PCDHGB5, PCDHA9, PHLDA3, GMPPB, TRPV2, CDC42BPB, IER3IP1, SNX9, SNX8, HEBP2, PSAT1, F11R, GPC6, NPTN, DKFZp566H1924, COPG1, LHFP, CLIC4, CFAP20, EMILIN1, DYNC1LI1, EPN1, CSNKIG3, SLC30A1, SLC4A7, ROBO1, SLC4A4, FCGBP, PCLO, CAPN7, WASF2, and combinations thereof. In some cases, proteins that contribute to therapeutic efficacy or that mediate paracrine signaling to effect therapeutic efficacy comprise CD39, CD39L3, and/or CD73. In some cases, proteins that contribute to therapeutic efficacy or that mediate paracrine signaling to effect therapeutic efficacy comprise CD39. In some cases, proteins that contribute to therapeutic efficacy or that mediate paracrine signaling to effect therapeutic efficacy comprise CD39L3. In some cases, proteins that contribute to therapeutic efficacy or that mediate paracrine signaling to effect therapeutic efficacy comprise CD73. In some cases, exosomes disclosed herein deliver one or more of the above proteins to reduce inflammation. Some exosomes deliver proteins that affect local ATP, ADP and/or AMP concentrations, for example by catalyzing the transformation of ATP into ADP, AMP or free purine, so as to reduce at least one of ATP concentration, ADP concentration and AMP concentration. Alternately or in combination, some exosomes deliver proteins that increase free purine concentration, for example by converting at least one of ATP, ADP and AMP to free purine. Conversion of ATP, ADP and AMP to free purine is accomplished in some cases through a combination of proteins comprising CD39 and CD73. Alternately, in some cases a single enzymatic activity releases free purine from at least one of ATP, ADP and AMP. Some exosomes deliver an enzyme having at least one of ATPase, ADPase, AMPase, and adenosine depurinase activity. In various embodiments, exosomes comprise not more than 2, 3, 4, 5, 6, 7, 8, 9, 10, 15, 20, 30, 40, 50, 60, 70, 80, 90, 100 or more than 100 proteins from the above list. In various embodiments, exosomes comprise at least 2, 3, 4, 5, 6, 7, 8, 9, 10, 15, 20, 30, 40, 50, 60, 70, 80, 90, 100 or more than 100 proteins from the above list. In various embodiments, exosomes comprise not more than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list. In various embodiments, exosomes comprise not less than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list. In various embodiments, not more than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list are purified, for example from exosome compositions, for treatment of disease. In various embodiments, not less than 1%, 2%, 3%, 4%, 5%, 6%, 7%, 8%, 9%, 10%, 15%, 20%, 30%, 40%, 50%, 60%, 70%, 80%, 90%, 95%, 99%, or 100% of the proteins from the above list are purified, for example from exosome compositions, for treatment of disease. In some cases, purified proteins from the above list are combined with exosome compositions, for example using the exosomes as a delivery mechanism, for treatment of disease.

Some exosome compositions disclosed herein comprise nucleic acids, such as miRNAs that contribute to therapeutic efficacy, or that mediate paracrine signaling to effect therapeutic efficacy. In some aspects, the composition comprises microRNAs (miRNAs). miRNAs include but are not limited to let7b miRNA. In some aspects, exosomes-derived miRNAs are delivered to lymphocytes to induce a regulatory phenotype. In some aspects, the miRNAs are delivered to lymphocytes to induce a regulatory Foxp3+ phenotype. In some aspects, the miRNAs are delivered to macrophage to induce a regulatory M2 macrophage phenotype. In some aspects, the miRNA let-7b is delivered to macrophage to induce a regulatory M2 macrophage phenotype. In some aspects, the composition comprises at least one category of molecule such as exogenous RNAs, proteins, antigens and microRNAs that produce an immune-stimulatory, pro-inflammatory response from a host immune system. In some aspects, the composition comprises exogenous stimulatory antigens that produce an immune-stimulatory, pro-inflammatory response from endogenous tumor infiltrating lymphocytes (TILs) in a liquid or solid tumor. In some aspects, the composition comprises exogenous stimulatory antigens that produce an immune-stimulatory, pro-inflammatory response from endogenous tumor infiltrating lymphocytes (TILs) in a liquid or solid tumor in concert with inhibitors of lymphocyte checkpoint pathways. In some aspects, the composition comprises exogenous stimulatory antigens that produce an enhanced co-stimulatory, pro-inflammatory response from endogenous tumor infiltrating lymphocytes (TILs) in a liquid or solid tumor, in concert with antibody, bi-specific antibody or chemical inhibitors of lymphocyte checkpoint pathways such as CTLA4, PD1, PDL1, LAG3, PDL2 or CD39 pathways. In some aspects, the composition comprises exogenous stimulatory antigens that produce an immune-stimulatory, pro-inflammatory response from exogenous engineered T lymphocytes targeted to a liquid or solid tumor. In some aspects, the composition comprises exogenous stimulatory antigens that produce an immune-stimulatory, pro-inflammatory response from exogenous dendritic cells (DCs) targeted to a specific solid tumor antigen. In some aspects, the composition comprises exogenous co-stimulatory antigens that produce an immune-stimulatory, pro-inflammatory response from exogenous engineered natural killer (NK) cell targeted to a solid or liquid tumor.

A therapeutically active exosome composition such as a paracrine signaling exosome composition disclosed herein, in some cases, comprises an immunosuppressive drug. Immunosuppressive drugs contemplated herein include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Some exosome compositions comprise anti-TNF antibodies, including but not limited to infliximab, adalimumab, certolizumab, and golimumab. Exosome compositions comprise TNF inhibitors including but not limited to etanercept, xanthine derivatives, and bupropion. In some cases, exosome compositions comprise at least one NSAID. In some cases, exosome compositions comprise at least one steroid.

Methods of Treatment

Exosome compositions disclosed herein include therapeutic compositions for methods and uses in treatment of disease, in some cases via paracrine signaling activity. Some exosome compositions modulate an inflammation response in a mammal. Therefore, disclosed herein are methods of modulating an inflammation response in a mammal by administering at least one purified SDC2+ exosome compositions to the site of the inflammation response. Also disclosed herein are purified SDC+ exosome compositions for use in modulating an inflammation response in a mammal by administering at least one purified SDC2+ exosome composition to the site of the inflammation response. Also disclosed herein are purified SDC2+ exosome compositions for use in preparation of a medicament for modulating an inflammation response in a mammal by administering at least one purified SDC2+ exosome composition to the site of the inflammation response. Methods and uses include various routes of administration known to reach sites of inflammation, which vary depending on the inflammation response which requires treatment. Routes of administration include but are not limited to parenteral (including subcutaneous, intravenous, intra-arterial, intraosseous, intracerebral, intracerebroventricular, intrathecal, intramedullary, intra-articular, intramuscular, or intraperitoneal injection), rectal, respiratory or inhalation, topical, transdermal, and oral (for example, in capsules, suspensions, or tablets). For some indications, it is desirable to administer exosome compositions such as paracrine signaling exosome compositions disclosed herein via intravenous administration. In particular, intravenous administration is often preferred to deliver exosome compositions or compositions derived from exosomes to a mammalian lung such as a human lung.

For some indications, it is desirable to administer exosome compositions such as paracrine signaling exosome compositions disclosed herein via a respiratory or inhalation route using an inhalation device. An inhalation device is capable of administering therapeutic compositions to the respiratory airways of a patient. Inhalation devices include conventional inhalation devices such as metered dose inhalers, dry powder inhalers, jet nebulizers, ultrasonic wave nebulizers, heat vaporizers, soft mist inhalers, and high efficiency nebulizers. Nebulizers, metered dose inhalers, and soft mist inhalers deliver therapeutics by forming an aerosol, which includes droplet sizes that can easily be inhaled. A patient within the bounds of an inhalation therapy can use the aerosol. A nebulizer is able to turn a therapeutic or medication into a fine aerosol mist that is delivered to the lungs of an individual.

Nebulizers include high efficiency nebulizers. High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. In some embodiments, the high efficiency nebulizer also utilizes one or more actively or passively vibrating microperforated membranes. In some embodiments, the high efficiency nebulizer contains one or more oscillating membranes. In some embodiments, the high efficiency nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. Still yet, in some embodiments, the high efficiency nebulizer contains a pulsating membrane. In some embodiments, the high efficiency nebulizer is continuously operating.

For some indications, diseases or disorders, it is desirable to administer exosome compositions such as paracrine signaling exosome compositions topically (e.g., applied directly to the skin of the individual being treated). In some cases, topical administration is used to treat diseases of the skin. Topical administration includes epicutaneous administration. Exosome compositions for topical administration are formulated specifically to be administered to the skin. Such topical exosome compositions include but are not limited to solutions, lotions, creams, ointments, gels (including hydrogels or collagen gels), foams, transdermal patches, powders, pastes, and tinctures. In some cases, exosome compositions comprise a hydrogel or a collagen gel.

Certain indications, diseases, or disorders benefit from administration of exosome compositions such as paracrine signaling exosome compositions to the eye (e.g., intraocular or ophthalmic). Exosome compositions for administration to the eye comprise formulations (e.g., buffers or excipients) known by one of skill in the art to be appropriate to the eye.

Injection of exosome compositions such as paracrine signaling exosome compositions to a subject is effective in treating certain indications, diseases, or disorders. Delivery of an exosome composition via injection includes but is not limited to injection to the lymph nodes, subcutaneous injection, intramuscular injection, intravenous injection, intraperitoneal injection, intrathecal injection, intradermal injection, intraarticular injection, and other injection methods known by one of skill in the art. Exosome compositions for injection comprise formulations or physiologically acceptable buffers or excipients for injection.

Certain indications, diseases, or disorders benefit from administration of exosome compositions such as paracrine signaling exosome compositions directly to the heart. Direct cardiac application of exosome compositions such as paracrine signaling exosome compositions include but are not limited to intra-cardiac, intra-pericardial, or intra-coronary artery injection.

Exosome compositions such as paracrine signaling exosome compositions used in methods of treatment and uses in a mammal, in some cases, include one or more antigens. In methods of treatment and uses where the exosome composition includes one or more antigens, the antigen is not exposed to the individual's humoral immune system. In these cases, the individual does not develop a humoral immune response to the antigen.

Exosome compositions such as paracrine signaling exosome compositions used in methods of treatment and uses in a mammal comprise SDC2 or are SDC2+. When the exosome composition is analyzed, at least 20% of the exosomes comprise SDC2. In some cases, the exosome composition used in methods of treatment and uses comprise a composition where at least 30%, 40%, 50%, 60%, 70%, 80%, 90%, 95%, 99%, or more of the exosomes comprise SDC2. The proportion of exosomes in the composition comprising SDC2 is determined by immunofluorescence, for example flow cytometry, electron microscopy, or other method known by one of skill in the art.

While exosome compositions such as paracrine signaling exosome compositions described herein, in some cases, are derived from cells, the exosome compositions do not comprise living cells. The exosome compositions, therefore, are non-tumorigenic, that is, they do not increase the susceptibility of a subject to developing a tumor or cancer.

Methods of treatment and uses disclosed herein comprise administering to a mammal an exosome composition comprising exosomes, for example paracrine signaling exosomes or in vitro exosomes, and SDC2+ mesenchymal stem cells (e.g., SDC2+ mesenchymal stromal stem cells). In some instances, methods of treatment and uses use exosome compositions that include compositions comprising exosomes or in vitro exosomes and regulatory T cells. Regulatory T cells include CD25+ regulatory T cells, CD4+ regulatory T cells, FoxP3+ regulatory T cells, CD25+CD4+ FoxP3+ regulatory T cells, and combinations thereof. In some instances, methods of treatment and uses that use exosome compositions include compositions comprising in vitro exosomes, SDC2+ mesenchymal stem cells, and regulatory T cells.

Methods of treatment and uses disclosed herein use exosome compositions such as paracrine signaling exosome compositions that retain potency or activity after being frozen or cryopreserved without the use of a cryoprotectant. Cryoprotectants include DMSO, glycerol, polyethylene glycol, propylene glycol, glycerine, polyvinylpyrolidone, sorbitol, dextran, and trehalose. The exosome compositions used in methods of treatment and uses also retain potency after being frozen without using special freezing protocols. Special freezing protocols include flash freezing, programmable rate freezer, and freezing in an insulated container. The exosome compositions used for methods of treatment and uses are frozen in buffer or culture media. Buffers include physiologically acceptable buffers such as phosphate buffer, histidine buffer, citrate buffer, acetate buffer, and other buffers known by those of skill in the art. In some cases, methods of treatment and uses herein use exosome compositions are lyophilized or have been lyophilized.

Methods of treatment and uses disclosed herein comprise administration of compositions comprising exosomes such as paracrine signaling exosomes in a therapeutically effective amount, which would be known by one of skill in the art. Administration of a therapeutically effective amount of exosomes, in some cases, comprises administration of $10^6$-$10^8$ exosomes, for example $10^6$, $10^7$, $10^8$, or more exosomes of the composition. In some cases, administration of a therapeutically effective amount of exosomes comprises administration of 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Methods of treatment and uses include administration of exosome compositions, which in some cases, are concentrated to be diluted by the individual prior to administration. In some cases, methods of treatment and uses comprise administration of exosome compositions that are diluted and ready to be administered by the individual. In some cases, methods of treatment and uses comprise administration of exosome compositions that are contained in single use vials or syringes. In some cases, methods of treatment and uses comprise administration of a dose from a container comprising multiple doses.

Methods of treatment and uses disclosed herein comprise administration of exosome compositions such as paracrine signaling exosome compositions comprising proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin. Some methods and uses comprise administration of an enzyme having ATPase, ADPase, AMPase, or adenosine depurinase activity.

Methods of treatment and uses herein, in some cases, comprise administration of a therapeutically active exosome composition such as paracrine signaling exosome composition that comprises an immunosuppressive drug. Non-limiting examples of immunosuppressive drugs used in exosome compositions for treatment include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Exosome compositions for methods of treatment and uses comprise anti-TNF antibodies, including but not limited to infliximab, adalimumab, certolizumab, and golimumab. Methods of treatment and uses comprise administration of exosome compositions that comprise TNF inhibitors including but not limited to etanercept, xanthine derivatives, and bupropion. Exosome compositions for methods of treatment and uses herein, in some cases, comprise NSAIDs. In some cases exosome compositions for methods of treatment and uses comprise one or more steroids.

Inflammatory diseases and disorders of the immune system are known by one of skill in the art to result because of an over activation or inappropriate activation of the immune system. One or more cell types in the immune system may contribute to inflammatory and immune disease, for example CD4+ helper T cells, CD8+ cytotoxic T cells, Th17 cells, dendritic cells, macrophages, mast cells, leukocytes, neutrophils, eosinophils, basophils, monocytes, and combinations thereof. Often these cells synergize and amplify the inflammatory response through cell derived mediators such as enzymes, cytokines, chemokines, and other immune mediators. Immune mediators include but are not limited to lysosome granules, histamine, IFNγ, IL-8, leukotriene B4, nitric oxide, prostaglandins, TNFα, IL-1, IL-13, IL-17, IL-2, and combinations thereof. Acute inflammation is a necessary component of the immune response to disease; however, chronic inflammation generally leads to inflammatory disease resulting in tissue destruction by inflammatory cells. In some cases, inflammation is caused, at least in part, by increased extracellular ATP at the site of inflammation. In some cases, exosome compositions such as paracrine signaling exosome compositions disclosed herein, reduce extracellular ATP thereby reducing inflammation. In some cases, inflammation is caused, at least in part, by increased extracellular ADP at the site of inflammation. In some cases, exosome compositions such as paracrine signaling exosome compositions disclosed herein, reduce extracellular ADP thereby reducing inflammation. In some cases, inflammation is caused, at least in part, by increased extracellular AMP at the site of inflammation. In some cases, exosome compositions such as paracrine signaling exosome compositions disclosed herein, reduce extracellular AMP thereby reducing inflammation. In some cases, inflammation is caused, at least in part, by increased extracellular adenosine at the site of inflammation. In some cases, exosome compositions such as paracrine signaling exosome compositions disclosed herein, reduce extracellular adenosine thereby reducing inflammation. In some cases, exosome compositions, such as paracrine signaling compositions reduce inflammation by delivery of at least one enzyme having ATPase, ADPase, AMPase, or adenosine depurinase activity. In some cases, exosome compositions, such as paracrine signaling compositions reduce inflammation by delivery of at least one of—or both of the CD39 and CD73 enzymes. While inflammatory diseases present with a variety of symptoms that depend on the tissue or organ affected by inflammation, some commonalities include pain, heat, redness, swelling, and loss of tissue or organ function. In some cases, exosome compositions prevent or reverse all or some of the above inflammatory responses.

Disclosed herein are methods of modulation of an inflammatory response in a mammal using exosome compositions. Also disclosed herein are exosome compositions for use in modulation of an inflammatory response in a mammal. Also disclosed herein are exosome compositions for use in preparation of a medicament for modulation of an inflammatory response in a mammal. An inflammatory response, in some cases, is an immune response. In some cases, an inflammatory response is an autoimmune response. Immune responses, inflammatory responses, and autoimmune responses, often lead to the development of diseases or disorders in need of treatment in a mammal. Diseases and disorders caused by an immune response, inflammatory response, or autoimmune response affect nearly every tissue of the body and are generally characterized by an overactive or otherwise inappropriate response by the immune system of a mammal. In some cases, the immune response, inflammatory response, or autoimmune response is from the adaptive immune system. In some cases, the immune response, inflammatory response, or autoimmune response is from the innate immune response. In some cases, the immune response, inflammatory response, or autoimmune response results in excess secretion of cytokines, cytotoxic T cell activity, antibody production, T cell proliferation, swelling, redness, fever, edema, or other response by a cell or tissue of the immune system. In some cases the immune response is mediated or alleviated by administration of an exosome composition such as an SDC2+ exosome composition such as a paracrine signaling exosome composition.

Disclosed herein are methods of treatment of an inflammation response or immune response comprising administration of an exosome composition. Also disclosed herein are exosome compositions for use in treatment of an inflammation response or immune response. Also disclosed herein are exosome compositions for use in preparation of a medicament for treatment of an inflammation response or immune response. The response includes but is not limited to sepsis, acute respiratory distress syndrome (ARDS), Crohn's disease, inflammatory bowel syndrome, rheumatoid arthritis, osteoarthritis, graft versus host disease, multiple sclerosis, amyotrophic lateral sclerosis, motor neuron disorders, Sjogren's syndrome, non-healing dermal wounds, bone fractures, concussion wounds, burns, cachexia, sarcophenia, Dermatomyositis, Fibromyalgia, Inclusion body myositis, Myositis, Myasthenia gravis, Neuromyotonia, Paraneoplastic cerebellar degeneration, Polymyositis, and combinations thereof. In some cases, the inflammatory response comprises an inflammatory liver disease. In some cases the inflammation response is mediated or alleviated by administration of an exosome composition such as an SDC2+ exosome composition such as a paracrine signaling exosome composition.

An inflammatory response in need of treatment using exosome compositions disclosed herein, in some cases, comprises a diabetic complication. Diabetic complications are often seen in individuals with diabetes. In some cases, the diabetic complications occur in individuals with type 1 diabetes. In some cases, the diabetic complications occur in individuals with type 2 diabetes. Diabetic complications include, but are not limited to atherosclerosis, nephropathy, cardiomyopathy, neuropathy, a kidney disorder, kidney failure, diabetic ulcers, leg ulcers, and other conditions known by one of skill in the art to occur in patients with diabetes. In some cases the diabetic complication is mediated or alleviated by administration of an exosome composition such as an SDC2+ exosome composition such as a paracrine signaling exosome composition. Upon exosome administration, such as SDC2+ exosome administration as disclosed herein, symptoms of the diabetic condition are ameliorated, such that some function is regained in some cases. Often, these benefits are observed in diabetic individuals without impacting blood glucose levels.

Exosome compositions disclosed herein, in some cases, are useful for treating or alleviating type 2 diabetes, also known as noninsulin-dependent diabetes mellitus or adult onset diabetes. Type 2 diabetes is known by those of skill in the art to be associated with increased systemic inflammation which reduces sensitivity to insulin in patients with type 2 diabetes. In some cases, systemic inflammation is associated with obesity, heart disease, atherosclerosis and metabolic syndrome. Symptoms of type 2 diabetes include but are not limited to fatigue, hunger, non-healing sores, heart disease, stroke, diabetic retinopathy, blindness, kidney failure, reduced blood flow, hyperosmolar hyperglycemia, and combinations thereof. Reduction of inflammation, by anti-inflammatory drugs or compositions, such as exosome compositions disclosed herein, reduce one or more symptoms and in some cases cure type 2 diabetes. In particular, exosome administration in some cases ameliorates diabetes-associated kidney damage, in some cases without impacting glucose levels in the exosome recipient.

In some cases, an inflammatory response in need of treatment using exosome compositions disclosed herein comprises a heart disorder. Heart disorders include but are not limited to myocarditis, postmyocardial infarction syndrome, postperiocardiotomy syndrome, and subacute bacterial endocarditis. In some cases the heart disorder is mediated or alleviated by administration of an exosome composition such as an SDC2+ exosome composition such as a paracrine signaling exosome composition.

In some cases, an inflammatory response in need of treatment using exosome compositions disclosed herein comprises a kidney disorder. Kidney disorders include but are not limited to anti-glomerular basement membrane nephritis, interstitial cystitis, and lupus nephritis. Some kidney disorders result from or are associated with diabetes such as type 1 diabetes or type 2 diabetes. In some cases the kidney disorder is treated, mediated or alleviated by administration of an exosome composition such as an SDC2+ exosome composition. An example of an SDC2+ exosome composition mediating a kidney disorder is a paracrine signaling exosome composition. Upon exosome administration, such as SDC2+ exosome administration as disclosed herein, symptoms of the kidney condition are ameliorated, such that some kidney function is regained in some cases. Often, these benefits are observed in diabetic individuals without impacting blood glucose levels.

In some cases, an inflammatory response in need of treatment using exosome compositions disclosed herein comprises a liver disorder. Liver disorders include but are not limited to autoimmune hepatitis, Primary biliary cirrhosis, and Primary sclerosing cholangitis. In some cases the liver disorder is mediated or alleviated by administration of an exosome composition such as an SDC2+ exosome composition such as a paracrine signaling exosome composition.

In some cases, an inflammatory response in need of treatment using exosome compositions disclosed herein comprises a lung disorder. Lung disorders include but are not limited to acute respiratory distress syndrome (ARDS), Antisynthetase syndrome, asthma, chronic obstructive pulmonary disease, cystic fibrosis, atelectasis, bronchitis, emphysema, pneumonia, and pulmonary edema. In some cases the lung disorder is mediated or alleviated by administration of an exosome composition such as an SDC2+ exosome composition such as a paracrine signaling exosome composition.

In some cases, an inflammatory response in need of treatment using exosome compositions disclosed herein comprises a skin disorder. Skin disorders include but are not limited to Alopecia Areata, Autoimmune Angioedema, autoimmune progesterone dermatitis, autoimmune urticaria, Bullous pemphigoid, Cicatricial pemphigoid, Dermatitis herpetiformis, Discoid lupus erythematosus, *Epidermolysis bullosa acquisita, Erythema nodosum, Gestational pemphigoid, Hidradenitis suppurativa, Lichen planus, Lichen sclerosus,* Linear IgA disease, *Morphea, Pemphigus vulgaris, Pityriasis lichenoides* et *varioliformis acuta,* Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. In some cases the skin disorder is mediated or alleviated by administration of an exosome composition such as an SDC2+ exosome composition such as a paracrine signaling exosome composition.

In some cases, an inflammatory response in need of treatment using exosome compositions disclosed herein, comprises a pancreas disorder. Pancreas disorders include but are not limited to autoimmune pancreatitis and diabetes mellitus type 1. In some cases the pancreatic disorder is mediated or alleviated by administration of an exosome composition such as an SDC2+ exosome composition such as a paracrine signaling exosome composition.

Exosome compositions disclosed herein, in some cases, are useful in treating or alleviating Diabetes mellitus type 1, also known as type 1 diabetes. Diabetes mellitus type 1 is known in the art to be caused by destruction of insulin secreting beta cells in the pancreas, at least in part, by autoreactive T cells. Symptoms of Diabetes mellitus type 1 include but are not limited to increased blood and urine glucose levels, polyuria (frequent urination), polydipsia (increased thirst), polyphagia (increased hunger), weight loss, diabetic ketoacidosis, nonketoic hyperosmolar coma, heart disease, stroke, kidney failure, foot ulcers, eye damage, and combinations thereof. In the latent autoimmune or early stage of diabetes, immunosuppression or reduction of the immune response, by anti-inflammatory drugs or compositions, such as exosome compositions disclosed herein, reverse, slow, and prevent increased destruction of the beta cells, leading to a reduction in one or more symptoms, and in some cases, a cure of the diabetes mellitus type 1. In particular, administration of an exosome composition such as an SDC2+ exosome composition in some cases treats, mediates, or ameliorates the symptoms of type 1 diabetes-related kidney disorders. In some cases this beneficial effect of exosome administration is independent of any impact on glucose levels of exosome administration.

In some cases, an inflammatory response in need of treatment using exosome compositions disclosed herein, comprises a thyroid disorder. Thyroid disorders include but are not limited to autoimmune thyroiditis, Ord's thyroiditis and Graves' disease. In some cases the thyroid disorder is mediated or alleviated by administration of an exosome composition such as an SDC2+ exosome composition such as a paracrine signaling exosome composition.

In some cases, an inflammatory response in need of treatment using exosome compositions disclosed herein, comprises an exocrine disorder. Exocrine disorders include but are not limited to a reproductive organ disorder, autoimmune oophoritis, endometriosis, and autoimmune orchitis. In some cases the exocrine disorder is mediated or alleviated by administration of an exosome composition such as an SDC2+ exosome composition such as a paracrine signaling exosome composition.

In some cases, an inflammatory response in need of treatment using exosome compositions disclosed herein, comprises a digestive system disorder. Digestive disorders include but are not limited to autoimmune enteropathy, Celiac disease, Crohn's disease, microscopic colitis, inflammatory bowel disease, and ulcerative colitis. In some cases the digestive system disorder is mediated or alleviated by administration of an exosome composition such as an SDC2+ exosome composition such as a paracrine signaling exosome composition.

In some cases, an inflammatory response in need of treatment using exosome compositions disclosed herein, comprises a blood disorder. Blood disorders include but are not limited to antiphospholipid syndrome, aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. In some cases the blood disorder is mediated or alleviated by administration of an exosome composition such as an SDC2+ exosome composition, in some cases an SDC2+ paracrine signaling exosome composition.

Often, an inflammatory response in need of treatment using exosome compositions disclosed herein comprises a connective tissue, multi-organ or systemic disorder. Connective tissue, multi-organ, or systemic disorders include but are not limited to adiposis dolorosa, Adult-onset Still's disease, Ankylosing Spondylitis, CREST syndrome, Drug-induced lupus, enthesitis-related arthritis, Eosinophilic fasciitis, Felty syndrome, juvenile Arthritis, Lyme disease (Chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, schnitzler syndrome, Systemic Lupus Erythematosus, and undifferentiated connective tissue disease. In some cases the connective tissue, multi-organ or systemic disorder is mediated or alleviated by administration of an exosome composition such as an SDC2+ exosome composition such as a paracrine signaling exosome composition.

In some cases, an inflammatory response in need of treatment using exosome compositions disclosed herein, comprises a nervous system disorder. Nervous system disorders include but are not limited to acute disseminated encephalomyelitis, acute motor axonal neuropathy, anti-N-methyl-D-aspartate receptor encephalitis, Balo concentric sclerosis, Bickerstaffs encephalitis, chronic inflammatory demyelinating polyneuropathy, Guillain-Barre syndrome, Hashimoto's encephalopathy, idiopathic inflammatory demyelinating diseases, Lambert-Eaton myasthenic syndrome, multiple sclerosis, pediatric autoimmune neuropsychiatric disorder associated with *Streptococcus*, progressive inflammatory neuropathy, restless leg syndrome, Stiff person syndrome, Sydenham chorea, Alzheimer's disease, Parkinson's disease, ALS, and transverse myelitis. In some cases, the nervous system disorder is mediated or alleviated by administration of an exosome composition such as an SDC2+ exosome composition such as a paracrine signaling exosome composition. In some cases, the nervous system disorder is a central nervous system disorder. In some cases, administration of an exosome composition such as a paracrine signaling exosome composition disclosed herein results in exosomes crossing the blood brain barrier thereby reducing inflammation in the brain.

In some cases, an inflammatory response in need of treatment using exosome compositions disclosed herein, comprises an eye disorder. Eye disorders include but are not limited to autoimmune retinopathy, autoimmune uveitis, Cogan syndrome, Graves's ophthalmopathy, intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. In some cases the eye disorder is mediated or alleviated by administration of an exosome composition such as an SDC2+ exosome composition such as a paracrine signaling exosome composition.

In some cases, an inflammatory response in need of treatment using exosome compositions disclosed herein, comprises an ear disorder. Ear disorders include but are not limited to autoimmune inner ear disease and Meniere's disease. In some cases the ear disorder is mediated or alleviated by administration of an exosome composition such as an SDC2+ exosome composition such as a paracrine signaling exosome composition.

In some cases, an inflammatory response in need of treatment using exosome compositions disclosed herein, comprises a vascular system disorder. Vascular system disorders include but are not limited to Anti-neutrophil cytoplasmic antibody-associated vasculitis, Behcet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, *Polyarteritis nodosa*, Polymyalgia rheumatica, Urticarial vasculitis, and Vasculitis. In some cases the vascular system disorder is mediated or alleviated by administration of an exosome composition such as an SDC2+ exosome composition such as a paracrine signaling exosome composition.

Methods of treatment and uses disclosed herein comprise identification of a patient or a group of patients for treatment by administration of exosome compositions such as paracrine signaling exosome compositions. Identification of a patient group, in some cases, is done by a physician or other healthcare professional. The physician or other healthcare professional uses criteria known by those in the medical field to determine whether an individual, patient, or group of patients is a candidate for treatment of an inflammation, immune or autoimmune response.

Methods of Isolation

Exosome compositions such as paracrine signaling exosome compositions disclosed herein are isolated or purified. The method of isolation or purification involves isolating exosomes from a population of stromal cells such as SDC2+ stromal cells. In some cases, methods of isolation or purification of exosome compositions comprise obtaining a cell population enriched for SDC2+ cells for isolation of the exosomes, recovering a supernatant from said cell population, and obtaining an exosome fraction from the supernatant. Exosome compositions, such as paracrine signaling exosome compositions disclosed herein, in some cases, express SDC2. In some cases, the SDC2 is found in the interior of the exosome. In some cases, the SDC2 is found on the exterior of the exosome. The method of isolation or purification results in an exosome composition comprising exosomes, wherein at least 20% of the exosomes comprise SDC2.

Stromal cells for methods of isolation or purification of exosome compositions such as paracrine signaling exosome compositions, in some cases, are modified to increase the yield of exosome compositions resulting from the isolation or purification method. In some cases, cells are genetically modified to overexpress SDC2. Genetic modification of stromal cells is accomplished by methods known by one of skill in the art and includes but is not limited to transfection of the stromal cells with one or more plasmids that comprise the SDC2 coding sequence and a promoter, such as a CMV, SV40, EF1a, or CAG promoter. Genetic modification of stromal cells, in some cases, is accomplished by infection of the stromal cells with a virus that comprises the SDC2 coding sequence and a promoter.

In some cases, stromal cells for methods of isolation or purification of exosome compositions such as paracrine signaling exosome compositions are genetically modified to overexpress a protein associated with controlling the cytoskeleton. In some cases, cells are genetically modified to overexpress cortactin. Genetic modification of stromal cells is accomplished by methods known by one of skill in the art and includes but is not limited to transfection of the stromal cells with one or more plasmids that comprise the cortactin coding sequence and a promoter, such as a CMV, SV40, EF1a, or CAG promoter. Genetic modification of stromal cells, in some cases, is accomplished by infection of the stromal cells with a virus that comprises the cortactin coding sequence and a promoter.

In some cases, stromal cells for methods of isolation or purification of exosome compositions such as paracrine signaling exosome compositions are irradiated to increase the yield of exosome compositions resulting from the isolation of purification method. Irradiation of cells is known by those of skill in the art and includes but is not limited to exposing the stromal cells to a source of radiation, such as an alpha radiation source, a beta radiation source, or a gamma radiation source. In some cases, stromal cells are irradiated using gamma-irradiation.

In some cases, stromal cells for methods of isolation or purification of exosome compositions such as paracrine signaling exosome composition are subjected to an inflammatory stimulus. Inflammatory stimuli include but are not limited to TNF-alpha, interferon-gamma, interferon-beta, interleukin-1b, TLR agonists, Poly I:C, and LPS.

In some cases, stromal cells for methods of isolation or purification of exosome compositions such as paracrine signaling exosome compositions are subjected to a growth arrest. Growth arrest is understood by those of skill in the art as slowing or stopping division of cells. Methods of growth arrest include but are not limited to irradiation, mitomycin-c, TGFb stimulation, and growing cells to confluence.

Methods of isolation or purification of exosome compositions such as paracrine signaling exosome compositions yield compositions comprising a specific proportion of exosomes that comprise SDC2. In some cases, the proportion of exosomes in the composition that comprise SDC2 is within a range of 20% to 99%. In some cases, method of isolation or purification results in an exosome composition where the proportion of exosomes in the composition that comprise SDC2 is at least 20%, 30%, 40%, 50%, 60%, 70%, 80%, 90%, 95%, 99%, or greater.

Methods of isolation or purification of exosome compositions such as paracrine signaling exosome compositions, in some cases, uses continuous production technology, such as hollow-fiber bioreactor technology. Hollow-fiber bioreactors (HFBRs) have high surface-to-volume ratios which support large numbers of cells at high densities. Exemplary HFBRs include but are not limited to FiberCell Systems and Terumo Quantum Cell Expansion System. Such systems can support from about 10^7 cells to about 10^8 cells. Advantages of HFBRs include but are not limited to a fiber with a molecular weight cutoff of 5-20 kDa which allows nutrients and waste products to pass through but exosomes are retained in the reactor and concentrated up to 100 times. Cells bound to the support do not require splitting as cell lines can grow to post-confluence without significant apoptosis. In some cases, collection of exosomes is maintained over several months of continuous production. All of these factors combine to allow exosomes to be secreted in large numbers and concentrated significantly in the small volume of the extracapillary space of the cartridge. Exosomes cannot cross the fiber in either direction so cell culture serum can be used in the circulating medium without contaminating the secreted exosomes within the extracapillary space of the cartridge.

Methods of isolation or purification of exosome compositions such as paracrine signaling exosome compositions result in an exosome composition that is free of living cells, in other words, the resulting exosome composition does not comprise a living cell. Isolation or purification of exosome compositions results in a composition that is non-tumorigenic. That is, the exosome composition obtained by methods of isolation or purification disclosed herein does not cause tumors or cancer to develop in a mammal that has been treated with or given one or more doses of the exosome composition.

Methods of isolation or purification result disclosed herein result in a stable composition. For example, the exosome composition such as paracrine signaling exosome composition obtained by the methods of isolation or purification is stable at room temperature (20 to 25° C.), at cold temperatures (3 to 5° C.), or freezing temperatures, (−150 to 0° C.). In some cases, stability is improved by the addition of specific buffers or excipients known by one of skill in the art. Non-limiting examples of excipients include sucrose, trehalose, polyethylene glycol, a polysaccharide, a carrier protein, an inert protein, dextran, hydroxyl ethyl starch (HETA), PEG-4000, gelatin, PLGA, Eudragit RS 100 Nanoparticles, and combinations thereof.

Methods of isolation or purification of exosome compositions disclosed herein result in an exosome composition that can retain potency or activity after being frozen or cryopreserved without the use of a cryoprotectant. Cryoprotectants include DMSO, glycerol, polyethylene glycol, propylene glycol, glycerine, polyvinylpyrolidone, sorbitol, dextran, and trehalose. The exosome compositions also retain potency after being frozen without using special freezing protocols. Special freezing protocols include flash freezing, programmable rate freezer, and freezing in an insulated container. The exosome compositions are frozen in buffer or culture media. Buffers include physiologically acceptable buffers such as phosphate buffer, histidine buffer, citrate buffer, acetate buffer, and other buffers known by those of skill in the art. In some cases exosome compositions disclosed herein are lyophilized.

Methods of isolation or purification of exosome compositions such as paracrine signaling exosome compositions disclosed herein include combining compositions comprising exosomes, for example in vitro exosomes, and SDC2+ mesenchymal stem cells (e.g., SDC2+ mesenchymal stromal stem cells). In some instances, methods of isolation or purification of exosome compositions include combining compositions comprising in vitro exosomes and regulatory T cells. Regulatory T cells include CD25+ regulatory T cells, CD4+ regulatory T cells, FoxP3+ regulatory T cells, CD25+ CD4+FoxP3+ regulatory T cells, and combinations thereof. In some instances, methods of isolation or purification of exosome compositions include combining compositions comprising in vitro exosomes, SDC2+ mesenchymal stem cells (e.g., SDC2+ mesenchymal stromal stem cells), and regulatory T cells.

Disclosed herein are methods of isolation or purification of compositions comprising exosomes such as paracrine signaling exosomes in a therapeutically effective amount, which would be known by one of skill in the art. A therapeutically effective amount of exosomes, in some cases, ranges from $10^6$-$10^8$ exosomes, for example $10^6$, $10^7$, $10^8$, or more exosomes in the composition. In some cases, a therapeutically effective amount of exosomes ranges from 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Isolation or purification of exosome compositions, in some cases, comprises concentrating the exosome composition to be diluted by the individual prior to administration. In some cases, isolation or purification of exosome compositions comprises diluting the exosome composition making it ready to be administered by the individual. In some cases, methods of isolation or purification of exosome compositions results in single use vials or syringes. In some cases, methods of isolation or purification of exosome compositions results in multiple doses are present in a single container.

Isolation or purification of exosome compositions such as paracrine signaling exosome compositions, in some cases, is accomplished with the use of antibodies to SDC2, which has the effect of increasing the yield of exosomes and increasing the proportion of isolated exosomes that comprise SDC2. Methods of isolation or purification comprise incubating a composition comprising exosomes with an anti-SDC2 antibody and retaining only the exosomes bound to the anti-SDC2 antibody. Anti-SDC2 antibodies are known by those of skill in the art as having the property of binding specifically to SDC2. Incubation of a composition comprising exosomes with the anti-SDC2 antibody is done in a buffer that promotes specific binding of the anti-SDC2 antibody to SDC2 and at a temperature that is optimal for antibody binding and exosome stability. In some cases, the incubation is done at room temperature. In some cases, the incubation is done at 4° C. The incubation buffer comprises at least one or a buffer, a detergent, and a salt.

The composition comprising exosomes such as paracrine signaling exosomes from which the exosome composition is isolated or purified using antibodies to SDC2, in some cases, comprises a cell culture. A cell culture includes but is not limited to SDC2+ cells, mesenchymal stem cells, SDC2+ mesenchymal stem cells, SDC2+ mesenchymal stromal stem cells, and combinations thereof. In some cases, the cell culture is genetically modified to overexpress SDC2 by methods known by one of skill in the art. Methods of isolation or purification of exosome compositions using anti-SDC2 antibodies comprise a method of isolating the SDC2 antibody-exosome complex from the starting material. SDC2 antibody-exosome complexes are purified by methods known in the art including but not limited to fluorescence activated cell sorting (FACS), immunoprecipitation, column purification using protein A beads, column purification using protein G beads, column purification using biotinylated beads and a biotinylated secondary antibody, and magnetic bead based separation methods. Exosome compositions are then eluted from the antibody using a buffered salt solution having stringency sufficient to elute the exosome composition from the antibody. Buffered salt solutions are removed from the exosome composition using a desalting column or dilation procedure. The resulting isolated, purified exosome composition is then diluted in a physiologically acceptable buffer or excipient and frozen or otherwise stored at a temperature where the exosome composition with retain potency and stability.

Isolation or purification of exosome compositions such as paracrine signaling exosome compositions, in some cases, is accomplished using ultracentrifugation methods, such as preparative ultracentrifugation. Methods of isolation or purification of exosome compositions, comprise obtaining a population of cells such as stromal cells, SDC2+ cells, mesenchymal stem cells, SDC2+ mesenchymal stem cells, SDC2+ mesenchymal stromal stem cells, and combinations thereof. In some cases, the cells have been genetically altered to overexpress SDC2. The media or supernatant of the cell culture is isolated or purified from the cell culture. Then, the media or supernatant is mixed with an appropriate salt or buffer to enhance the separation efficacy in ultracentrifugation. The resulting mixture is added to an ultracentrifugation tube which allows the mixture to safely endure high centrifugal forces of about 100,000×g (or 100,000 times the force of gravity) for 1 to 24 hours. Exosome compositions are found concentrated together and removed from the tube. In some cases, the exosomes are removed as a resuspended pellet from the tube. In some cases, the exosomes are visualized in the resulting density gradient and removed by needle aspiration, or other method. The resulting exosome composition is purified from the ultracentrifugation buffer and diluted in a physiologically acceptable buffer or excipient and frozen or otherwise stored at a temperature where the exosome composition with retain potency and stability.

Isolation or purification of exosome compositions such as paracrine signaling exosome compositions, is accomplished in some cases using ultrafiltration. Some ultrafiltration methods are known in the art, such as methods involving concentration columns that allow passage of aqueous buffers but not high molecular weight substances, such as exosomes. Some examples of ultrafiltration methods of isolation or purification method comprise obtaining a population of cells such as stromal cells, SDC2+ cells, mesenchymal stem cells, SDC2+ mesenchymal stem cells, SDC2+ mesenchymal stromal stem cells, or combinations thereof. In some cases, the cells have been genetically altered to overexpress SDC2 or have been provided with exogenous SDC2 or a vector encoding SDC2. The media or supernatant of the cell culture is isolated or purified from the cell culture. Then the media or supernatant is concentrated, such as by a factor of 30, for example 150 ml of starting media or supernatant resulting in 10 ml of concentrated exosomes, using a Stirred Cell Model 8200 with 100,000 kDa Biomax polyethersulfone or Ultracel regenerated cellulose membranes using nitrogen gas at 10 psi. The concentrated exosomes are then transferred to a collection device such as an Amicon Ultra-15 100,000 kDa device and centrifuged, for example in an Allegra X-15R centrifuge at 4,000×g at 4° C., to concentrate the exosomes by another factor of 20, for example 10 ml of concentrated exosomes resulting in a further concentrated 0.5 ml. Alternative columns and centrifuges are known to be substituted by one of skill in the art.

In some cases, isolation or purification of exosomes compositions such as paracrine signaling exosome compositions is accomplished using automated systems of manufacturing. In some cases, automated manufacturing is comprises using the Terumo Quantum Cell Expansion System.

Methods of Delivery

Exosome compositions such as paracrine signaling exosome compositions, as described herein, are used in methods of delivery of immuno-modulatory signals to the intracellular space of a mammal. Exosome compositions such as paracrine signaling exosome compositions, as described herein, are also for use in delivery of immuno-modulatory signals to the intracellular space of a mammal. Immuno-modulatory signals comprise compositions that modulate the inflammatory or immune response in a mammal. In some cases, the exosome composition is isolated or purified from a stromal cell, a SDC2+ cell, mesenchymal stem cell, or a SDC2+ mesenchymal stem cell. The exosome composition contains the immuno-modulatory signal thereby delivering the immuno-modulatory signal to the intracellular space of the mammal when administered to the mammal without exposing the contents of the exosome composition to the humoral immune system of the mammal.

Once administered, delivery of the exosome composition such as paracrine signaling exosome composition to the intracellular space of the mammal occurs though processes including but not limited to phagocytosis, endocytosis, or fusion. The exosome composition is administered to the mammal in need of immuno-modulatory signaling by routes of administration known in the art, appropriate to the need of the mammal. Routes of administration include but are not limited to parenteral (including subcutaneous, intravenous, intra-arterial, intraosseous, intracerebral, intracerebroventricular, intrathecal, intramedullary, intraarticular, intramuscular, or intraperitoneal injection), rectal, respiratory or inhalation, topical, transdermal, or oral (for example, in capsules, suspensions, or tablets).

Methods and uses of delivery use exosome compositions such as paracrine signaling exosome compositions disclosed herein that are formulated in a physiologically acceptable buffer and at least one excipient. Non-limiting examples of excipients include sucrose, trehalose, polyethylene glycol, a polysaccharide, a carrier protein, an inert protein, dextran, hydroxyl ethyl starch (HETA), PEG-4000, gelatin, PLGA, Eudragit RS 100 Nanoparticles, and combinations thereof. Such exosome compositions are stored at a temperature determined to be most stable (i.e., wherein the exosome composition retains highest potency). In some cases, addition of one or more excipients allows the composition to retain potency when stored at a higher temperature than otherwise would be possible.

Methods and uses of delivery of exosome compositions such as paracrine signaling exosome compositions disclosed herein include compositions that comprise exosomes, for example in vitro exosomes, and SDC2+ mesenchymal stem cells (e.g., SDC2+ mesenchymal stromal stem cells). In some instances, exosome compositions include compositions comprising in vitro exosomes and regulatory T cells. Regulatory T cells include CD25+ regulatory T cells, CD4+ regulatory T cells, FoxP3+ regulatory T cells, CD25+CD4+ FoxP3+ regulatory T cells, and combinations thereof. In some instances, exosome compositions include compositions comprising in vitro exosomes, SDC2+ mesenchymal stem cells (e.g., SDC2+ mesenchymal stromal stem cells), and regulatory T cells.

Methods and uses of delivery comprise administration of exosome compositions such as paracrine signaling exosome compositions in a therapeutically effective amount, which would be known by one of skill in the art. A therapeutically effective amount of exosomes, in some cases, ranges from $10^6$-$10^8$ exosomes, for example $10^6$, $10^7$, $10^8$, or more exosomes in the composition. In some cases, a therapeutically effective amount of exosomes ranges from 1 µg to 700 mg of exosomes, for example 1 µg, 10 µg, 20 µg, 50 µg, 100 µg, 150 µg, 200 µg, 250 µg, 500 µg, 750 µg, 1 mg, 2 mg, 3 mg, 4 mg, 5 mg, 6 mg, 7 mg, 10 mg, 20 mg, 50 mg, 100 mg, 200 mg, 300 mg, 400 mg, 500 mg, 600 mg, 700 mg, or more exosomes in the composition. Exosome compositions, in some cases, are concentrated to be diluted by the individual prior to administration. In some cases, exosome compositions are diluted and ready to be administered by the individual. In some cases, exosome compositions are contained in single use vials or syringes. In some cases, multiple doses are present in a single container.

Methods and uses of delivery use exosome compositions such as paracrine signaling exosome compositions that comprise proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin.

Methods and uses of delivery to an intracellular space include exosome compositions such as paracrine signaling exosome compositions topically (e.g., applied directly to the skin of the individual being treated). In some cases, topical administration is used to treat diseases of the skin. Topical administration includes epicutaneous administration. Exosome compositions for topical administration are formulated specifically to be administered to the skin. Such topical exosome compositions include but are not limited to solutions, lotions, creams, ointments, gels (including hydrogels or collagen gels), foams, transdermal patches, powders, pastes, and tinctures. In some cases, exosome compositions comprise a hydrogel or a collagen gel.

Methods and uses of delivery to an intracellular space include administration of exosome compositions such as paracrine signaling exosome compositions to the eye (e.g., intraocular or ophthalmic). Exosome compositions for administration to the eye comprise formulations (e.g., buffers or excipients) known by one of skill in the art to be appropriate to the eye.

Methods and uses of delivery to an intracellular space include administration by injection. Injection of exosome compositions such as paracrine signaling exosome compositions to a subject is effective in treating certain indications, diseases, or disorders. Delivery of an exosome composition via injection includes but is not limited to injection to the lymph nodes, subcutaneous injection, intramuscular injection, intravenous injection, intraperitoneal injection, intrathecal injection, intradermal injection, intraarticular injection, and other injection methods known by one of skill in the art. Exosome compositions for injection comprise formulations or physiologically acceptable buffers or excipients for injection.

Methods and uses of delivery to an intracellular space include administration of exosome compositions such as paracrine signaling exosome compositions disclosed herein via a respiratory or inhalation route using an inhalation device. An inhalation device is capable of administering therapeutic compositions to the respiratory airways of a patient. Inhalation devices include conventional inhalation devices such as metered dose inhalers, dry powder inhalers, jet nebulizers, ultrasonic wave nebulizers, heat vaporizers, soft mist inhalers, and high efficiency nebulizers. Nebulizers, metered dose inhalers, and soft mist inhalers deliver therapeutics by forming an aerosol which includes droplet sizes that can easily be inhaled. The aerosol can be used by a patient within the bounds of an inhalation therapy. A nebulizer is able to turn a therapeutic or medication into a fine aerosol mist that is delivered to the lungs of an individual.

Methods and uses of delivery to an intracellular space include use of exosome compositions such as paracrine signaling exosome compositions comprising an immunosuppressive drug. Non-limiting examples of immunosuppressive drugs include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Exosome compositions comprise anti-TNF antibodies, including but not limited to infliximab, adalimumab, certolizumab, and golimumab. Exosome compositions comprise TNF inhibitors including but not limited to etanercept, xanthine derivatives, and bupropion. In some cases, exosome compositions comprise one or more NSAIDs. In some cases, exosome compositions comprise one or more steroids.

Supplemented Stem Cell and Stromal Stem Cell Compositions

Disclosed herein are exosome compositions such as paracrine signaling exosome compositions comprising supplemented stem cell and stromal stem cell compositions. Supplemented stem cell and stromal stem cell compositions comprise cultured stem cells or stromal stem cells and at least one exosome composition disclosed herein. In some cases, the exosome composition is isolated from the cultured stem cells or stromal stem cells and then combined with the cultured stem cells to enhance the therapeutic efficacy of the cultured stem cells.

Supplemented stem cell and stromal stem cell compositions comprise exosome compositions such as paracrine signaling exosome compositions, such as SDC2+ exosomes. In some compositions, at least 20% of the exosomes in the composition are SDC2+ or comprise SDC2. In some cases at least 20%, 30%, 40%, 50%, 60%, 70%, 80%, 90%, 95%, 99%, or more of the exosomes comprise SDC2. SDC2, also known as syndecan-2, CD362, S2, and fibroglycan, or otherwise referred to herein, in some instances is found on the surface of the exosome or at least comprising a polypeptide portion that is found on the surface of the exosome. In some instances, SDC2 is found at the interior of the exosome. The proportion of exosomes in the composition comprising SDC2 is determined by immunofluorescence, for example FACS, microscopy, or other method known by one of skill in the art.

Supplemented stem cell compositions comprise cultured stem cells or stromal stem cells that in some cases are SDC2+. At least 20% of the cultured stem cells or stromal stem cells are SDC2+ in some cases. The cultured stem cell or stromal stem cell composition comprises, in some cases, 20% to 90% SDC2+ cells, for example 20%, 30%, 40%, 50%, 60%, 70%, 80%, 90% SDC+ cells or more than 90% SDC2 cells, up to and including a uniform population of 100% SDC2 positive cells.

Supplemented stem cell and stromal stem cell compositions in some cases, comprise exosome compositions such as paracrine signaling exosome compositions comprising proteins with or without therapeutic efficacy. Proteins include but are not limited to IL-12, suppressor of cytokine signaling (SOCS), p53, PTEN, CD52, TSC1, FOXP3, Soluble Immune Response Suppressor (SIRS), TGFB, CD39, CD39L3, CD73, and Maspin.

Supplemented stem cell and stromal stem cell compositions comprise, in some cases, an exosome composition such as paracrine signaling exosome composition comprising an immunosuppressive drug. Non-limiting examples of immunosuppressive drugs include but are not limited to a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. Exosome compositions comprise anti-TNF antibodies, including but not limited to infliximab, adalimumab, certolizumab, and golimumab. Exosome compositions comprise TNF inhibitors including but not limited to etanercept, xanthine derivatives, and bupropion. In some cases, exosome compositions comprise one or more NSAIDs. In some cases, exosome compositions comprise at least one steroid.

Exosome compositions, methods of isolation, and methods and uses in treating disease are illustrated by the drawings provided herein. FIG. 1 provides a cartoon depiction of an exosome as contemplated herein. In this drawing, a number of components important to some exosomes are shown including adhesion molecules such as ICAMs and integrins; tetraspanins such as CD63, CD9, and CD81; cytoskeleton proteins such as actin, tubulin ERMs, and myosin; membrane trafficking proteins such as RABs and annexins; endosomal molecules such as TSG101, ubiquitin, clatherin, and ALIX; and lipid rafts including ceramide, cholesterol, and phosphatidylserine; nucleic acids such as mRNA molecules, for example mRNA molecules encoding a protein or proteins of interest, DNA fragments or entire DNA coding molecules of various lengths up to and including DNA molecules harboring multiple coding loci, miRNA or pre-miRNA, such as miRNA or pre-miRNA impacting the expression of a gene or transcript encoding a protein involved in an immune response. None, any or all of these components, up to and including various permutations or combinations up to all of these components or variants of one or more of these components, are present in some various SDC2+ exosomes as contemplated herein.

Figure 2:
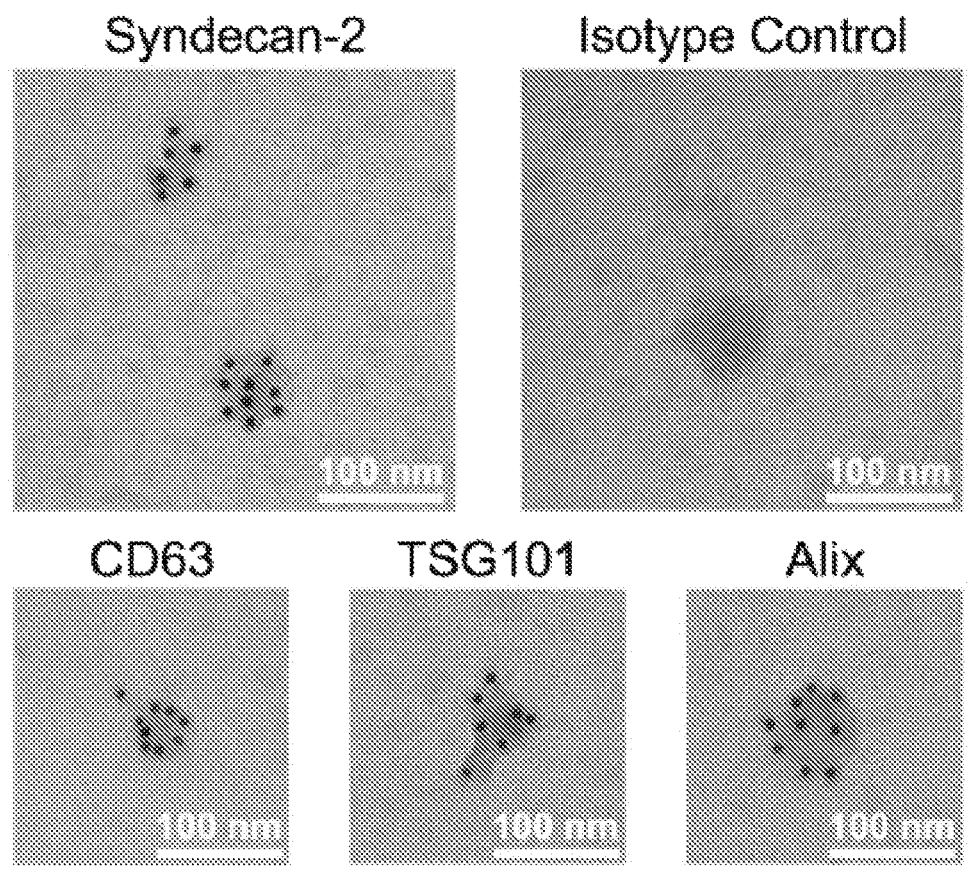
FIG. 2 shows SDC2 expression by exosomes derived from SDC2+ mesenchymal stromal cells (MSC) by transmission electron microscopy.

FIG. 2 shows SDC2 presence in exosomes derived from SDC2+ mesenchymal stromal cells (MSC) by transmission electron microscopy to detect gold-tagged anti-SDC2 antibody binding. Expression of CD63, TSG101 and Alix is similarly shown by transmission electron microscopy of metal-labeled antibodies to the respective proteins. The scale bar in each photomicrograph is 100 nm. The figure demonstrates that SDC2, CD63, TSG101 and Alix are present in the exosomes isolated from SDC2+ mesenchymal stem cells. The isotype control demonstrates that the antibodies bind specifically. The lack of Exosome labeling with a rat IgG2B APC-conjugated Isotype Control antibody (Cat #IC013A from R&D Systems) indicates the specificity of the anti-SDC2 labeling with an equivalent rat IgG2B APC-conjugated anti-SDC2 antibody.

Figure 3:
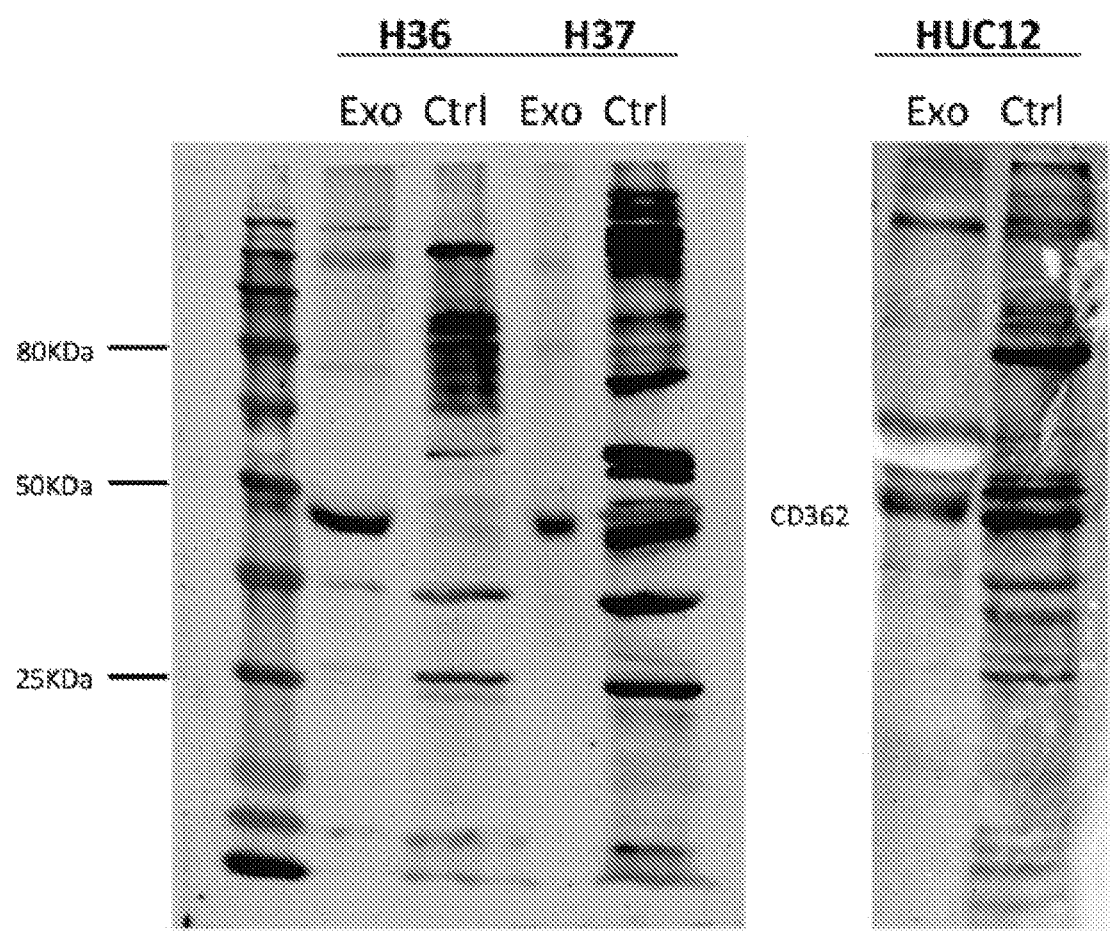
FIG. 3 shows SDC2 expression by exosomes derived from SDC2+ mesenchymal stromal cells (MSC) by Western blot.

FIG. 3 shows SDC2 expression in exosomes derived from SDC2+ mesenchymal stromal cells (MSC) by protein gel electrophoresis. In this experiment, H36 (marrow derived SDC2+ MSC), H37 (marrow derived SDC2+ MSC), and HUC12 (human umbilical cord derived SDC2+ MSC) cells and exosomes purified from those cells were homogenized in lysis buffer and run on an SDS-PAGE gel, along with unpurified whole sample protein extracts. Proteins from the gel were transferred to a membrane and stained with a rat IgG2B anti-human SDC2 antibody. In each 'exo' exosome protein extract lane, strong enrichment at below 50 kDa is observed, indicative of SDC2/CD362 being disproportionately present in the exosome fraction relative to the whole cell extract fraction.

SDC2+ exosomes were tested for their safety and efficacy to reduce inflammation-related damage in a mammalian model of inflammation damage.

Figure 4:
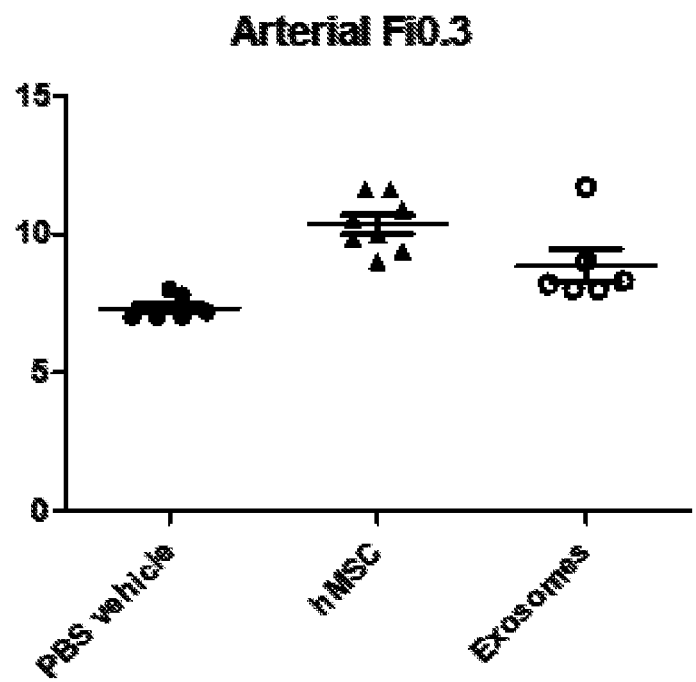
FIG. 4 shows arterial FI 0.3 in rats treated with PBS vehicle, human mesenchymal stem cells, or exosomes in a rat model of ARDS.

FIG. 4 shows arterial FI 0.3 in rats treated with phosphate buffered saline ('PBS') vehicle, human umbilical cord derived SDC2+ stromal cells, or exosomes in a rat model of acute respiratory distress syndrome ('ARDS'). In this experiment, 300 g Sprague Dawley rats were given an intrapulmonary dose of E. coli to induce ARDS lung injury. One hour later, the rats were treated with a 90-100 µg dose of exosomes or 4 million human mesenchymal stem cells (hMSC). The extent of lung injury was then measured 24 hours later by measurement of arterial oxygen at FI 0.3. This experiment shows that rats treated with only 90-100 µg of exosomes had improved lung function relative to those treated with PBS vehicle. It is expected that rats treated with a greater dose show increased improvement in lung function, such as at a level comparable to that of hMSC treatment.

Figure 5:
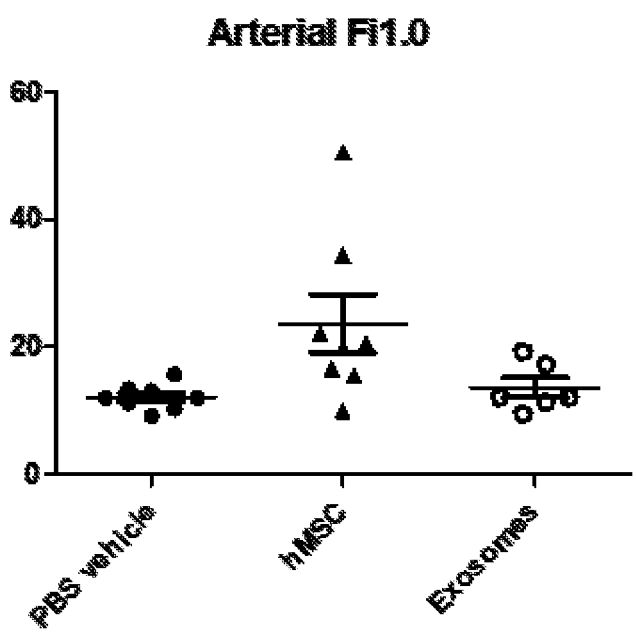
FIG. 5 shows arterial FI 1.0 in rats treated with PBS vehicle, human mesenchymal stem cells, or exosomes in a rat model of ARDS.

FIG. 5 shows arterial FI 1.0 in rats treated with PBS vehicle, human umbilical cord derived SDC2+ stromal cells, or exosomes in a rat model of ARDS. In this experiment, 300 g Sprague Dawley rats were given an intrapulmonary dose of E. coli to induce ARDS lung injury. One hour later, the rats were treated with a 90-100 µg dose of exosomes or 4 million human umbilical cord derived SDC2+ stromal cells. The extent of lung injury was then measured 24 hours later by measurement of arterial oxygen at FI 1.0. This experiment shows that rats treated with only 90-100 µg of exosomes had no decrease in lung function than those treated with PBS vehicle. This result indicates that exosome administration is not deleterious to animal lung recovery.

Figure 6:
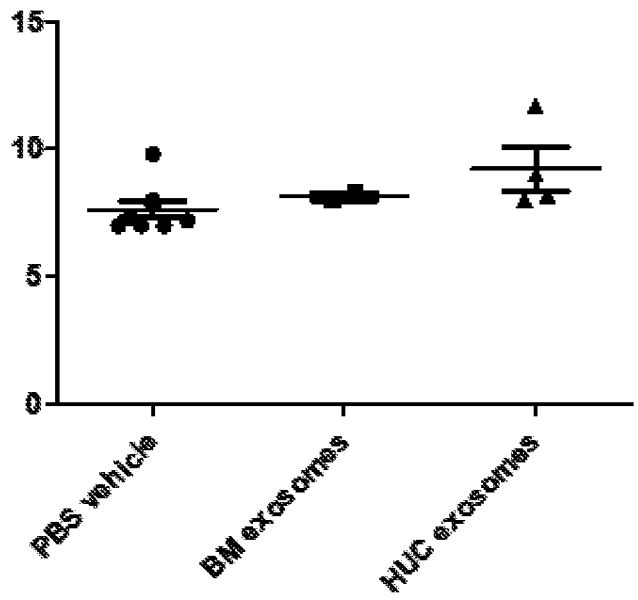
FIG. 6 shows arterial FI 0.3 in rats treated with PBS vehicle, bone marrow (BM) exosomes, or human umbilical cord (HUC) exosomes in a rat model of ARDS.

FIG. 6 shows arterial FI 0.3 in rats treated with PBS vehicle, bone marrow (BM) exosomes, or human umbilical cord (HUC) exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes purified from bone marrow mesenchymal stem cells or human umbilical cord mesenchymal stem cells. The extent of lung injury was then measured 24 hours later by measurement of arterial oxygen at FI 0.3. This experiment shows that rats treated with only 90-100 µg of exosomes had no decrease in lung function than those treated with PBS vehicle. It is expected that rats treated with a greater dose greater dose show increased improvement in lung function.

Figure 7:
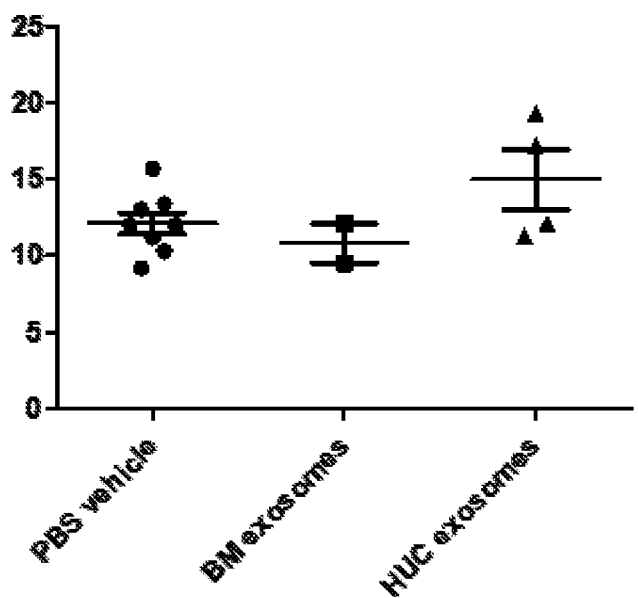
FIG. 7 shows arterial FI 1.0 in rats treated with PBS vehicle, bone marrow (BM) exosomes, or human umbilical cord (HUC) exosomes in a rat model of ARDS.

FIG. 7 shows arterial FI 1.0 in rats treated with PBS vehicle, bone marrow (BM) exosomes, or human umbilical cord (HUC) exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes purified from bone marrow mesenchymal stem cells or human umbilical cord mesenchymal stem cells. The extent of lung injury was then measured 24 hours later by measurement of arterial oxygen at FI 1.0. This experiment shows that rats treated with only 90-100 µg of exosomes had no decrease in lung function than those treated with PBS vehicle. It is expected that rats treated with a greater dose show increased improvement in lung function.

Figure 8:
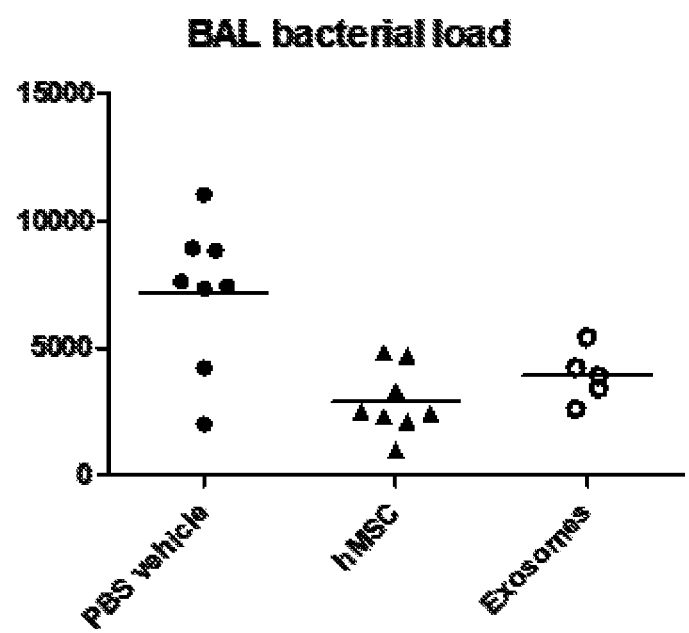
FIG. 8 shows bronchioaveolar lavage (BAL) bacterial load in rats treated with PBS vehicle, human mesenchymal stem cells, or exosomes in a rat model of ARDS.

FIG. 8 shows bronchioaveolar lavage (BAL) bacterial load in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL bacterial load. This experiment shows that rats treated with only 90-100 µg of exosomes had reduced BAL bacterial load than those treated with PBS vehicle, demonstrating the efficacy of administering exosomes as a treatment. It is expected that rats treated with a greater dose show increased improvement in lung function.

Figure 9:
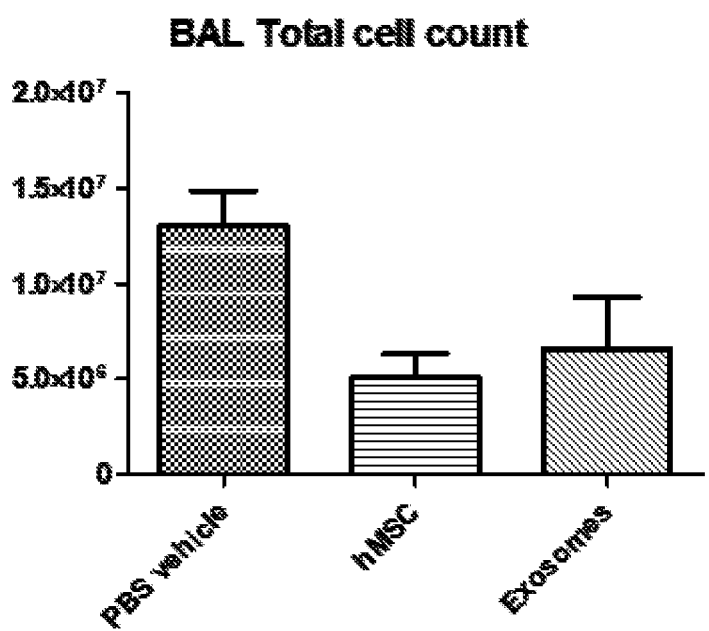
FIG. 9 shows bronchioaveolar lavage (BAL) total cell count in rats treated with PBS vehicle, human mesenchymal stem cells, or exosomes in a rat model of ARDS.

FIG. 9 shows bronchioaveolar lavage (BAL) total cell count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL total cell count. This experiment shows that rats treated with only 90-100 µg of exosomes had reduced BAL total cell count compared to those treated with PBS vehicle, demonstrating the efficacy of administering exosomes as a treatment. It is expected that rats treated with a greater dose show even better improvement in lung function.

Figure 10:
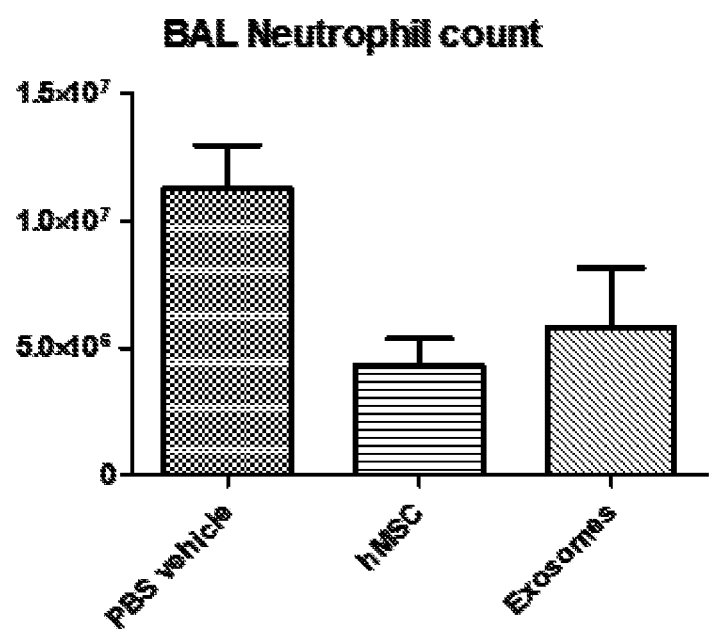
FIG. 10 shows bronchioaveolar lavage (BAL) neutrophil count in rats treated with PBS vehicle, human mesenchymal stem cells, or exosomes in a rat model of ARDS.

FIG. 10 shows bronchioaveolar lavage (BAL) neutrophil count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of BAL neutrophil count. This experiment shows that rats treated with only 90-100 µg of exosomes had fewer infiltrating neutrophils in the lung than those treated with PBS vehicle, demonstrating the efficacy of administering exosomes as a treatment. It is expected that rats treated with a greater dose show even better improvement in lung function.

Figure 11:
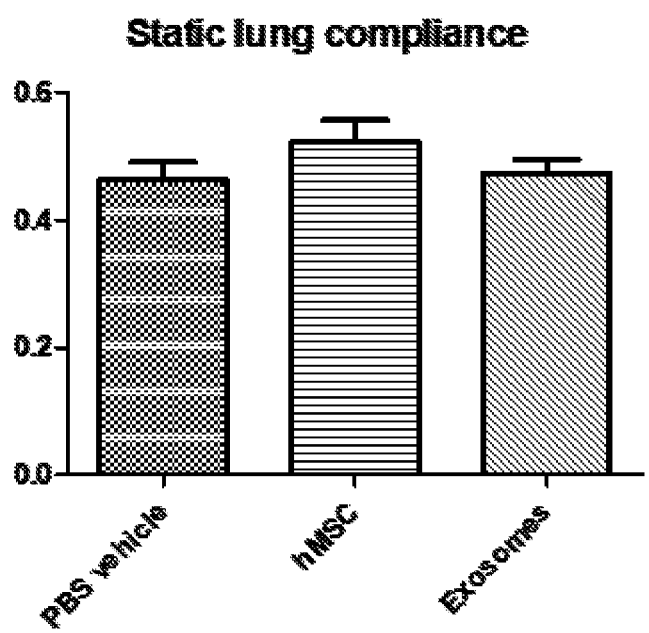
FIG. 11 shows static lung compliance in rats treated with PBS vehicle, human mesenchymal stem cells, or exosomes in a rat model of ARDS.

FIG. 11 shows static lung compliance in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of static lung compliance. This experiment shows that rats treated with only 90-100 µg of exosomes had no decrease in lung function than those treated with PBS vehicle. This result indicates that exosome administration is not deleterious to animal lung recovery.

Figure 12:
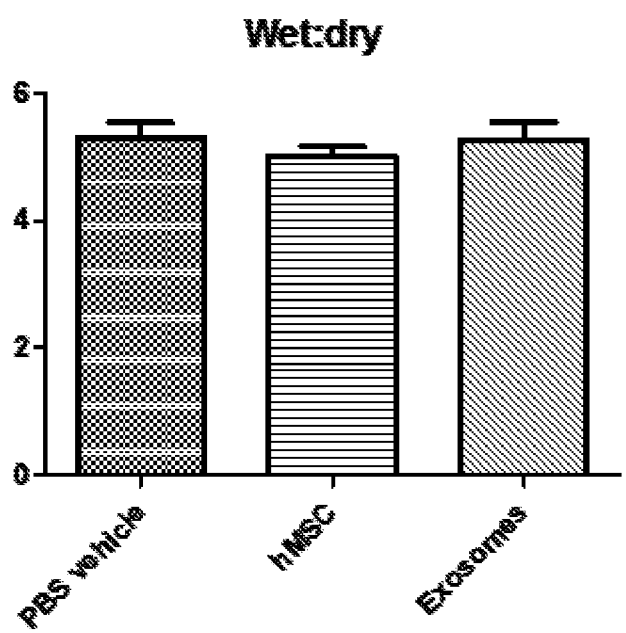
FIG. 12 shows lung wet dry ratio in rats treated with PBS vehicle, human mesenchymal stem cells, or exosomes in a rat model of ARDS.

FIG. 12 shows lung wet dry ratio in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 90-100 µg dose of exosomes or 4 million human mesenchymal stem cells (hMSC). The extent of lung injury was then measured 24 hours later by measurement of lung wet dry ratio. This experiment shows that rats treated with only 90-100 µg of exosomes had no decrease in lung function than those treated with PBS vehicle. This result indicates that exosome administration is not deleterious to animal lung recovery.

Figure 13:
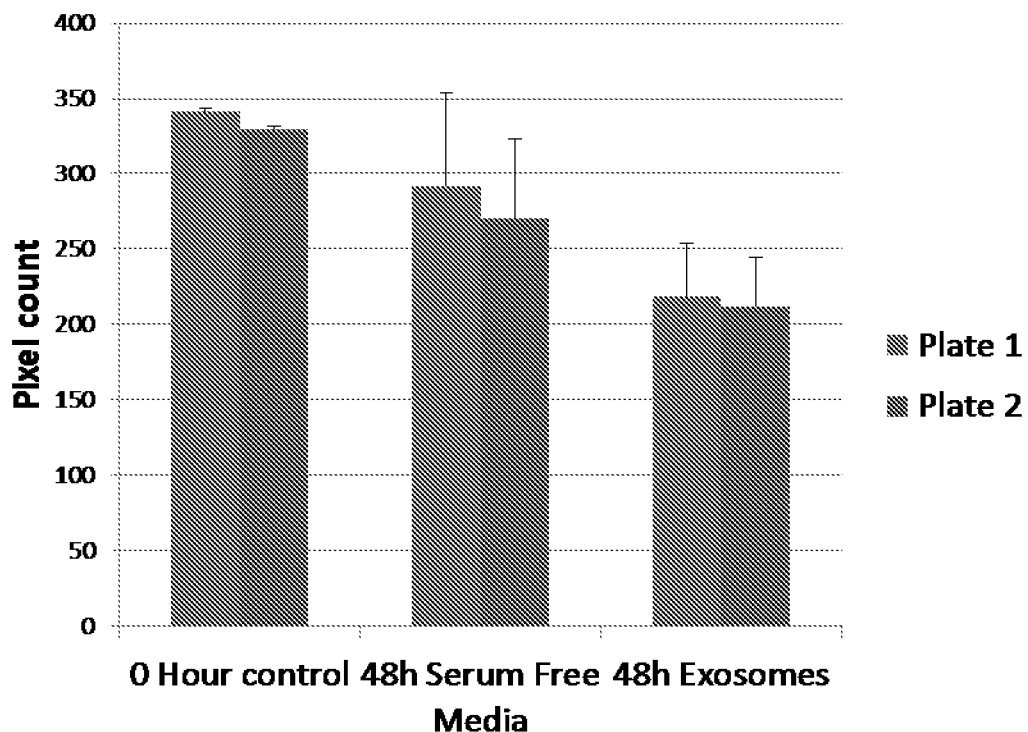
FIG. 13 shows results from a scratch assay with A549 cells treated with serum free media or exosomes for 48 hours.

FIG. 13 shows results from a scratch assay with A549 cells treated with serum free media or exosomes for 48 hours. The scratch assay measures cell migration into a scratch created in adherent cells growing in a culture dish. In this assay, 300,000 A549 cells were grown in a monolayer in a 24 well plate. The cells were scraped with a p200 pipet tip in a straight line to create a scratch. An image was taken at the time of scraping (0 h) and after a 48 hour incubation with serum free media or 2 µg exosomes in serum free media. Exosomes are shown there to reduce the size of the scratch, therefore increasing cell migration of A549 cells compared to the serum free media control. These results indicate that exosomes increase epithelial cell migration.

Figure 14:
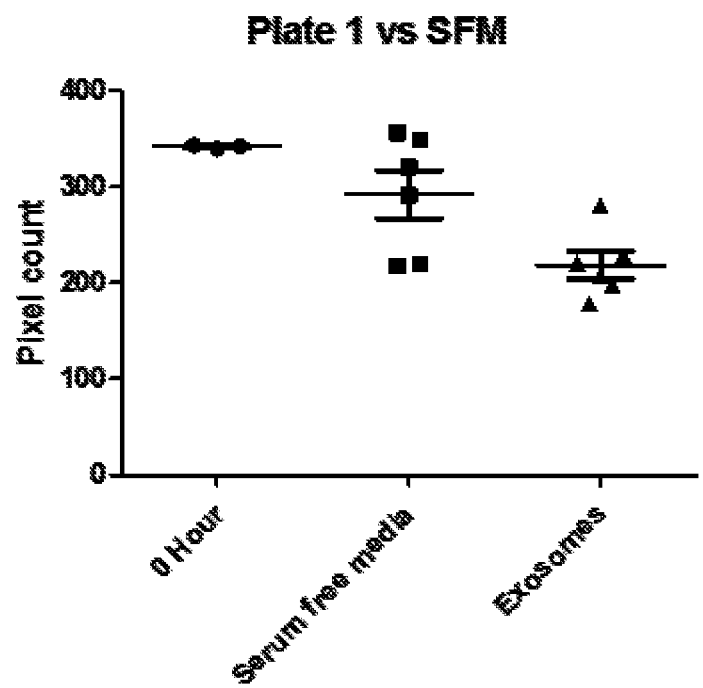
FIG. 14 shows results a scratch assay with A549 cells, plate 1.

FIG. 14 shows results a scratch assay with A549 cells, plate 1. An image was taken at the time of scraping (0 h) and after a 48 hour incubation with serum free media or 2 µg exosomes in serum free media. Exosomes are shown there to reduce the size of the scratch, therefore increasing cell migration of A549 cells compared to the serum free media control. These results indicate that exosomes increase epithelial cell migration.

Figure 15:
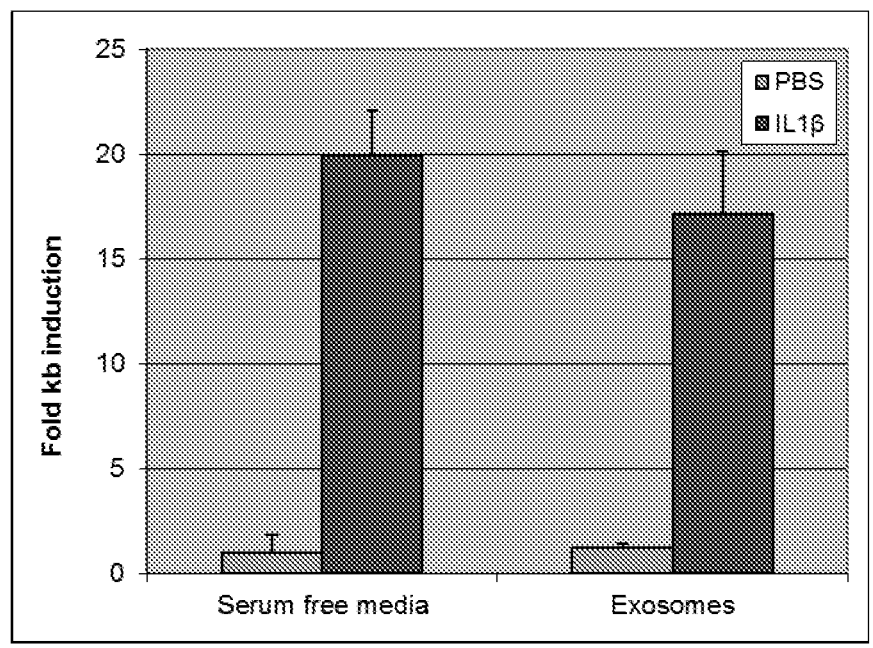
FIG. 15 shows a bar graph of NFκB reporter gene activation with IL1β stimulation in cells treated with serum free media or exosomes purified by ultrafiltration.

FIG. 15 shows a bar graph of NFκB reporter gene activation with IL1β stimulation in cells treated with serum free media or exosomes purified by ultrafiltration. In this assay, 30,000 A549 cells that were transfected with an NFκB-luciferase reporter gene were grown in a 96 well dish. The cells were treated with serum free media or 2 µg exosomes in serum free media for hours and then stimulated with human IL-1β for hours and luciferase activity was measured. A reduction was observed in luciferase activity in A549 cells treated with exosomes. Therefore, SDC2+ exosomes reduce NFκB activation.

Figure 16:
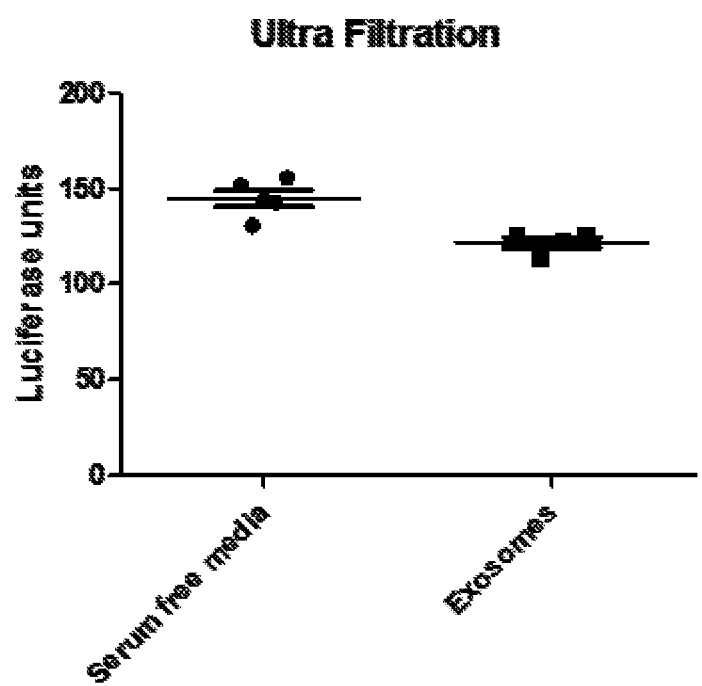
FIG. 16 shows a scatter graph of NFκB reporter gene activation with IL1β stimulation in cells treated with serum free media or exosomes purified by ultrafiltration.

FIG. 16 shows a scatter graph of NFκB reporter gene activation with IL1β stimulation in cells treated with serum free media or exosomes purified by ultrafiltration. In this assay, 30,000 A549 cells that were transfected with an NFκB-luciferase reporter gene were grown in a 96 well dish. The cells were treated with serum free media or 2 µg exosomes in serum free media and then stimulated with human IL-1β for hours and luciferase activity was measured. A reduction was observed in luciferase activity in A549 cells treated with exosomes. These results indicate that the exosome administration reduces NFκB activation.

Figure 17:
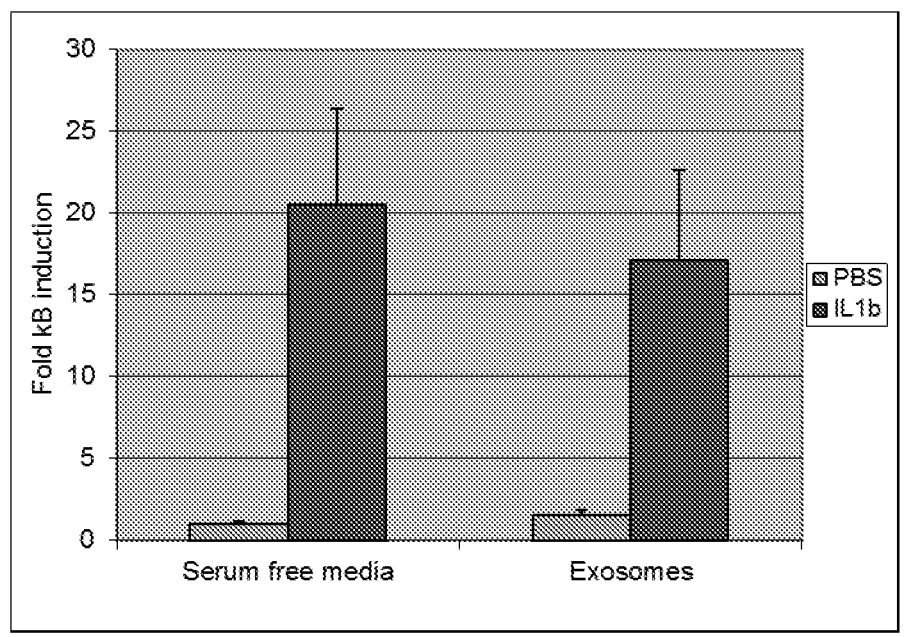
FIG. 17 shows a bar graph of NFκB reporter gene activation with IL1β stimulation in cells treated with serum free media or exosomes purified by ultracentrifugation.

FIG. 17 shows a bar graph of NFκB reporter gene activation with IL1β stimulation in cells treated with serum free media or exosomes purified by ultracentrifugation. In this assay, 30,000 A549 cells that were transfected with an NFκB-luciferase reporter gene were grown in a 96 well dish. The cells were treated with serum free media or 2 µg exosomes in serum free media for hours and then stimulated with human IL-1β for hours and luciferase activity was measured. A reduction was observed in luciferase activity in A549 cells treated with exosomes. Therefore, exosomes reduce NFκB activation.

Figure 18:
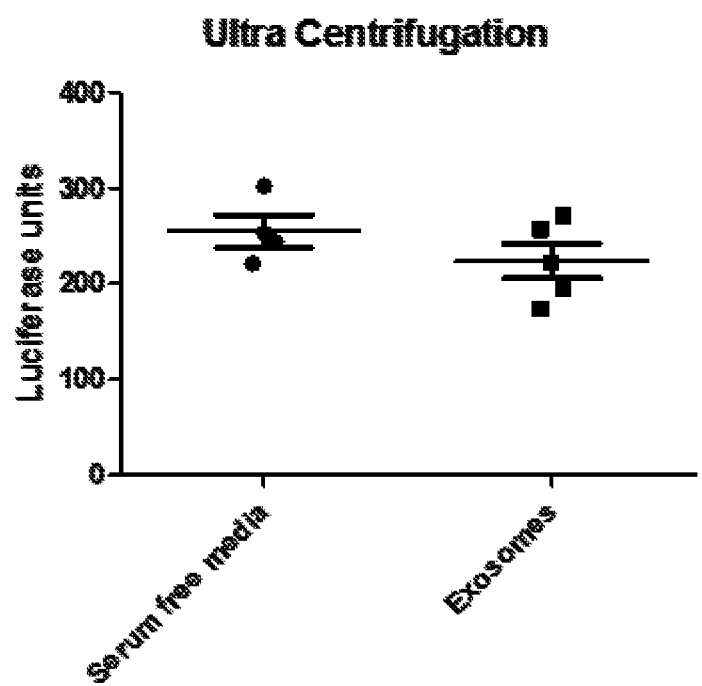
FIG. 18 shows a scatter graph of NFκB reporter gene activation with IL1β stimulation in cells treated with serum free media or exosomes purified by ultracentrifugation.

FIG. 18 shows a scatter graph of NFκB reporter gene activation with IL1β stimulation in cells treated with serum free media or exosomes purified by ultracentrifugation. In this assay, 30,000 A549 cells that were transfected with an NFκB-luciferase reporter gene were grown in a 96 well dish. The cells were treated with serum free media or 2 µg exosomes in serum free media for hours and then stimulated with human IL-1β for hours and luciferase activity was measured. A reduction was observed in luciferase activity in A549 cells treated with exosomes. These results indicate that the exosome administration reduces NFκB activation.

Figure 19:
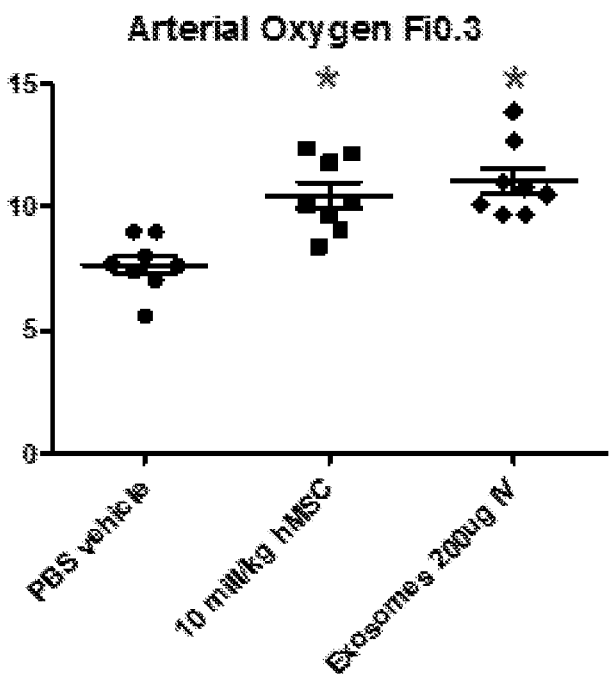
FIG. 19 shows arterial FI 0.3 in rats treated with PBS vehicle, human mesenchymal stem cells (10 mill/kg), or exosomes (200 µg, IV) in a rat model of ARDS.

FIG. 19 shows arterial FI 0.3 in rats treated with PBS vehicle, hMSC, or exosomes in a rat model of ARDS. In this experiment, 300 g Sprague Dawley rats were given an intrapulmonary dose of E. coli to induce ARDS lung injury, one hour later, the rats were treated with a 200 µg dose of exosomes or 10 million/kg human MSC by intravenous administration. The extent of lung injury was then measured 24 hours later by measurement of arterial oxygen at FI 0.3. This experiment shows that rats treated with 200 µg of exosomes or 10 million/kg human MSC had significantly improved lung function compared to those treated with PBS vehicle (one way anova p<0.0001). This result indicates that exosome administration is effective in treating animal lung injury and suggests that exosome treatment is comparable to hMSC treatment.

Figure 20:
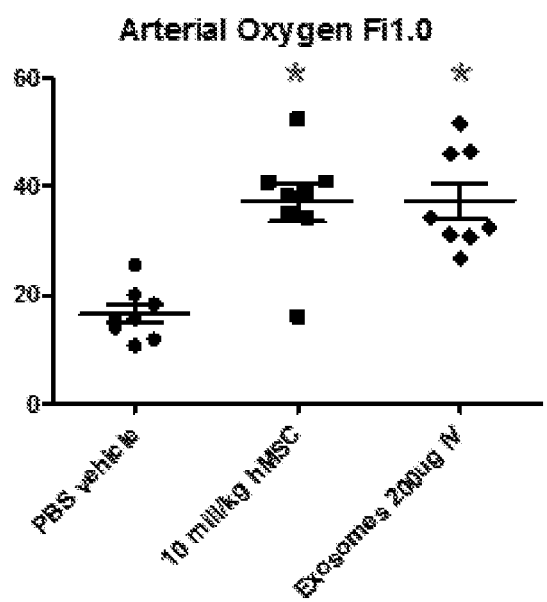
FIG. 20 shows arterial FI 1.0 in rats treated with PBS vehicle, human mesenchymal stem cells (10 mill/kg), or exosomes (200 µg, IV) in a rat model of ARDS.

FIG. 20 shows arterial FI 1.0 in rats treated with PBS vehicle, hMSC, or exosomes in a rat model of ARDS. In this experiment, 300 g Sprague Dawley rats were given an intrapulmonary dose of E. coli to induce ARDS lung injury, one hour later, the rats were treated with a 200 µg dose of exosomes or 10 million/kg human MSC by intravenous administration. The extent of lung injury was then measured 24 hours later by measurement of arterial oxygen at FI 0.3. This experiment shows that rats treated with 200 µg of exosomes or 10 million/kg human MSC had significantly improved lung function compared to those treated with PBS vehicle (one way anova p<0.0001). This result indicates that exosome administration is effective in treating animal lung injury and suggests that exosome treatment is comparable to hMSC treatment.

Figure 21:
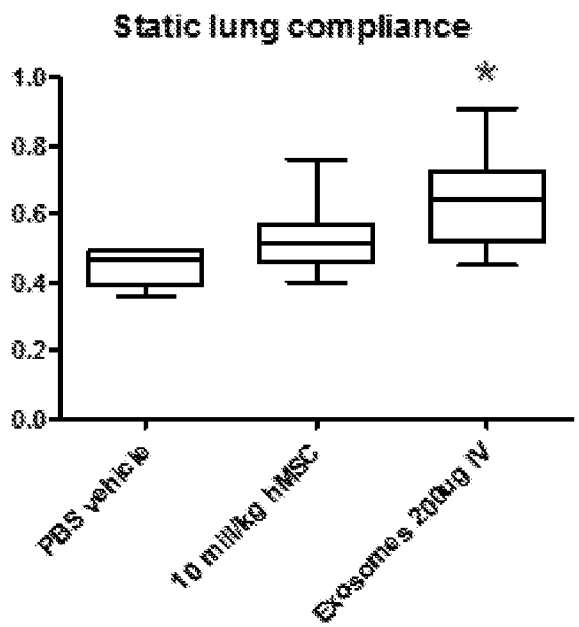
FIG. 21 shows static lung compliance in rats treated with PBS vehicle, human mesenchymal stem cells (10 mill/kg), or exosomes (200 µg, IV) in a rat model of ARDS.

FIG. 21 shows static lung compliance in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated with a 200 µg intravenous dose of exosomes or 10 million/kg human mesenchymal stem cells (hMSC). The extent of lung injury was then measured 24 hours later by measurement of static lung compliance. This experiment shows that rats treated with 200 µg of exosomes or 10 million/kg human MSC had significantly improved lung function compared to those treated with PBS vehicle (one way anova p<0.01). This result indicates that exosome administration is effective in treating animal lung injury and suggests that exosome treatment is comparable to hMSC treatment.

Figure 22:
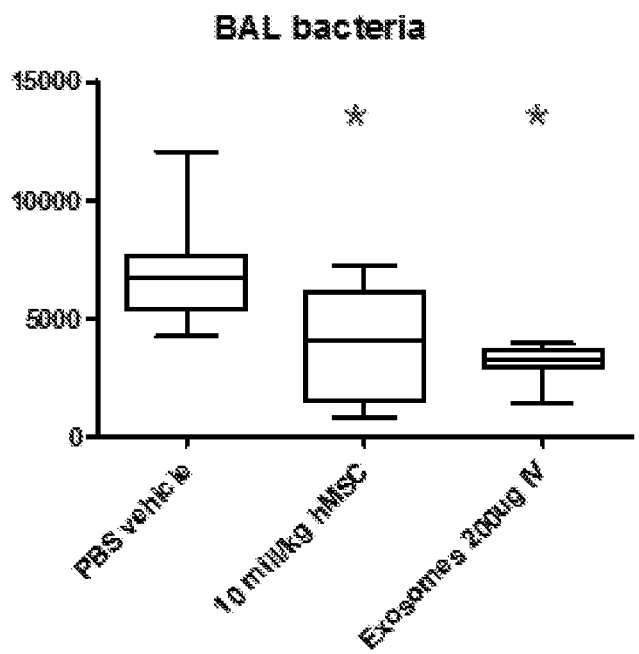
FIG. 22 shows bronchioaveolar lavage (BAL) bacterial load in rats treated with PBS vehicle, human mesenchymal stem cells (10 mill/kg), or exosomes (200 µg, IV) in a rat model of ARDS.

FIG. 22 shows bronchioaveolar lavage (BAL) bacterial load in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200 µg dose of exosomes or 10 million/kg human mesenchymal stem cells (hMSC). The extent of lung injury was then measured 24 hours later by measurement of BAL bacterial load. This experiment shows that rats treated with exosomes or hMSC had a significantly reduced BAL bacterial load than those treated with PBS vehicle (one way anova $p<0.01$), demonstrating the efficacy of administering exosomes as a treatment and suggests that exosome treatment is comparable to hMSC treatment.

Figure 23:
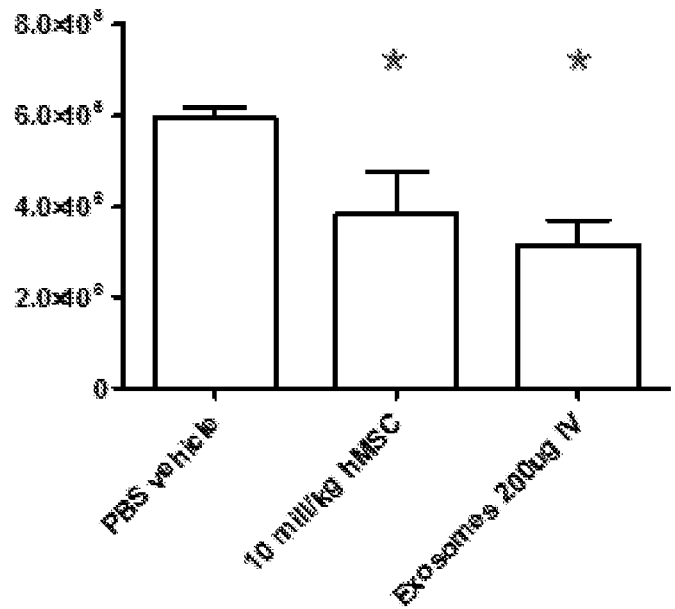
FIG. 23 shows bronchioaveolar lavage (BAL) total cell count in rats treated with PBS vehicle, human mesenchymal stem cells (10 mill/kg), or exosomes (200 µg, IV) in a rat model of ARDS.

FIG. 23 shows bronchioaveolar lavage (BAL) total cell count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200 µg dose of exosomes or 10 million/kg human mesenchymal stem cells (hMSC). The extent of lung injury was then measured 24 hours later by measurement of BAL total cell count. This experiment shows that rats treated with exosomes or hMSC had a significantly reduced BAL total cell count compared to those treated with PBS vehicle (one way anova $p<0.01$), demonstrating the efficacy of administering exosomes as a treatment and suggests that exosome treatment is comparable to hMSC treatment.

Figure 24:
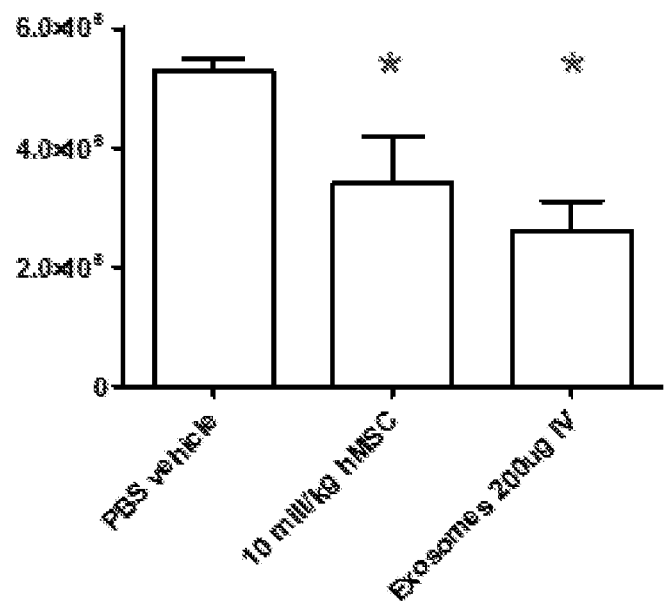
FIG. 24 shows bronchioaveolar lavage (BAL) neutrophil count in rats treated with PBS vehicle, human mesenchymal stem cells (10 mill/kg), or exosomes (200 µg, IV) in a rat model of ARDS.

FIG. 24 shows bronchioaveolar lavage (BAL) neutrophil count in rats treated with PBS vehicle, human mesenchymal stem cells, or exosomes in a rat model of ARDS. In this experiment, 300 g Sprague Dawley rats were given an intrapulmonary dose of E. coli to induce ARDS lung injury, one hour later, the rats were treated intravenously with a 200 µg dose of exosomes or 10 million/kg human mesenchymal stem cells (hMSC). The extent of lung injury was then measured 24 hours later by measurement of BAL neutrophil count. This experiment shows that rats treated with exosomes or hMSC had significantly reduced infiltrating neutrophils in the lung than those treated with PBS vehicle, demonstrating the efficacy of administering exosomes as a treatment and suggests that exosome treatment is comparable to hMSC treatment.

Definitions

In some cases "exosomes" or "microvesicles" used interchangeably herein include cell-derived vesicles, which are released into the extracellular environment by a cell, for example a cultured cell or a cultured stromal cell.

"SDC2," also known as syndecan-2, CD362, S2, or fibroglycan, refers generally herein to the SDC2 polypeptide specified by the sequence listing, or the polypeptide encoded by the SDC2 locus. Syndecan-2, or 'the SDC2 protein' or simply SDC2, is a transmembrane type I heparan sulfate proteoglycan. Additional synonyms for syndecan-2, aside from 'the SDC2 protein' or SDC2, include HSPG, CD362, HSPG1, and SYND2. Generally, as used herein SDC2 refers to the protein or a recognizable fragment thereof unless otherwise indicated, for example by reciting 'the SDC2 gene,' 'the SDC2 transcript,' 'an SDC2 antibody.' Additionally, SDC2 is identified by its polypeptide sequence in the sequence listing that accompanies this specification. An SDC2 fragment refers to any set of consecutive residues of SDC2 that uniquely or recognizably map to the SDC2 polypeptide sequence. In some cases an SDC2 fragment retains some or all activity of the SDC2 protein, or acts as an inhibitor of full length or native SDC2. SDC2 also occasionally refers informally herein to the locus or gene encoding the SDC2 protein. In the event that one of skill in the art is unable to distinguish an SDC2 reference, it is presumed that the term is used herein in reference to the protein or polypeptide rather than to the gene, transcript, or an antibody raised against or binding to SDC2. There is a family of syndecan proteins in mammals. SDC2 is used alternately in reference to a mammalian syndecan-2 or to human SDC2 specifically. In the event that one of skill in the art is unable to distinguish an SDC2 reference, it is presumed that the term is used herein in reference to the human protein or polypeptide.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

The terms "pharmaceutically acceptable", "physiologically tolerable" and grammatical variations thereof, as they refer to compositions, carriers, diluents and reagents, are used interchangeably and in some cases, represent that the materials are capable of administration to or upon a human without the production of undesirable physiological effects to a degree that would prohibit administration of the composition.

A "therapeutically effective amount" in some cases means the amount that, when administered to a subject for treating a disease, is sufficient to effect treatment for that disease.

As used herein, the term "about" a number refers to a range spanning that from 10% less than that number through 10% more than that number, and including values within the range such as the number itself.

As used herein, the term "comprising" an element or elements of a claim refers to those elements but does not preclude the inclusion of an additional element or elements.

The disclosure herein is further clarified in reference to a partial list of numbered embodiments as follows. 1. A composition comprising isolated exosomes, wherein at least 20% of the exosomes comprise SDC2. 2. The composition of embodiment 1, wherein the SDC2 is an exosome surface constituent. 3. The composition of embodiment 1, wherein the SDC2 is an exosome interior constituent. 4. The composition of any one of embodiments 1 to 3, comprising a physiologically acceptable buffer. 5. The composition of any one of embodiments 1 to 4, wherein at least 30% of the exosomes comprise SDC2. 6. The composition of any one of embodiments 1 to 5, wherein at least 40% of the exosomes comprise SDC2. 7. The composition of any one of embodiments 1 to 6, wherein at least 50% of the exosomes comprise SDC2. 8. The composition of any one of embodiments 1 to 7, wherein at least 60% of the exosomes comprise SDC2. 9. The composition of any one of embodiments 1 to 8, wherein at least 70% of the exosomes comprise SDC2. 10. The composition of any one of embodiments 1 to 9, wherein at least 80% of the exosomes comprise SDC2. 11. The composition of any one of embodiments 1 to 10, wherein at least 90% of the exosomes comprise SDC2. 12. The composition of any one of embodiments 1 to 11, wherein at least 95% of the exosomes comprise SDC2. 13. The composition of any one of embodiments 1 to 12, wherein at least 99% of the exosomes comprise SDC2. 14. The composition of any one of embodiments 1 to 13, wherein the exosomes are CD45−. 15. The composition of any one of embodiments 1 to 14, wherein the composition does not comprise a living cell. 16. The composition of any one of embodiments 1 to 15, wherein the composition is non-tumorigenic. 17. The composition of any one of embodiments 1 to 16, wherein the composition is stable for over 48 hours without cryopreservation. 18. The composition of any one of embodiments 1 to 17, wherein the composition comprises SDC2+ mesenchymal stem cells. 19. The composition of any one of embodiments 1 to 18, wherein the composition comprises CD25+ regulatory T cells. 20. The composition of any one of embodiments 1 to 19, wherein the composition comprises CD4+ regulatory T cells. 21. The composition of any one of embodiments 1 to 20, wherein the composition comprises Foxp3+ regulatory T cells. 22. The composition of any one of embodiments 1 to 21, wherein the composition comprises CD25+CD4+Foxp3+ regulatory T cells. 23. The composition of any one of embodiments 1 to 22, wherein the composition comprises CD25+CD4+Foxp3+ regulatory T cells and wherein the composition comprises SDC2+ mesenchymal stem cells. 24. The composition of any one of embodiments 1 to 23, wherein the composition is frozen. 25. The composition of any one of embodiments 1 to 24, wherein the composition is lyophilized. 26. The composition of any one of embodiments 1 to 25, wherein the composition comprises an excipient. 27. The composition of embodiment 26, wherein the excipient comprises at least one of sucrose, trehalose, polyethylene glycol, a polysaccharide, a carrier protein, and an inert protein. 28. The composition of embodiment 26, wherein the excipient comprises at least one of dextran, hydroxyl ethyl starch (HETA), PEG-4000 and gelatin. 29. The composition of embodiment 26, wherein the excipient comprises at least one of PLGA and Eudragit RS 100 Nanoparticles. 30. The composition of any one of embodiments 1 to 29, comprising a therapeutically effective amount of exosomes. 31. The composition of any one of embodiments 1 to 30, comprising at least $10^6$ exosomes. 32. The composition of any one of embodiments 1 to 31, comprising at least $10^7$ exosomes. 33. The composition of any one of embodiments 1 to 32, comprising at least $10^8$ exosomes. 34. The composition of any one of embodiments 1 to 33, comprising at least 1 μg of exosomes. 35. The composition of any one of embodiments 1 to 34, comprising at least 10 μg of exosomes. 36. The composition of any one of embodiments 1 to 35, comprising at least 20 μg of exosomes. 37. The composition of any one of embodiments 1 to 36, comprising at least 50 μg of exosomes. 38. The composition of any one of embodiments 1 to 37, comprising at least 100 μg of exosomes. 39. The composition of any one of embodiments 1 to 38, comprising at least 150 μg of exosomes. 40. The composition of any one of embodiments 1 to 39, comprising at least 200 μg of exosomes. 41. The composition of any one of embodiments 1 to 40, comprising at least 250 μg of exosomes. 42. The composition of any one of embodiments 1 to 41, comprising at least 500 μg of exosomes. 43. The composition of any one of embodiments 1 to 42, comprising at least 750 μg of exosomes. 44. The composition of any one of embodiments 1 to 43, comprising at least 1 mg of exosomes. 45. The composition of any one of embodiments 1 to 44, comprising at least 2 mg of exosomes. 46. The composition of any one of embodiments 1 to 45, comprising at least 3 mg of exosomes. 47. The composition of any one of embodiments 1 to 46, comprising at least 4 mg of exosomes. 48. The composition of any one of embodiments 1 to 47, comprising at least 5 mg of exosomes. 49. The composition of any one of embodiments 1 to 48, comprising at least 6 mg of exosomes. 50. The composition of any one of embodiments 1 to 49, comprising at least 7 mg of exosomes. 51. The composition of any one of embodiments 1 to 50, comprising at least 100 mg of exosomes. 52. The composition of any one of embodiments 1 to 51, comprising at least 200 mg of exosomes. 53. The composition of any one of embodiments 1 to 52, comprising at least 300 mg of exosomes. 54. The composition of any one of embodiments 1 to 53, comprising at least 400 mg of exosomes. 55. The composition of any one of embodiments 1 to 54, comprising at least 500 mg of exosomes. 56. The composition of any one of embodiments 1 to 55, comprising at least 600 mg of exosomes. 57. The composition of any one of embodiments 1 to 56, comprising at least 700 mg of exosomes.

58. The composition of any one of embodiments 1 to 57, wherein the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. 59. The composition of any one of embodiments 1 to 58, wherein the composition comprises an immunosuppressive drug. 60. The composition of embodiment 59, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. 61. The composition of embodiment 60, wherein the immunosuppressive drug comprises an anti-TNF antibody. 62. The composition of embodiment 60, wherein the immunosuppressive drug comprises a TNF inhibitor. 63. The composition of embodiment 60, wherein the immunosuppressive drug comprises an NSAID. 64. The composition of embodiment 60, wherein the immunosuppressive drug comprises a steroid. 65. The composition of any one of embodiments 1 to 64, wherein the exosomes are purified. 66. The composition of any one of embodiments 1 to 65, wherein the exosomes are in vitro. 67. The composition of any one of embodiments 1 to 66, wherein the exosomes are paracrine signaling exosomes. 68. The composition of any one of embodiments 1 to 67, wherein the exosomes are capable of crossing the blood brain barrier. 69. A method of treating at least one symptom of diabetes in a subject comprising delivering a composition comprising purified SDC2+ exosomes to the subject. 70. The method of embodiment 69, wherein the diabetes is selected from type 1 diabetes and type 2 diabetes. 71. The method of embodiment 69 or embodiment 70, wherein the exosomes are paracrine signaling exosomes. 72. The method of any one of embodiments 69 to 71, wherein delivering comprises injecting the composition comprising purified SDC2+ exosomes. 73. The method of embodiment 72, wherein the injecting is selected from at least one of intravenous injecting, lymph node injecting, subcutaneous injecting, intraperitoneal injecting, and intramuscular injecting. 74. The method of embodiment 72, wherein the injecting is intravenous injecting. 75. The method of any one of embodiments 69 to 73, wherein at least one of said purified SDC2+ exosomes contains an antigen, and wherein said antigen is not exposed to a recipient's humoral immune system. 76. The method of any one of embodiments 69 to 75, wherein at least 20% of the exosomes comprise SDC2. 77. The method of any one of embodiments 69 to 76, wherein at least 30% of the exosomes comprise SDC2. 78. The method of any one of embodiments 69 to 77, wherein at least 40% of the exosomes comprise SDC2. 79. The method of any one of embodiments 69 to 78, wherein at least 50% of the exosomes comprise SDC2. 80. The method of any one of embodiments 69 to 79, wherein at least 60% of the exosomes comprise SDC2. 81. The method of any one of embodiments 69 to 80, wherein at least 70% of the exosomes comprise SDC2. 82. The method of any one of embodiments 69 to 81, wherein at least 80% of the exosomes comprise SDC2. 83. The method of any one of embodiments 69 to 82, wherein at least 90% of the exosomes comprise SDC2. 84. The method of any one of embodiments 69 to 83, wherein at least 95% of the exosomes comprise SDC2. 85. The method of any one of embodiments 69 to 84, wherein at least 99% of the exosomes comprise SDC2. 86. The method of any one of embodiments 69 to 85, wherein the exosomes are CD45−. 87. The method of any one of embodiments 69 to 86, wherein the composition comprises SDC2+ mesenchymal stem cells. 88. The composition of any one of embodiments 69 to 87, wherein the composition comprises CD25+ regulatory T cells. 89. The composition of any one of embodiments 69 to 88, wherein the composition comprises CD4+ regulatory T cells. 90. The composition of any one of embodiments 69 to 89, wherein the composition comprises Foxp3+ regulatory T cells. 91. The composition of any one of embodiments 69 to 90, wherein the composition comprises CD25+CD4+Foxp3+ regulatory T cells. 92. The method of any one of embodiments 69 to 91, wherein the composition is frozen. 93. The method of any one of embodiments 69 to 92, wherein the composition is lyophilized. 94. The method of any one of embodiments 69 to 93, comprising delivering a therapeutically effective amount of exosomes. 95. The method of any one of embodiments 69 to 94, comprising delivering at least $10^6$ exosomes. 96. The method of any one of embodiments 69 to 95, comprising delivering at least $10^7$ exosomes. 97. The method of any one of embodiments 69 to 96, comprising delivering at least $10^8$ exosomes. 98. The method of any one of embodiments 69 to 97, comprising delivering at least 1 µg of exosomes. 99. The method of any one of embodiments 69 to 98, comprising delivering at least 10 µg of exosomes. 100. The method of any one of embodiments 69 to 99, comprising delivering at least 20 µg of exosomes. 101. The method of any one of embodiments 69 to 100, comprising delivering at least 50 µg of exosomes. 102. The method of any one of embodiments 69 to 101, comprising delivering at least 100 µg of exosomes. 103. The method of any one of embodiments 69 to 102, comprising delivering at least 150 µg of exosomes. 104. The method of any one of embodiments 69 to 103, comprising delivering at least 200 µg of exosomes. 105. The method of any one of embodiments 69 to 104, comprising delivering at least 250 µg of exosomes. 106. The method of any one of embodiments 69 to 105, comprising delivering at least 500 µg of exosomes. 107. The method of any one of embodiments 69 to 106, comprising delivering at least 750 µg of exosomes. 108. The method of any one of embodiments 69 to 107, comprising delivering at least 1 mg of exosomes. 109. The method of any one of embodiments 69 to 108, comprising delivering at least 2 mg of exosomes. 110. The method of any one of embodiments 69 to 109, comprising delivering at least 3 mg of exosomes. 111. The method of any one of embodiments 69 to 110, comprising delivering at least 4 mg of exosomes. 112. The method of any one of embodiments 69 to 111, comprising delivering at least 5 mg of exosomes. 113. The method of any one of embodiments 69 to 112, comprising delivering at least 6 mg of exosomes. 114. The method of any one of embodiments 69 to 113, comprising delivering at least 7 mg of exosomes. 115. The method of any one of embodiments 69 to 114, comprising delivering at least 100 mg of exosomes. 116. The method of any one of embodiments 69 to 115, comprising delivering at least 200 mg of exosomes. 117. The method of any one of embodiments 69 to 116, comprising delivering at least 300 mg of exosomes. 118. The method of any one of embodiments 69 to 117, comprising delivering at least 400 mg of exosomes. 119. The method of any one of embodiments 69 to 118, comprising delivering at least 500 mg of exosomes. 120. The method of any one of embodiments 69 to 119, comprising delivering at least 600 mg of exosomes. 121. The method of any one of embodiments 69 to 120, comprising delivering at least 700 mg of exosomes. 122. The method of any one of embodiments 69 to 121, wherein the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. 123. The method of any one of embodiments 69 to 122, wherein the composition comprises an immunosuppressive drug. 124. The method of embodiment 123, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. 125. The method of any one of embodiments 69 to 124, wherein the method reduces need for insulin in the subject. 126. The method of any one of embodiments 69 to 124, wherein the method increases insulin sensitivity in the subject. 127. The method of any one of embodiments 69 to 126, wherein the method reduces inflammation in the subject. 128. A method of modulating an inflammation response in a mammal comprising delivering a composition comprising purified SDC2+ exosomes to a site of the inflammation response. 129. The method of embodiment 128, wherein the exosomes are paracrine signaling exosomes. 130. The method of embodiment 128 or embodiment 129, wherein said delivering comprises injecting said composition comprising purified SDC2+ exosomes. 131. The method of embodiment 128 or embodiment 129, wherein said delivering comprises topically applying said composition comprising purified SDC2+ exosomes. 132. The method of embodiment 131, wherein said composition comprises a hydrogel or collagen gel. 133. The method of embodiment 128 or embodiment 129, wherein said delivering comprises intraocularly administering said composition comprising purified SDC2+ exosomes. 134. The method of embodiment 128 or embodiment 129, wherein said delivering comprises ophthalmic application of said composition comprising purified SDC2+ exosomes. 135. The method of embodiment 128 or embodiment 129, wherein said delivering comprises intravenous delivery of said composition comprising purified SDC2+ exosomes. 136. The method of embodiment 128 or embodiment 129, wherein said injecting comprises injecting directly into lymph nodes of a patient. 137. The method of embodiment 128 or embodiment 129, wherein said delivering comprises subcutaneous delivery of said composition comprising purified SDC2+ exosomes. 138. The method of embodiment 128 or embodiment 129, wherein said delivering comprises intraperitoneal delivery of said composition comprising purified SDC2+ exosomes. 139. The method of embodiment 128 or embodiment 129, wherein said delivering comprises intrathecal delivery of said composition comprising purified SDC2+ exosomes. 140. The method of embodiment 128 or embodiment 129, wherein said delivering comprises inhalation. 141. The method of embodiment 140, wherein inhalation comprises use of an inhalation device. 142. The method of embodiments 141, wherein the inhalation device is a nebulizer. 143. The method of embodiment 128 or embodiment 129, wherein delivering comprises direct cardiac administration. 144. The method of embodiment 128 or embodiment 129, wherein the exosomes cross the blood brain barrier. 145. The method of any one of embodiments 128 to 144, wherein at least one of said purified SDC2+ exosomes contains an antigen, and wherein said antigen is not exposed to a recipient's humoral immune system. 146. The method of any one of embodiments 128 to 145, wherein at least 20% of the exosomes comprises SDC2. 147. The method of any one of embodiments 128 to 146, comprising a physiologically acceptable buffer. 148. The method of any one of embodiments 128 to 147, wherein at least 30% of the exosomes comprise SDC2. 149. The method of any one of embodiments 128 to 148, wherein at least 40% of the exosomes comprise SDC2. 150. The method of any one of embodiments 128 to 149, wherein at least 50% of the exosomes comprise SDC2. 151. The method of any one of embodiments 128 to 150, wherein at least 60% of the exosomes comprise SDC2. 152. The method of any one of embodiments 128 to 151, wherein at least 70% of the exosomes comprise SDC2. 153. The method of any one of embodiments 128 to 152, wherein at least 80% of the exosomes comprise SDC2. 154. The method of any one of embodiments 128 to 153, wherein at least 90% of the exosomes comprise SDC2. 155. The method of any one of embodiments 128 to 154, wherein at least 95% of the exosomes comprise SDC2. 156. The method of any one of embodiments 128 to 155, wherein at least 99% of the exosomes comprise SDC2. 157. The method of any one of embodiments 128 to 156, wherein the exosomes are CD45−. 158. The method of any one of embodiments 128 to 157, wherein the composition does not comprise a living cell. 159. The method of any one of embodiments 128 to 158, wherein the composition comprises SDC2+ mesenchymal stem cells. 160. The method of any one of embodiments 128 to 159, wherein the composition comprises CD25+ regulatory T cells. 161. The method of any one of embodiments 128 to 160, wherein the composition comprises CD4+ regulatory T cells. 162. The method of any one of embodiments 128 to 161, wherein the composition comprises Foxp3+ regulatory T cells. 163. The method of any one of embodiments 128 to 162, wherein the composition comprises CD25+CD4+Foxp3+ regulatory T cells. 164. The method of any one of embodiments 128 to 163, wherein the composition comprises CD25+CD4+Foxp3+ regulatory T cells and wherein the composition comprises SDC2+ mesenchymal stem cells. 165. The method of any one of embodiments 128 to 164, wherein the composition is frozen. 166. The method of any one of embodiments 128 to 165, wherein the composition is lyophilized. 167. The method of any one of embodiments 128 to 166, comprising delivering at least 10^6 exosomes. 168. The method of any one of embodiments 128 to 167, comprising delivering a therapeutically effective amount of exosomes. 169. The method of any one of embodiments 128 to 168, comprising delivering at least 10^6 exosomes. 170. The method of any one of embodiments 128 to 169, comprising delivering at least 10^7 exosomes. 171. The method of any one of embodiments 128 to 170, comprising delivering at least 10^8 exosomes. 172. The method of any one of embodiments 128 to 171, comprising delivering at least 1 μg of exosomes. 173. The method of any one of embodiments 128 to 172, comprising delivering at least 10 μg of exosomes. 174. The method of any one of embodiments 128 to 173, comprising delivering at least 20 μg of exosomes. 175. The method of any one of embodiments 128 to 174, comprising delivering at least 50 μg of exosomes. 176. The method of any one of embodiments 128 to 175, comprising delivering at least 100 μg of exosomes. 177. The method of any one of embodiments 128 to 176, comprising delivering at least 150 μg of exosomes. 178. The method of any one of embodiments 128 to 177, comprising delivering at least 200 μg of exosomes. 179. The method of any one of embodiments 128 to 178, comprising delivering at least 250 μg of exosomes. 180. The method of any one of embodiments 128 to 179, comprising delivering at least 500 μg of exosomes. 181. The method of any one of embodiments 128 to 180, comprising delivering at least 750 μg of exosomes. 182. The method of any one of embodiments 128 to 181, comprising delivering at least 1 mg of exosomes. 183. The method of any one of embodiments 128 to 182, comprising delivering at least 2 mg of exosomes. 184. The method of any one of embodiments 128 to 183, comprising delivering at least 3 mg of exosomes. 185. The method of any one of embodiments 128 to 184, comprising delivering at least 4 mg of exosomes. 186. The method of any one of embodiments 128 to 185, comprising delivering at least 5 mg of exosomes. 187. The method of any one of embodiments 128 to 186, comprising delivering at least 6 mg of exosomes. 188. The method of any one of embodiments 128 to 187, comprising delivering at least 7 mg of exosomes. 189. The method of any one of embodiments 128 to 188, comprising delivering at least 100 mg of exosomes. 190. The method of any one of embodiments 128 to 189, comprising delivering at least 200 mg of exosomes. 191. The method of any one of embodiments 128 to 190, comprising delivering at least 300 mg of exosomes. 192. The method of any one of embodiments 128 to 191, comprising delivering at least 400 mg of exosomes. 193. The method of any one of embodiments 128 to 192, comprising delivering at least 500 mg of exosomes. 194. The method of any one of embodiments 128 to 193, comprising delivering at least 600 mg of exosomes. 195. The method of any one of embodiments 128 to 194, comprising delivering at least 700 mg of exosomes. 196. The method of any one of embodiments 128 to 195, wherein the composition comprises at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. 197. The method of any one of embodiments 128 to 196, wherein the composition comprises an immunosuppressive drug. 198. The method of embodiment 197, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. 199. The method of embodiment 197, wherein the immunosuppressive drug comprises an anti-TNF antibody. 200. The method of embodiment 197, wherein the immunosuppressive drug comprises a TNF inhibitor. 201. The method of embodiment 197, wherein the immunosuppressive drug comprises an NSAID. 202. The method of embodiment 197, wherein the immunosuppressive drug comprises a steroid. 203. The method of any one of embodiments 128 to 202, wherein the inflammation response comprises an immune response. 204. The method of embodiment 203, wherein the immune response comprises an autoimmune response. 205. The method of embodiment 203, wherein the immune response comprises at least one of type 1 diabetes, type 2 diabetes, sepsis, Crohn's disease, inflammatory bowel syndrome, rheumatoid arthritis, and graft-host disease. 206. The method of any one of embodiments 128 to 205, wherein the inflammation response comprises at least one of multiple sclerosis, ALS, and a motor neuron disorder. 207. The method of any one of embodiments 128 to 206, wherein the inflammation response comprises at least one of a dermal wound, a bone fracture, a concussion wound, and a burn. 208. The method of any one of embodiments 128 to 207, wherein the inflammation response comprises a diabetic complication. 209. The method of embodiment 208, wherein the diabetic complication comprises at least one of atherosclerosis, nephropathy, cardiomyopathy, neuropathy, a kidney disorder, kidney failure, a diabetic ulcer, and a leg ulcer. 210. The method of any one of embodiments 128 to 209, wherein the inflammation response comprises at least one of ARDS and sepsis. 211. The method of any one of embodiments 128 to 210, wherein the inflammation response comprises at least one of osteoarthritis and a bone fracture. 212. The method of any one of embodiments 128 to 211, wherein the inflammation response comprises an inflammatory liver disease. 213. The method of any one of embodiments 128 to 212, wherein the inflammation response comprises a heart disorder. 214. The method of embodiment 213, wherein the heart disorder comprises at least one of Myocarditis, Postmyocardial infarction syndrome, Postpericardiotomy syndrome, and Subacute bacterial endocarditis. 215. The method of any one of embodiments 128 to 214, wherein the inflammation response comprises a kidney disorder. 216. The method of embodiment 215, wherein the kidney disorder comprises at least one of Anti-Glomerular Basement Membrane nephritis, Interstitial cystitis, and Lupus nephritis. 217. The method of any one of embodiments 128 to 216, wherein the inflammation response comprises a liver disorder. 218. The method of embodiment 217, wherein the liver disorder comprises at least one of autoimmune hepatitis, Primary biliary cirrhosis, and Primary sclerosing cholangitis. 219. The method of any one of embodiments 128 to 218, wherein the inflammation response comprises a lung disorder. 220. The method of any one of embodiments 128 to 219, wherein the inflammation response comprises at least one of ARDS, Antisynthetase syndrome, asthma, chronic obstructive pulmonary disease, cystic fibrosis, atelectasis, bronchitis, emphysema, pneumonia, and pulmonary edema. 221. The method of any one of embodiments 128 to 220, wherein the inflammation response comprises a skin disorder. 222. The method of embodiment 221, wherein the skin disorder comprises at least one of Alopecia Areata, autoimmune Angioedema, autoimmune progesterone dermatitis, autoimmune urticaria, Bullous pemphigoid, Cicatricial pemphigoid, Dermatitis herpetiformis, Discoid lupus erythematosus, *Epidermolysis bullosa acquisita, Erythema nodosum, Gestational pemphigoid, Hidradenitis suppurativa, Lichen planus, Lichen sclerosus*, Linear IgA disease, Morphea, *Pemphigus vulgaris, Pityriasis lichenoides* et *varioliformis acuta*, Mucha-Habermann disease, Psoriasis, Systemic scleroderma, Vitiligo, Addison's disease, autoimmune polyendocrine syndrome, autoimmune polyendocrine syndrome type 2, and autoimmune polyendocrine syndrome type 3. 223. The method of any one of embodiments 128 to 222, wherein the inflammation response comprises a pancreas disorder. 224. The method of embodiment 223, wherein the pancreas disorder comprises at least one of, autoimmune pancreatitis and Diabetes mellitus type 1. 225. The method of any one of embodiments 128 to 224, wherein the inflammation response comprises a thyroid disorder. 226. The method of embodiment 225, wherein the thyroid disorder comprises at least one of autoimmune thyroiditis, Ord's thyroiditis and Graves' disease. 227. The method of any one of embodiments 128 to 226, wherein the inflammation response comprises an exocrine disorder. 228. The method of embodiment 227, wherein the exocrine disorder comprises at least one of a Reproductive Organ disorder, autoimmune oophoritis, Endometriosis, and autoimmune orchitis. 229. The method of any one of embodiments 128 to 228, wherein the inflammation response comprises a salivary gland disorder. 230. The method of any one of embodiments 128 to 229, wherein the inflammation response comprises Sjogren's syndrome. 231. The method of any one of embodiments 128 to 230, wherein the inflammation response comprises a digestive system disorder. 232. The method of embodiment 231, wherein the digestive system disorder comprises at least one of autoimmune enteropathy, Celiac disease, Crohn's disease, Microscopic colitis, and Ulcerative colitis. 233. The method of any one of embodiments 128 to 232, wherein the inflammation response comprises a blood disorder. 234. The method of embodiment 233, wherein the blood disorder comprises at least one of Antiphospholipid syndrome, Aplastic anemia, autoimmune hemolytic anemia, autoimmune lymphoproliferative syndrome, autoimmune neutropenia, autoimmune thrombocytopenic purpura, Cold agglutinin disease, Essential mixed cryoglobulinemia, Evans syndrome, IgG4-related systemic disease, Paroxysmal nocturnal hemoglobinuria, Pernicious anemia, Pure red cell aplasia, and Thrombocytopenia. 235. The method of any one of embodiments 128 to 234, wherein the inflammation response comprises a connective tissue, multi-organ or systemic disorder. 236. The method of embodiment 235, wherein the disorder comprises at least one of Adiposis dolorosa, Adult-onset Still's disease, Ankylosing Spondylitis, CREST syndrome, Drug-induced lupus, Enthesitis-related arthritis, Eosinophilic fasciitis, Felty syndrome, Juvenile Arthritis, Lyme disease (Chronic), Mixed connective tissue disease, Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus, and Undifferentiated connective tissue disease. 237. The method of any one of embodiments 128 to 236, wherein the inflammation response comprises a muscle disorder. 238. The method of any one of embodiments 128 to 237, wherein the inflammation response comprises cachexia. 239. The method of any one of embodiments 128 to 238, wherein the inflammation response comprises sarcophenia. 240. The method of any one of embodiments 128 to 239, wherein the inflammation response comprises at least one of Dermatomyositis, Fibromyalgia, Inclusion body myositis, Myositis, Myasthenia gravis, Neuromyotonia, Paraneoplastic cerebellar degeneration, and Polymyositis. 241. The method of any one of embodiments 128 to 240, wherein the inflammation response comprises a nervous system disorder. 242. The method of embodiment 241, wherein the nervous system disorder comprises at least one of Acute disseminated encephalomyelitis, Acute motor axonal neuropathy, Anti-N-Methyl-D-Aspartate Receptor Encephalitis, Balo concentric sclerosis, Bickerstaffs encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Pediatric Autoimmune Neuropsychiatric Disorder Associated with *Streptococcus*, Progressive inflammatory neuropathy, Restless leg syndrome, Stiff person syndrome, Sydenham chorea, amyotrophic lateral sclerosis, Parkinson's disease, Alzheimer's disease, and Transverse myelitis. 243. The method of any one of embodiments 128 to 242, wherein the inflammation response comprises an eye disorder. 244. The method of embodiment 243, wherein the eye disorder comprises at least one of autoimmune retinopathy, autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, and Tolosa-Hunt syndrome. 245. The method of any one of embodiments 128 to 244, wherein the inflammation response comprises an ear disorder. 246. The method of embodiment 245, wherein the ear disorder comprises at least one of autoimmune inner ear disease and Meniere's disease. 247. The method of any one of embodiments 128 to 246, wherein the inflammation response comprises a vascular system disorder. 248. The method of embodiment 247, wherein the vascular system disorder comprises at least one of Anti-neutrophil cytoplasmic antibody-associated vasculitis, Behcet's disease, Churg-Strauss syndrome, Giant cell arteritis, Henoch-Schonlein purpura, Kawasaki's disease, Leukocytoclastic vasculitis, Lupus vasculitis, Rheumatoid vasculitis, Microscopic polyangiitis, *Polyarteritis nodosa*, Polymyalgia rheumatica, Urticarial vasculitis, and Vasculitis. 249. A method of obtaining an immuno-modulatory composition comprising exosomes, comprising obtaining exosomes having SDC2 at a frequency of at least 20%. 250. The method of embodiment 249, wherein the exosomes are paracrine signaling exosomes. 251. The method of embodiment 249 or embodiment 250, wherein the SDC2 is an exosome surface constituent. 252. The method of embodiment 249 or embodiment 250, wherein the SDC2 is an exosome interior constituent. 253. The method of any one of embodiments 249 to 252, wherein the exosomes having SDC2 at a frequency of at least 20% are derived from at least one SDC2+ stromal cell. 254. The method of embodiment 253, comprising transforming the at least one SDC2+ stromal cell to overexpress SDC2/S2/CD362/fibroglycan. 255. The method of embodiment 253, comprising irradiating the at least one SDC2+ stromal cell. 256. The method of embodiment 255, comprising irradiating using gamma-irradiation. 257. The method of embodiment 253, comprising subjecting the at least one SDC2+ stromal cell to inflammatory stimulation. 258. The method of embodiment 257, wherein the inflammatory stimulation comprises at least one of TNF-alpha, Interferon-gamma, Interferon-beta, Interleukin-1b, TLR agonists, Poly I:C, and LPS. 259. The method of embodiment 253, comprising subjecting the at least one SDC2+ stromal cell to growth arrest. 260. The method of embodiment 259, wherein the growth arrest comprises at least one or gamma-irradiation, mitomycin-c, TGFb stimulation, and growing cells to confluence. 261. The method of any one of embodiments 249 to 260, comprising providing a physiologically acceptable buffer. 262. The method of any one of embodiments 249 to 261, wherein at least 30% of the exosomes comprise SDC2. 263. The method of any one of embodiments 249 to 262, wherein at least 40% of the exosomes comprise SDC2. 264. The method of any one of embodiments 249 to 263, wherein at least 50% of the exosomes comprise SDC2. 265. The method of any one of embodiments 249 to 264, wherein at least 60% of the exosomes comprise SDC2. 266. The method of any one of embodiments 249 to 265, wherein at least 70% of the exosomes comprise SDC2. 267. The method of any one of embodiments 249 to 266, wherein at least 80% of the exosomes comprise SDC2. 268. The method of any one of embodiments 249 to 267, wherein at least 90% of the exosomes comprise SDC2. 269. The method of any one of embodiments 249 to 268, wherein at least 95% of the exosomes comprise SDC2. 270. The method of any one of embodiments 249 to 269, wherein at least 99% of the exosomes comprise SDC2. 271. The method of any one of embodiments 249 to 270, wherein the exosomes are CD45−. 272. The method of any one of embodiments 249 to 271, wherein the composition does not comprise a living cell. 273. The method of any one of embodiments 249 to 272, wherein the composition is non-tumorigenic. 274. The method of any one of embodiments 249 to 273, wherein the composition is stable for over 48 hours without cryopreservation. 275. The method of any one of embodiments 249 to 274, wherein the composition comprises SDC2+ mesenchymal stem cells. 276. The method of any one of embodiments 249 to 275, wherein the composition is frozen. 277. The method of any one of embodiments 249 to 276, wherein the composition is lyophilized. 278. The method of any one of embodiments 249 to 277, wherein a therapeutically active amount of exosomes are obtained. 279. The method of any one of embodiments 249 to 278, wherein at least 10^6 exosomes are obtained. 280. The method of any one of embodiments 249 to 279, wherein at least 10^7 exosomes are obtained. 281. The method of any one of embodiments 249 to 280, wherein at least 10^8 exosomes are obtained. 282. The method of any one of embodiments 249 to 281, wherein at least 1 μg of exosomes are obtained. 283. The method of any one of embodiments 249 to 282, wherein at least 10 μg of exosomes are obtained. 284. The method of any one of embodiments 249 to 283, wherein at least 20 μg of exosomes are obtained. 285. The method of any one of embodiments 249 to 284, wherein at least 50 μg of exosomes are obtained. 286. The method of any one of embodiments 249 to 285, wherein at least 100 μg of exosomes are obtained. 287. The method of any one of embodiments 249 to 286, wherein at least 150 μg of exosomes are obtained. 288. The method of any one of embodiments 249 to 287, wherein at least 200 μg of exosomes are obtained. 289. The method of any one of embodiments 249 to 288, wherein at least 250 μg of exosomes are obtained. 290. The method of any one of embodiments 249 to 289, wherein at least 500 μg of exosomes are obtained. 291. The method of any one of embodiments 249 to 290, wherein at least 750 μg of exosomes are obtained. 292. The method of any one of embodiments 249 to 291, wherein at least 1 mg of exosomes are obtained. 293. The method of any one of embodiments 249 to 292, wherein at least 2 mg of exosomes are obtained. 294. The method of any one of embodiments 249 to 293, wherein at least 3 mg of exosomes are obtained. 295. The method of any one of embodiments 249 to 294, wherein at least 4 mg of exosomes are obtained. 296. The method of any one of embodiments 249 to 295, wherein at least 5 mg of exosomes are obtained. 297. The method of any one of embodiments 249 to 296, wherein at least 6 mg of exosomes are obtained. 298. The method of any one of embodiments 249 to 297, wherein at least 7 mg of exosomes are obtained. 299. The method of any one of embodiments 249 to 298, wherein at least 100 mg of exosomes are obtained. 300. The method of any one of embodiments 249 to 299, wherein at least 200 mg of exosomes are obtained. 301. The method of any one of embodiments 249 to 300, wherein at least 300 mg of exosomes are obtained. 302. The method of any one of embodiments 249 to 301, wherein at least 400 mg of exosomes are obtained. 303. The method of any one of embodiments 249 to 302, wherein at least 500 mg of exosomes are obtained. 304. The method of any one of embodiments 249 to 303, wherein at least 600 mg of exosomes are obtained. 305. The method of any one of embodiments 249 to 304, wherein at least 700 mg of exosomes are obtained. 306. The method of any one of embodiments 249 to 305, wherein the exosomes are purified. 307. The method of any one of embodiments 249 to 306, wherein the exosomes are isolated. 308. The method of any one of embodiments 249 to 307, wherein the SDC2+ stromal cells are cultured in a hollow-fiber bioreactor. 309. A method of isolating an immuno-modulatory composition comprising the steps of obtaining a composition comprising exosomes; contacting the composition to an anti-SDC2 antibody; and retaining exosomes bound to the anti-SDC2 antibody. 310. The method of embodiment 308, wherein the exosomes are paracrine signaling exosomes. 311. The method of embodiment 308 or embodiment 310, wherein the composition comprising exosomes is obtained from a cell culture comprising mesenchymal stem cells. 312. The method of embodiment 311, wherein the cell culture comprising mesenchymal stem cells comprises SDC2+ cells. 313. The method of embodiment 311 or embodiment 312, wherein the cell culture comprising mesenchymal stem cells comprises CD45− cells. 314. The method of any one of embodiments 311 to 313, wherein the cell culture comprising mesenchymal stem cells comprises SDC2+ mesenchymal stem cells. 315. The method of any one of embodiments 311 to 314, wherein the cell culture comprising mesenchymal stem cells is enriched for SDC2+ cells. 316. The method of any one of embodiments 311 to 315, wherein the cell culture comprising mesenchymal stem cells is enriched for SDC2+ mesenchymal stem cells. 317. The method of any one of embodiments 308 to 316, wherein retaining exosomes bound to the anti-SDC2 antibody comprises storage at room-temperature. 318. The method of any one of embodiments 308 to 317, wherein retaining exosomes bound to the anti-SDC2 antibody comprises storage without cryogenic preservation. 319. The method of any one of embodiments 308 to 318, wherein retaining exosomes bound to the anti-SDC2 antibody comprises freezing the exosomes. 320. A method of isolating an immuno-modulatory composition comprising the steps of obtaining a cell population enriched for SDC2+ cells; recovering a supernatant from said cell population; and obtaining an exosome fraction from the supernatant. 321. The method of embodiment 320, wherein the exosomes are paracrine signaling exosomes. 322. The method of embodiment 320 or embodiment 321, wherein the SDC2+ cells comprise mesenchymal stem cells. 323. The method of any one of embodiments 320 to 322, wherein the SDC2+ cells comprise CD45− cells. 324. The method of any one of embodiments 320 to 323, wherein obtaining an exosome fraction comprises centrifuging the supernatant. 325. The method of embodiment 324, wherein the centrifugation comprises centrifuging the cells at about 100,000 g for at least 1 hr. 326. The method of embodiment 324 or embodiment 325, wherein the centrifugation comprises ultrafiltration. 327. The method of any one of embodiments 324 to 326, wherein the centrifugation comprises size-exclusion liquid chromatography. 328. The method of any one of embodiments 320 to 327, wherein obtaining an exosome fraction comprises ultrafiltration. 329. The method of any one of embodiments 320 to 328, wherein obtaining an exosome fraction comprises size-exclusion liquid chromatography. 330. The method of any one of embodiments 320 to 329, wherein obtaining an exosome fraction comprises contacting the supernatant to an anti-SDC2 antibody. 331. The method of any one of embodiments 320 to 330, comprising storing the exosome fraction at room-temperature. 332. The method of any one of embodiments 320 to 331, comprising storing the exosome fraction without cryogenic preservation. 333. The method of any one of embodiments 320 to 332, comprising adding an immunosuppressive drug to the immuno-modulatory composition. 334. The method of embodiment 333, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. 335. The method of any one of embodiments 320 to 334, wherein the cell population enriched for SDC2+ cells is perturbed to elicit exosome production. 336. The method of embodiment 335, comprising transforming the cell population enriched for SDC2+ cells to overexpress SDC2/S2/CD362/fibroglycan. 337. The method of embodiment 335 or embodiment 336, comprising irradiating cell population enriched for SDC2+ cells. 338. The method of embodiment 337, comprising irradiating using gamma-irradiation. 339. The method of any one of embodiments 335 to 338, comprising subjecting the cell population enriched for SDC2+ cells to inflammatory stimulation. 340. The method of embodiment 339, wherein the inflammatory stimulation comprises at least one of TNF-alpha, Interferon-gamma, Interferon-beta, Interleukin-1b, TLR agonists, Poly I:C, and LPS. 341. The method of any one of embodiments 335 to 340, comprising subjecting the cell population enriched for SDC2+ cells to growth arrest. 342. The method of embodiment 341, wherein the growth arrest comprises at least one or gamma-irradiation, mitomycin-c, TGFb stimulation, and growing cells to confluence. 343. The method of any one of embodiments 308 to 342, wherein the cell population is cultured in a hollow-fiber bioreactor. 344. A method of delivering an immuno-modulatory signal to an intracellular space of a mammal, comprising the steps of obtaining a population of exosomes from a SDC2+ mesenchymal stem cell; and administering the population of exosomes to the mammal; wherein the population of exosomes contains the immuno-modulatory signal; and wherein contents of the exosomes are delivered to an intracellular space of the mammal without eliciting a humoral immune response to the contents of the exosome in the mammal. 345. The method of embodiment 344, wherein the exosomes are paracrine signaling exosomes. 346. The method of embodiment 344 or embodiment 345, wherein the population of exosomes is drawn into an intracellular space of a mammal by phagocytosis. 347. The method of any one of embodiments 344 to 346, wherein the population of exosomes is drawn into an intracellular space of a mammal by endocytosis. 348. The method of any one of embodiments 344 to 347, wherein the population of exosomes is drawn into an intracellular space of a mammal by fusion. 349. The method of any one of embodiments 344 to 348, wherein the administering comprises injecting the population into the mammal. 350. The method of any one of embodiments 344 to 349, wherein the administering comprises topically applying said composition comprising purified SDC2+ exosomes. 351. The method of any one of embodiments 344 to 350, wherein the administering comprises a hydrogel or collagen gel. 352. The method of any one of embodiments 344 to 351, wherein the administering comprises intraocularly applying said composition comprising purified SDC2+ exosomes. 353. The method of any one of embodiments 344 to 352, wherein the administering comprises ophthalmic application of said composition comprising purified SDC2+ exosomes. 354. The method of any one of embodiments 344 to 353, wherein the administering comprises injecting said composition comprising purified SDC2+ exosomes. 355. The method of embodiment 354, wherein said injecting comprises injecting directly into lymph nodes of a patient. 356. The method of any one of embodiments 344 to 355, wherein said delivering comprises subcutaneous delivery of said composition comprising purified SDC2+ exosomes. 357. The method of any one of embodiments 344 to 356, wherein said delivering comprises peritoneal delivery of said composition comprising purified SDC2+ exosomes. 358. The method of any one of embodiments 344 to 357, wherein said delivering comprises inhalation. 359. The method of embodiment 358, wherein inhalation comprises use of an inhalation device. 360. The method of embodiments 359, wherein the inhalation device is a nebulizer. 361. The method of any one of embodiments 344 to 360, comprising administering an immunosuppressive drug. 362. The method of embodiment 361, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. 363. The method of any one of embodiments 344 to 362, wherein the population of exosomes comprises an exosome containing at least one of IL12, suppressor of cytokine signaling (SOCS), p53, PTEN, CD52, tsc1, Foxp3, Soluble Immune Response Suppressor (SIRS), TGFB, CD39, CD39L3, CD73, and maspin. 364. The method of any one of embodiments 344 to 363, wherein the exosome protein constituent is not detected by the host humoral immune system. 365. The method of any one of embodiments 344 to 364, wherein obtaining the population of exosomes comprises freezing the population of exosomes. 366. The method of any one of embodiments 344 to 365, wherein obtaining the population of exosomes comprises storing the population of exosomes at room-temperature. 367. The method of any one of embodiments 344 to 366, wherein obtaining the population of exosomes comprises storing the population of exosomes without cryogenic preservation. 368. A composition comprising cultured stem cells and exosomes, wherein the exosomes were generated during culturing of the stem cells, collected, concentrated, and added back to the cultured stem cell composition. 369. The composition of embodiment 368, wherein the exosomes are paracrine signaling exosomes. 370. The composition of embodiment 368 or embodiment 369, wherein the cultured stem cell composition is subjected to at least 20 cumulative populations to a mammal in need of wound healing. 371. The composition of any one of embodiments 368 to 370, wherein the cultured stem cell composition is perturbed to elicit exosome production. 372. The composition of any one of embodiments 368 to 371, wherein the cultured stem cell composition is transformed to overexpress SDC2/S2/CD362/fibroglycan. 373. The composition of any one of embodiments 368 to 372, wherein the cultured stem cell composition is irradiated. 374. The composition of embodiment 373, wherein the cultured stem cell composition is irradiated using gamma irradiation. 375. The composition of any one of embodiments 368 to 374, wherein the cultured stem cell composition is subject to inflammatory stimulation. 376. The composition of embodiment 375, wherein the inflammatory stimulation comprises at least one of TNF-alpha, Interferon-gamma, Interferon-beta, Interleukin-1b, TLR agonists, Poly I:C, and LPS. 377. The composition of any one of embodiments 368 to 376, wherein the cultured stem cell composition is subject to growth arrest. 378. The composition of embodiment 377, wherein the growth arrest comprises at least one or gamma-irradiation, mitomycin-c, TGFb stimulation, and growing cells to confluence. 379. The composition of any one of embodiments 368 to 378, wherein the cultured stem cell composition comprises mesenchymal stem cells. 380. The composition of any one of embodiments 368 to 379, wherein the cultured stem cell composition comprises at least 20% SDC2+ mesenchymal stem cells. 381. The cell composition of any one of embodiments 368 to 380, wherein the cultured stem cell composition comprises at least 20% SDC2+ stem cells. 382. The composition of any one of embodiments 368 to 381, wherein the cultured stem cell composition comprises at least 30% SDC2+ stem cells. 383. The composition of any one of embodiments 368 to 382, wherein the cultured stem cell composition comprises at least 40% SDC2+ stem cells. 384. The composition of any one of embodiments 368 to 383, wherein the cultured stem cell composition comprises at least 50% SDC2+ stem cells. 385. The composition of any one of embodiments 368 to 384, wherein the cultured stem cell composition comprises at least 60% SDC2+ stem cells. 386. The composition of any one of embodiments 368 to 385, wherein the cultured stem cell composition comprises at least 70% SDC2+ stem cells. 387. The composition of any one of embodiments 368 to 386, wherein the cultured stem cell composition comprises at least 80% SDC2+ stem cells. 388. The composition of any one of embodiments 368 to 387, wherein the cultured stem cell composition comprises at least 90% SDC2+ stem cells. 389. The composition of any one of embodiments 368 to 388, wherein at least 30% of the exosomes comprise SDC2. 390. The composition of any one of embodiments 368 to 389, wherein at least 40% of the exosomes comprise SDC2. 391. The composition of any one of embodiments 368 to 390, wherein at least 50% of the exosomes comprise SDC2. 392. The composition of any one of embodiments 368 to 391, wherein at least 60% of the exosomes comprise SDC2. 393. The composition of any one of embodiments 368 to 392, wherein at least 70% of the exosomes comprise SDC2. 394. The composition of any one of embodiments 368 to 393, wherein at least 80% of the exosomes comprise SDC2. 395. The composition of any one of embodiments 368 to 394, wherein at least 90% of the exosomes comprise SDC2. 396. The composition of any one of embodiments 368 to 395, wherein at least 95% of the exosomes comprise SDC2. 397. The composition of any one of embodiments 368 to 396, wherein at least 99% of the exosomes comprise SDC2. 398. The composition of any one of embodiments 368 to 397, wherein exosomes comprise IL12, suppressor of cytokine signaling (SOCS), p53, PTEN, CD52, tsc1, Foxp3, Soluble Immune Response Suppressor (SIRS), TGFB, CD39, CD39L3, CD73, and maspin. 399. The composition of any one of embodiments 368 to 398, wherein the cultured stem cell composition comprises an immunosuppressive drug. 400. The composition of embodiment 399, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, and a cytotoxic antibiotic. 401. The composition of embodiment 399 or embodiment 400, wherein the immunosuppressive drug comprises at least one of a glucocorticoid, a cytostatic, an antibody, an immunophilin inhibitor, ciclosporin, tacrolimus, sirolimus and interferon, an opioid, a TNF binding protein, a cyclooxygenase inhibitor, an antihistamine, an antimetabolite, folic acid, methotrexate, a purine analogue, a pyrimidine analogue, a protein synthesis inhibitor, mycophenolate, a cytotoxic antibiotic, a steroid, an anti-TNF antibody, a TNF inhibitor, and an NSAID. 402. The composition of any one of embodiments 399 to 401, wherein the immunosuppressive drug comprises an anti-TNF antibody. 403. The composition of any one of embodiments 399 to 402, wherein the immunosuppressive drug comprises a TNF inhibitor. 404. The composition of any one of embodiments 399 to 403, wherein the immunosuppressive drug comprises an NSAID. 405. The composition of any one of embodiments 399 to 404, wherein the immunosuppressive drug comprises a steroid. 406. The composition of any one of embodiments 368 to 405, wherein the exosomes are purified. 407. The composition of any one of embodiments 368 to 406, wherein the exosomes are isolated. 408. A method of obtaining an immuno-modulatory composition comprising exosomes, comprising obtaining exosomes from a population of stromal cells that SDC2 are at least 20% SDC2+. 409. The method of embodiment 408, wherein the exosomes are paracrine signaling exosomes. 410. The method of embodiment 408 or embodiment 409, wherein the exosomes are SDC2−. 411. The method of embodiment 408 or embodiment 409, wherein the exosomes comprise SDC2 as an exosome surface constituent. 412. The method of embodiment 408 or embodiment 409, wherein the exosomes comprise SDC2 as an exosome interior constituent. 413. The method of any one of embodiments 408 to 412, wherein the exosomes are derived from a stromal cell induced to express SDC2. 414. The method of embodiment 413, comprising transforming the stromal cell to overexpress SDC2/S2/CD362/fibroglycan. 415. The method of embodiment 413, comprising irradiating the SDC2+ stromal cell. 416. The method of embodiment 415, comprising irradiating using gamma-irradiation. 417. The method of embodiment 413, comprising subjecting the SDC2+ stromal cell to inflammatory stimulation. 418. The method of embodiment 417, wherein the inflammatory stimulation comprises at least one of TNF-alpha, Interferon-gamma, Interferon-beta, Interleukin-1b, TLR agonists, Poly I:C, and LPS. 419. The method of embodiment 413, comprising subjecting the SDC2+ stromal cell to growth arrest. 420. The method of embodiment 419, wherein the growth arrest comprises at least one or gamma-irradiation, mitomycin-c, TGFb stimulation, and growing cells to confluence. 421. The method of any one of embodiments 408 to 420, comprising providing a physiologically acceptable buffer. 422. The method of any one of embodiments 411 to 421, wherein at least 30% of the exosomes comprise SDC2. 423. The method of any one of embodiments 411 to 422, wherein at least 40% of the exosomes comprise SDC2. 424. The method of any one of embodiments 411 to 423, wherein at least 50% of the exosomes comprise SDC2. 425. The method of any one of embodiments 411 to 424, wherein at least 60% of the exosomes comprise SDC2. 426. The method of any one of embodiments 411 to 425, wherein at least 70% of the exosomes comprise SDC2. 427. The method of any one of embodiments 411 to 426, wherein at least 80% of the exosomes comprise SDC2. 428. The method of any one of embodiments 411 to 427, wherein at least 90% of the exosomes comprise SDC2. 429. The method of any one of embodiments 411 to 428, wherein at least 95% of the exosomes comprise SDC2. 430. The method of any one of embodiments 411 to 429, wherein at least 99% of the exosomes comprise SDC2. 431. The method of any one of embodiments 408 to 430, wherein the exosomes are CD45−. 432. The method of any one of embodiments 408 to 431, wherein the composition does not comprise a living cell. 433. The method of any one of embodiments 408 to 432, wherein the composition is non-tumorigenic. 434. The method of any one of embodiments 408 to 433, wherein the composition is stable for over 48 hours without cryopreservation. 435. The method of any one of embodiments 408 to 434, wherein the composition comprises SDC2+ mesenchymal stem cells. 436. The method of any one of embodiments 408 to 435, wherein the composition is frozen. 437. The method of any one of embodiments 408 to 436, wherein the composition is lyophilized. 438. The method of any one of embodiments 408 to 437, wherein a therapeutically active amount of exosomes are obtained. 439. The method of any one of embodiments 408 to 438, wherein at least $10^6$ exosomes are obtained. 440. The method of any one of embodiments 408 to 439, wherein at least $10^7$ exosomes are obtained. 441. The method of any one of embodiments 408 to 440, wherein at least $10^8$ exosomes are obtained. 442. The method of any one of embodiments 408 to 441, wherein at least 1 μg of exosomes are obtained. 443. The method of any one of embodiments 408 to 442, wherein at least 10 μg of exosomes are obtained. 444. The method of any one of embodiments 408 to 443, wherein at least 20 μg of exosomes are obtained. 445. The method of any one of embodiments 408 to 444, wherein at least 50 μg of exosomes are obtained. 446. The method of any one of embodiments 408 to 445, wherein at least 100 μg of exosomes are obtained. 447. The method of any one of embodiments 408 to 446, wherein at least 150 μg of exosomes are obtained. 448. The method of any one of embodiments 408 to 447, wherein at least 200 μg of exosomes are obtained. 449. The method of any one of embodiments 408 to 448, wherein at least 250 μg of exosomes are obtained. 450. The method of any one of embodiments 408 to 449, wherein at least 500 μg of exosomes are obtained. 451. The method of any one of embodiments 408 to 450, wherein at least 750 μg of exosomes are obtained. 452. The method of any one of embodiments 408 to 451, wherein at least 1 mg of exosomes are obtained. 453. The method of any one of embodiments 408 to 452, wherein at least 2 mg of exosomes are obtained. 454. The method of any one of embodiments 408 to 453, wherein at least 3 mg of exosomes are obtained. 455. The method of any one of embodiments 408 to 454, wherein at least 4 mg of exosomes are obtained. 456. The method of any one of embodiments 408 to 455, wherein at least 5 mg of exosomes are obtained. 457. The method of any one of embodiments 408 to 456, wherein at least 6 mg of exosomes are obtained. 458. The method of any one of embodiments 408 to 457, wherein at least 7 mg of exosomes are obtained. 459. The method of any one of embodiments 408 to 458, wherein at least 100 mg of exosomes are obtained. 460. The method of any one of embodiments 408 to 459, wherein at least 200 mg of exosomes are obtained. 461. The method of any one of embodiments 408 to 460, wherein at least 300 mg of exosomes are obtained. 462. The method of any one of embodiments 408 to 461, wherein at least 400 mg of exosomes are obtained. 463. The method of any one of embodiments 408 to 462, wherein at least 500 mg of exosomes are obtained. 464. The method of any one of embodiments 408 to 463, wherein at least 600 mg of exosomes are obtained. 465. The method of any one of embodiments 408 to 464, wherein at least 700 mg of exosomes are obtained. 466. The method of any one of embodiments 408 to 465, wherein the exosomes are purified. 467. The method of any one of embodiments 408 to 466, wherein the exosomes are isolated. 468. The method of any one of embodiments 408 to 467, wherein the stromal cells are cultured in a hollow-fiber bioreactor.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: In Vitro Exosomes

A therapeutically active composition is prepared comprising in vitro SDC2+ exosomes. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is frozen for storage in phosphate buffer alone without the use of a cryoprotectant such as DMSO. When the composition is thawed, there is no loss therapeutic efficacy as measured by inhibition of the inflammatory response.

Example 2: In Vitro Exosomes and SDC2+ Mesenchymal Stromal Stem Cells

A therapeutically active composition is prepared comprising in vitro SDC2+ exosomes. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is combined with SDC2+ mesenchymal stromal stem cells. Addition of the exosome composition enhances the therapeutic activity of the SDC2+ mesenchymal stromal stem cells in reducing the inflammatory response.

Example 3: In Vitro Exosomes and Regulatory T Cells

A therapeutically active composition is prepared comprising in vitro SDC2+ exosomes. The SDC2+ exosome composition is prepared to include infliximab contained within the exosome composition. When the composition is administered to the patient, the infliximab is not exposed to the humoral immune system and the patient does not develop humoral immune response toward the infliximab. When a sample of the composition is tested, at least 30% of the exosomes are found to comprise SDC2. The exosome composition is combined with CD25+CD4+Foxp3+ regulatory T cells. Addition of the exosome composition enhances the therapeutic activity of the CD25+CD4+Foxp3+ regulatory T cells in reducing the inflammatory response.

Example 4: Treatment of Diabetic Ulcers

A therapeutically active in vitro SDC2+ exosome composition is used to treat an individual who is in need of treatment of diabetic ulcers. A doctor prescribes the therapeutically active in vitro SDC2+ exosome composition formulated with a collagen ointment for topical use and instructs the patient to administer the composition 1-5 times per week to the diabetic ulcers. After administration of the composition to the diabetic ulcers for one week, the ulcers have decreased in severity. After administration of the composition to the diabetic ulcers for one month, the ulcers have largely healed.

Example 5: Treatment of Rheumatoid Arthritis

A therapeutically active in vitro SDC2+ exosome composition additionally comprising infliximab is used to treat an individual who is in need of treatment of rheumatoid arthritis. A doctor prescribes the therapeutically active in vitro SDC2+ exosome composition formulated for subcutaneous administration and instructs the patient to administer the composition weekly by subcutaneous injection. After administration of the composition to the subject, the joint pain experienced by the patient is decreased by at least 50% and the joint mobility of the patient is increased by at least 60%. Further, the patient does not experience a humoral immune response to infliximab.

Example 6: Treatment of Amyotrophic Lateral Sclerosis

A therapeutically active in vitro SDC2+ exosome composition is used to treat an individual who is in need of treatment of amyotrophic lateral sclerosis (ALS). A doctor prescribes the therapeutically active in vitro SDC2+ exosome composition formulated for intrathecal administration at the doctor's office and instructs the patient to come for weekly intrathecal injections. After administration of the composition to the subject, the symptoms experienced by the patient are decreased. When 10 patients are given the intrathecal injections of the composition, 8 of them experience minimal decrease in motor neuron function and stabilization of their condition. When 10 patients are given an alternative treatment, 3 of them experience minimal decrease minimal decrease in motor neuron function and stabilization of their condition.

Example 7: Isolation

An immuno-modulatory composition is obtained by isolating exosomes that express SDC2. The composition is isolated from SDC2+ stromal cells that have been transformed with a lentivirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes and the potency of the exosomes produced by the cells.

The isolated exosomes are analyzed and it is determined that at least 20% of the exosomes are SDC2+ and 700 mg of exosomes are obtained. The exosomes are diluted using a phosphate buffer and frozen without DMSO in single use vials until needed for use.

Example 8: Isolation Using Antibody Purification

An immuno-modulatory composition is obtained by isolating exosomes that express SDC2. The composition is isolated from SDC2+ stromal cells that have been transformed with a lentivirus or adenovirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes. The composition comprising exosomes is incubated with an anti-SDC2 antibody for 10-30 minutes or overnight at 4° C. The SDC2+ exosomes are isolated from the solution using flow cytometry based sorting or column chromatography and the SDC2+ exosomes are eluted from the column.

The isolated exosomes are analyzed and it is determined that at least 80% of the exosomes are SDC2+ and 700 mg of exosomes are obtained. The exosomes are diluted using a phosphate buffer and frozen without DMSO in single use vials until needed for use.

Example 9: Isolation Using Ultracentrifugation

An immuno-modulatory composition is obtained by isolating exosomes that express SDC2. The composition is isolated from SDC2+ stromal cells that have been transformed with a lentivirus or adenovirus that carries the SDC2 gene such that the SDC2+ stromal cells are over-expressing SDC2. Over-expression of SDC2 has the effect of increasing the number of SDC2+ exosomes and as a consequence increases the efficiency of isolating the exosomes. Supernatant from the SDC2+ cells containing the exosomes is subjected to ultracentrifugation at 100,000×g force for 16 hours at 4° C. The exosome fraction is isolated from the media solution. For some uses, ultrafiltration with a subsequent liquid chromatography (UF-LC) steps is performed on the resulting product to produce a more pure preparation of SDC2+ exosomes.

The isolated exosomes are analyzed and it is determined that at least 80% of the exosomes are SDC2+ and 700 mg of exosomes are obtained. The exosomes are diluted using a phosphate buffer and frozen without DMSO in single use vials until needed for use.

Example 10: Isolation Using Hollow-Fiber Bioreactors (HFBRs)

Human mesenchymal stem cells (MSCs), such as SDC2+ MSCs are grown in a C2011 cartridge (FiberCell Systems), or alternatively in a Terumo Quantum Cell Expansion System, seeded with $1\times10^7$ to $1\times10^8$ MSCs. It continuously produces exosomes for 10 weeks. The typical harvest from the extracapillary space of the cartridge is $1.1\times10^{12}$ exosomes/ml in a volume of 400 ml. The total bioreactor yield or exosomes by number is approximately 10-fold higher at a concentration that was 10-fold higher. Harvests are performed every two weeks, and prior to each harvest, small samples of cells are collected for phenotypic analysis. During these 10 weeks, the culture does not expand based on glucose uptake rate, which remains fairly constant. By orthogonal measure, the phenotype of the cells remains constant as well. Exosomes are continuously harvested without splitting and/or subculturing of the cells.

Example 11: Delivery of an Exosome Composition

An immuno-modulatory signal is delivered to the intracellular space of an individual using exosomes isolated from SDC2+ stem cells. The exosomes are formulated to contain infliximab. The exosomes are administered to the individual subcutaneously and the contents of the exosome are delivered to the intracellular space of the individual, thereby delivering the immuno-modulatory signal. Administration of the exosomes and delivery of the immuno-modulatory signal does not result in a humoral immune response by the individual to the infliximab, thereby increasing the potency of the infliximab.

Example 12: Supplemented Stem Cell Compositions

A therapeutically active composition is prepared comprising in vitro SDC2+ exosomes derived from mesenchymal stromal stem cells. When a sample of the prepared composition is tested, at least 30% of the exosomes are found to comprise SDC2. The SDC2+ exosomes are combined with the mesenchymal stromal stem cells and the resulting mixture is administered to an individual in need of wound healing. The result of this treatment is enhanced wound healing compared to administration of the mesenchymal stromal stem cells alone.

Example 13: Exosome Delivery to Treat ARDS Lung Injury

Exosomes were tested in a rat model of ARDS. Briefly, 300 g Sprague Dawley rats were given an intrapulmonary dose of *E. coli* to induce ARDS lung injury, one hour later, the rats were treated with a 90-100 µg dose of exosomes or 4 million human mesenchymal stem cells (hMSC). The extent of lung injury was then measured 24 hours later by measurement of arterial oxygen, BAL bacterial load, BAL cell infiltration, static compliance, and a lung wet dry ratio. An improvement in arterial FI 0.3 was observed by treatment with exosomes compared to vehicle (FIG. 4). This demonstrates that exosomes are able to treat lung damage in an ARDS lung injury model. Exosome treatment was shown to be safe as PBS vehicle treatment in arterial FI 1.0 measurement which showed a similar measurement between exosome treatment and PBS vehicle control (FIG. 5).

Arterial oxygen was also measured for bone marrow (BM) exosomes and human umbilical cord (HUC) exosome treatment with arterial FI 0.3 (FIG. 6) and arterial FI 1.0 (FIG. 7) compared to PBS vehicle control. In FIG. 6 and FIG. 7, BM exosomes and HUC exosomes were shown to be just as safe as PBS vehicle control on arterial FI 0.3 or FI 1.0.

In FIG. 8 bacterial load was measured in the bronchioalveolar lavage (BAL). In this measurement, a measurable reduction was observed in BAL bacterial load in rats treated with exosomes and hMSC. BAL total cell count and neutrophil count are shown in FIG. 9 and FIG. 10. In this assay, a measurable difference was observed in BAL total cell count and BAL neutrophil count in rats treated with exosomes and hMSC compared to vehicle control.

Static lung compliance and lung wet dry ratio were also measured in rats treated with exosomes and hMSC compared to PBS vehicle control (FIG. 11). This measurement showed exosomes were just as safe as PBS vehicle control. FIG. 12 shows the results of wet dry ratio in rats that were treated with exosomes or hMSC. This also showed that exosomes were just as safe as PBS vehicle control.

This example shows safety and efficacy of exosomes compared to PBS vehicle control.

Example 14: Scratch Wound Assay

A scratch wound assay was performed on A549 cells to observe the effect of exosomes on cell migration. In this assay, 300,000 A549 cells were grown in a monolayer in a 24 well plate. The cells were scraped with a p200 pipet tip in a straight line to create a scratch. An image was taken at the time of scraping (0 h) and after a 48 hour incubation with serum free media or 2 µg SDC2+ exosomes in serum free media. As shown in FIG. 13 and FIG. 14, incubation with exosomes resulted in a reduced scratch size compared to serum free media.

This example shows increased cell migration in cells treated with exosomes compared to cells treated with serum free media alone.

Example 15: NFκB Reporter Assay

An NFκB assay was performed on A549 cells treated with serum free media or exosomes in serum free media. The results of these assays are shown in FIGS. 15-18. In this assay, 30,000 A549 cells that were transfected with an NFκB-luciferase reporter gene were grown in a 96 well dish. The cells were treated with serum free media or 2 µg exosomes in serum free media for 24 hours and then stimulated with human IL-1β for 24 hours and luciferase activity was measured. A reduction was observed in luciferase activity in A549 cells treated with exosomes obtained by ultrafiltration followed by ultracentrifugation (FIG. 15 and FIG. 16) as well as exosomes obtained by ultracentrifugation without ultrafiltration (FIG. 17 and FIG. 18).

This example shows a reduction in the inflammatory response in cells treated with exosomes compared to cells treated with serum free media alone.

Example 16: Exosome Delivery to Treat ARDS Lung Injury

Exosomes were tested in a rat model of ARDS. Briefly, 300 g Sprague Dawley rats were given an intrapulmonary dose of *E. coli* to induce ARDS lung injury, one hour later, the rats were treated with an intravenous dose of 200 µg or 10 mill/kg human mesenchymal stem cells (hMSC). The extent of lung injury was then measured 24 hours later by measurement of arterial oxygen, BAL bacterial load, BAL cell infiltration, static compliance, and a lung wet dry ratio. An improvement in arterial FI 0.3 was observed by treatment with exosomes compared to vehicle (one way anova $p<0.0001$) (FIG. 19). An improvement was also observed in arterial FI 1.0 was observed by treatment with exosomes compared to vehicle (one way anova $p<0.0001$) (FIG. 20). This demonstrates that exosomes are able to treat lung damage in an ARDS lung injury model.

Static lung compliance was also measured in rats treated with exosomes or hMSC compared to PBS vehicle control (FIG. 21). This measurement showed exosomes effective in treating ARDS lung injury compared to control (one way anova $p<0.01$).

In FIG. 22 bacterial load was measured in the bronchioalveolar lavage (BAL). In this measurement, a significant reduction was observed in BAL bacterial load in rats treated with exosomes and hMSC (one way anova $p<0.01$). BAL total cell count and neutrophil count are shown in FIG. 23 and FIG. 24. In this assay, a significant difference was observed in BAL total cell count and BAL neutrophil count in rats treated with exosomes and hMSC compared to vehicle control (one way anova $p<0.01$).

This example shows exosome administration with an increased dose and intravenous mode of administration treats ARDS lung injury.

Example 17: Treatment of Diabetes-Associated Kidney Failure

A therapeutically active in vitro SDC2+ exosome composition is used to treat an individual suffering from kidney failure related to diabetes. After administration of the composition to the subject, the symptoms experienced by the patient are decreased. When 10 patients are given the intrathecal injections of the composition, 9 experience marked increase in kidney function. When 10 patients are given an alternative treatment, the kidney function is not improved. No impact upon blood glucose levels is observed in some individuals.

Example 18: Treatment of Alzheimer's Disease

A therapeutically active in vitro SDC2+ exosome composition is used to treat an individual suffering from Alzheimer's disease. After administration of the composition to the subject by intravenous administration, the composition is able to cross the blood brain barrier and treat the brain and Alzheimer's disease symptoms are decreased. When 10 patients are given the intravenous injection of the composition, 9 experience an improvement in memory.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of reducing an inflammation response in a mammal comprising delivering a composition comprising syndecan-2 (SDC2)+ exosomes derived from a population of stromal stem cells to a site of the inflammation response, wherein 20% or more of the population of stromal stem cells are positive for SDC2.

2. The method of claim 1, wherein said delivering comprises topically applying said composition comprising SDC2+ exosomes.

3. The method of claim 1, wherein said delivering comprises inhalation.

4. The method of claim 1, wherein the composition further comprises SDC2+ mesenchymal stem cells.

5. The method of claim 1, wherein the inflammation response comprises a diabetic complication.

6. The method of claim 5, wherein the diabetic complication comprises at least one of atherosclerosis, nephropathy, cardiomyopathy, neuropathy, a kidney disorder, kidney failure, a diabetic ulcer, and a leg ulcer.

7. The method of claim 1, wherein the inflammation response comprises at least one of acute respiratory distress syndrome (ARDS), sepsis, Antisynthetase syndrome, asthma, chronic obstructive pulmonary disease, cystic fibrosis, atelectasis, bronchitis, emphysema, pneumonia, and pulmonary edema.

* * * * *